(12) United States Patent
Huang et al.

(10) Patent No.: US 8,895,571 B2
(45) Date of Patent: Nov. 25, 2014

(54) ISOINDOLINONE AND PYRROLOPYRIDINONE DERIVATIVES AS AKT INHIBITORS

(71) Applicant: Incyte Corporation, Wilmington, DE (US)

(72) Inventors: Taisheng Huang, Wilmington, DE (US); Hao Feng, Aston, PA (US); Lingquan Kong, Hockessin, DE (US); Anlai Wang, Wilmington, DE (US); Hai Fen Ye, Newark, DE (US); Chu-Biao Xue, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 112 days.

(21) Appl. No.: 13/650,373

(22) Filed: Oct. 12, 2012

(65) Prior Publication Data

US 2013/0096144 A1 Apr. 18, 2013

Related U.S. Application Data

(60) Provisional application No. 61/547,293, filed on Oct. 14, 2011.

(51) Int. Cl.
| | |
|---|---|
| *A61K 31/4155* | (2006.01) |
| *C07D 409/14* | (2006.01) |
| *C07D 401/14* | (2006.01) |
| *A61K 31/4439* | (2006.01) |
| *A61K 31/519* | (2006.01) |
| *A61K 31/506* | (2006.01) |
| *A61K 31/427* | (2006.01) |
| *C07D 471/04* | (2006.01) |
| *A61K 31/437* | (2006.01) |
| *C07D 487/04* | (2006.01) |
| *C07D 403/10* | (2006.01) |
| *C07D 403/14* | (2006.01) |
| *C07D 417/14* | (2006.01) |
| *C07D 471/02* | (2006.01) |
| *C07D 487/02* | (2006.01) |
| *C07D 403/04* | (2006.01) |

(52) U.S. Cl.
CPC ............ *C07D 403/04* (2013.01); *C07D 409/14* (2013.01); *C07D 417/14* (2013.01); *C07D 401/14* (2013.01); *C07D 471/02* (2013.01); *C07D 403/14* (2013.01); *C07D 487/02* (2013.01)
USPC ........ 514/265.1; 514/256; 514/300; 514/339; 514/365; 514/406; 544/280; 544/333; 546/113; 546/275.4; 548/204; 548/364.7

(58) Field of Classification Search
None
See application file for complete search history.

(56) References Cited

U.S. PATENT DOCUMENTS

| 4,988,616 A | 1/1991 | Heidenreich et al. |
| 6,583,144 B2 | 6/2003 | Ohkura et al. |
| 7,589,117 B2 | 9/2009 | Kleemann et al. |

FOREIGN PATENT DOCUMENTS

| WO | WO 02/00196 | 1/2002 |
| WO | WO 02/096873 | 12/2002 |
| WO | WO 2005/021532 | 3/2005 |
| WO | WO 2005/035495 | 4/2005 |
| WO | WO 2005/074643 | 8/2005 |
| WO | WO 2005/113762 | 12/2005 |
| WO | WO 2006/020879 | 2/2006 |
| WO | WO 2006/024837 | 3/2006 |
| WO | WO 2006/036670 | 4/2006 |
| WO | WO 2006/125180 | 11/2006 |
| WO | WO 2007/021308 | 2/2007 |
| WO | WO 2007/021309 | 2/2007 |
| WO | WO 2007/047646 | 4/2007 |
| WO | WO 2007/053503 | 5/2007 |
| WO | WO 2008/008022 | 1/2008 |
| WO | WO 2008/121786 | 10/2008 |
| WO | WO 2008/153902 | 12/2008 |
| WO | WO 2009/156735 | 12/2009 |
| WO | WO 2011/080718 | 7/2011 |
| WO | WO 2012/058133 | 5/2012 |

OTHER PUBLICATIONS

Bellacosa et al., *Int. J. Cancer*, 64:280-285 (1995).
Berge et al., "Pharmaceutical Salts," *Journal of Pharmaceutical Science*, 66, 2 (1977).
Blom, K., "Two-pump at column dilution configuration for preparative LC-MS", *J. Combi. Chem.*, 4, 295 (2002).
Blom et al., "Optimizing preparative LC-MS configurations and methods for parallel synthesis purification", *J. Combi. Chem.*, 5, 670 (2003).
Blom et al., "Preparative LC-MS purification: Improved compound specific method optimization", *J. Combi. Chem.*, 6, 874-883 (2004).
Brognard et al., *Cancer Res.*, 61:3986 (2001).
Chalhoub and Baker, "PTEN and the PI3-Kinase Pathway in Cancer," *Ann. Rev. Pathol. Mech. Dis.*, 4:127-150 (2009).
Cheng et al., "AKT2, a putative oncogene encoding a member of a subfamily of protein-serine/threonine kinases, is amplified in human ovarian carcinomas," *Proc. Natl. Acad. Sci. USA*, 89:9267 (1992).
Cheng et al., "Amplification of AKT2 in human pancreatic cancer cells and inhibition of AKT2 expression and tumorigenicity by antisense RNA," *Proc. Natl. Acad. Sci. USA*, 93:3636-3641 (1996).
Graff et al., "Increased AKT Activity Contributes to Prostate Cancer Progression by Dramatically Accelerating Prostate Tumor Growth and Diminishing p27$^{Kip1}$," *J. Biol. Chem.*,275:24500 (2000).

(Continued)

*Primary Examiner* — Michael Barker
*Assistant Examiner* — Po-Chih Chen
(74) *Attorney, Agent, or Firm* — Fish & Richardson P.C.

(57) ABSTRACT

The present invention provides isoindolinone and pyrrolopyridinone derivatives, as well as their compositions and methods of use, that inhibit the activity of the serine/threonine kinase, Akt, and are useful in the treatment of diseases related to the activity of Akt including, for example, cancer and other diseases.

35 Claims, No Drawings

(56) References Cited

OTHER PUBLICATIONS

Graham, Patrick L: "An Introduction to Medicinal Chemistry, Chapter 10: Drug Design: Optimizing Target Interactions ED," Jan. 1, 1995, An Introduction to Medicinal Chemistry, Oxford Univ. Press, Oxford [U.A.], pp. 210-212.

Haas Kogan et al., "Protein kinase B (PKB/Akt) activity is elevated in glioblastoma cells due to mutation of the tumor suppressor PTEN/MMAC," *Curr. Biol.*, 8:1195 (1998).

Hay N., "The Akt-mTOR tango and its relevance to cancer," *Cancer Cell*, 8:179-183 (2005).

Heerding, Dirk A, et al: "Identification of 4-(4-Amino-1,2,5-oxadiazol-3-yl)-1-ethyl-7-{[(3 S )-3-piperidinylmethyl]oxy}-1 H-imidazo[4,5- c ]pyridine-4-yl)-2-methyl-3-butyn-2-ol (GSK690693), a Novel Inhibitor of AKT Kinase", Journal of Medicinal Chemistry, vol. 51, No. 18, Sep. 25, 2008, pp. 5663-5679.

Hemmings, "Akt Signaling—Linking Membrane Events to Life and Death Decisions," B. A. *Science*, 275:628 (1997).

International Search Report and Written Opinion in PCT/US2012/059905 dated Feb. 15, 2013.

Karst A. M., et al., "Role of p53 Up-regulated Modulator of Apoptosis and Phosphorylated Akt in Melanoma Cell Growth, Apoptosis, and Patient Survival," 66:9221-9226 (2006).

Li et al., "Targeting Serine/Threonine Protein Kinase B/Akt and Cell-cycle Checkpoint Kinases for Treating Cancer," *Current Topics in Med. Chem.*, 2:939-971 (2002).

Mattmann, Margrith E. et al: "Inhibition of Akt with small molecules and bilogics: historical perspective and current status of the patent landscape/x-ms-", Expert Opinion on Therapeutic Patents, Informa Healthcare, GB, vol. 21, No. 9, Jan. 1, 2011, pp. 1309-1338.

Nakatani et al., "Up-regulation of Akt3 in Estrogen Receptor-deficient Breast Cancers and Androgen-independent Prostate Cancer Lines" *J. Biol. Chem.*, 274:21528-21532 (1999).

Nakatani, K., *Biochem. Biophys. Res. Commun..*, 257:906 (1999).

Staal, S. P., *Proc. Natl. Acad. Sci.*, 84:5034 (1987).

Steelman et al., "Roles of Raf/MEK/ERK and PI3K/PTEN/Akt/mTOR pathways in controlling growth and sensitivity to therapy-implications for cancer and aging," *Aging*, 3(3):192-222 (2011).

International Preliminary Report on Patentability in International Application No. PCT/US2012/059905, issued Apr. 15, 2014, 8 pages.

Toker et al., *Cancer Res.*, 66(8):3963-3966 (2006).

Zinda et al., *Clin. Cancer Res.*, 7:2475 (2001).

ISOINDOLINONE AND PYRROLOPYRIDINONE DERIVATIVES AS AKT INHIBITORS

FIELD OF THE INVENTION

The present invention provides isoindolinone and pyrrolopyridinone derivatives, as well as their compositions and methods of use that inhibit the activity of the serine/threonine kinase, Akt, and are useful in the treatment of diseases related to the activity of Akt including, for example, cancer and other diseases.

BACKGROUND OF THE INVENTION

The 57 KD serine/threonine kinase, Akt, plays an important role in the regulation of cell survival. Also known as protein kinase B (PKB), Akt is involved in promoting the proliferation and survival of a wide range of cell types, thereby protecting cells from apoptosis. Three members of the Akt subfamily have been identified: Akt1, Akt, and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). Akt activity is regulated by various protein kinases and phosphatases. Akt is downstream of phosphatidylinositol 3-kinase (PI3K) in the signal transduction pathway (Hemmings, B. A. (1997) Science 275:628; Hay N. (2005) Cancer Cell 8:179-183). For instance, activation of Akt is mediated by PI3K which initiates the binding of second messenger phospholipids (e.g. phosphatidyl-inositol 3,4,5-trisphosphate and phosphatidylinositol 3,4-bisphosphate) to the pleckstrin homology (PH) binding domain of Akt, thereby resulting in phosphorylation and activation of the enzyme. An overview of the signaling pathway involving Akt is discussed in Steelman, et al. "Roles of Raf/MEK/ERK and PI3K/PTEN/Akt/mTOR pathways in controlling growth and sensitivity to therapy-implications for cancer and aging." Aging, March 2011, Vol. 3, No. 3, 192-222.

Akt is believed to contribute to cancerous disease states by inhibiting apoptosis and promoting both angiogenesis and proliferation (Toker et al (2006) Cancer Res. 66(8):3963-3966). Overexpression or amplification of Akt has been associated with certain cancers. For example, Akt2 is overexpressed in ovarian cancer (Cheng et al (1992) Proc. Natl. Acad. Sci. USA 89:9267); pancreatic cancer (Cheng et al. (1996) Proc. Natl. Acad. Sci. U.S.A. 93:3636-3641; Bellacosa et al (1995) Int. J. Cancer 64:280-285); and head and neck cancer (Calhoub N. et al. (2009) Ann. Rev. Pathol. Mech Dis. 4:127-150). Similarly, Akt3 was found to be overexpressed in breast and prostate cancer cell lines (Nakatani et al. J. Biol. Chem. 274:21528-21532 (1999). Akt has also been found to be overexpressed in, for example, colon cancer (Zinda et al (2001) Clin. Cancer Res. 7:2475), brain cancer (Haas Kogan et al (1998) Curr. Biol. 8:1195), lung cancer (Brognard et al (2001) Cancer Res. 61:3986), prostate cancer (Graff et al (2000) J. Biol. Chem. 275:24500) and gastric carcinomas (Staal et al (1987) Proc. Natl. Acad. Sci. USA 84:5034-5037). Dysregulation of the Akt pathway has also been associated with melanoma (Karst A. M., et al. (2006) 66:9221-9226). Activation of Akt has also been implicated as a risk factor for hepatocellular carcinoma (HCC) (Steelman, et al. Aging, March 2011, Vol. 3, No. 3, 192-222).

Because of its contributing role in the regulation of cell survival, Akt provides an important therapeutic target for the effective treatment of various disorders, particularly cancer. Thus, new or improved agents which inhibit kinases such as Akt are continually needed for developing new and more effective pharmaceuticals that are aimed at treating diseases associated with dysregulation of the pathways involving Akt. The compounds, compositions, and methods of the invention described herein are directed toward these needs and other ends.

SUMMARY OF THE INVENTION

The present invention provides, inter alia, a compound of Formula I:

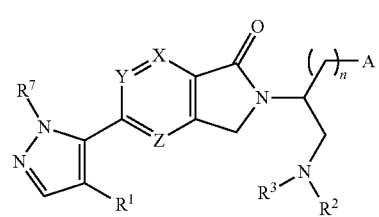

or a pharmaceutically acceptable salt thereof; wherein constituent members are defined below.

The present invention also provides a composition comprising a compound of Formula I, or a pharmaceutically acceptable salt thereof, and at least one pharmaceutically acceptable carrier.

The present invention also provides methods of treating cancer and other diseases comprising administering to a patient a therapeutically effective amount of a compound of Formula I, or a pharmaceutically acceptable salt thereof.

The details of one or more embodiments of the invention are set forth in the description below. Other features, objects, and advantages of the invention will be apparent from the description and from the claims.

DETAILED DESCRIPTION

The present invention provides, inter alia, a compound of Formula I:

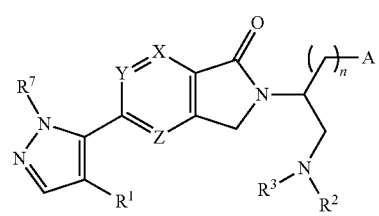

or a pharmaceutically acceptable salt thereof; wherein:

X is N or $CR^4$;

Y is N or $CR^5$;

Z is N or $CR^6$, provided at least one of X, Y, and Z is carbon;

A is $C_{6-10}$ aryl, 5-10 membered heteroaryl, or $C_{3-7}$ cycloalkyl, wherein said $C_{6-10}$ aryl, 5-10 membered heteroaryl, and $C_{3-7}$ cycloalkyl are each optionally substituted with 1, 2, 3, 4, or 5 substituents independently selected from Q;

$R^1$ is H, F, Cl, Br, CN, $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 4-6 membered heterocycloalkyl, or 5-10 membered heteroaryl, wherein said $C_{1-6}$ alkyl, $C_{2-6}$ alkenyl, $C_{2-6}$ alkynyl, $C_{3-6}$ cycloalkyl, $C_{6-10}$ aryl, 4-6 membered heterocycloalkyl, and 5-10 membered heteroaryl are each optionally substituted with 1, 2, or 3 substituents independently selected from Cy, halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$, wherein no more than one of said 1, 2, or 3 substituents is Cy;

$R^2$ is H, $C_{1-6}$ alkyl, $C_{3-6}$ cycloalkyl, or 4-6 membered heterocycloalkyl, wherein said 4-6 membered heterocycloalkyl is optionally substituted by 1, 2, or 3 substituents independently selected from $R^A$;

$R^3$ is H or $C_{1-3}$ alkyl;

or $R^2$ and $R^3$ together with the nitrogen atom to which they are both attached form a 4-6 membered heterocycloalkyl group optionally substituted by 1 or 2 substituents independently selected from $R^A$;

$R^4$ is H, F, Cl, CN, or $C_{1-3}$ alkyl;

$R^5$ is H, F, Cl, CN, or $C_{1-3}$ alkyl;

$R^6$ is H, F, Cl, CN, or $C_{1-3}$ alkyl;

$R^7$ is $C_{1-3}$ alkyl;

Q is independently selected from $Cy^1$, $-L-Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; wherein no more than two Q are independently selected from $Cy^1$ and $-L-Cy^1$, and wherein said $C_{1-6}$ alkyl, $C_{2-6}$ alkenyl, $C_{2-6}$ alkynyl, and $C_{1-6}$ haloalkyl, are each optionally substituted by 1, 2, 3, 4 or 5 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2 NR^{c1}R^{d1}$;

L is $C_{1-3}$ alkylene, $(C_{1-3}$ alkylene$)_pO(C_{1-3}$ alkylene$)_q$, $(C_{1-3}$ alkylene$)_pS(C_{1-3}$ alkylene$)_q$, $(C_{1-3}$ alkylene$)_pC(O)(C_{1-3}$ alkylene$)_q$, $(C_{1-3}$ alkylene$)_pC(O)NR^e(C_{1-3}$ alkylene$)_q$, $(C_{1-3}$ alkylene$)_pC(O)O(C_{1-3}$ alkylene$)_q$, $(C_{1-3}$ alkylene$)_pOC(O)(C_{1-3}$ alkylene$)_q$, $(C_{1-3}$ alkylene$)_pOC(O)NR^e(C_{1-3}$ alkylene$)_q$, $(C_{1-3}$ alkylene$)_pNR^eC(O)NR^f(C_{1-3}$ alkylene$)_q$, $(C_{1-3}$ alkylene$)_pNR^e(C_{1-3}$ alkylene$)_q$, $(C_{1-3}$ alkylene$)_pS(O)(C_{1-3}$ alkylene$)_q$, $(C_{1-3}$ alkylene$)_pS(O)NR^e(C_{1-3}$ alkylene$)_q$, $(C_{1-3}$ alkylene$)_pS(O)_2(C_{1-3}$ alkylene$)_q$, or $(C_{1-3}$ alkylene$)_pS(O)_2NR^e(C_{1-3}$ alkylene$)_q$, wherein said $C_{1-3}$ alkylene occurring in any of the options for L is optionally substituted with 1, 2, or 3 substituents independently selected from F, Cl, CN, $NH_2$, $NH(C_{1-3}$ alkyl) or $N(C_{1-3}$ alkyl$)_2$;

Cy is $C_{3-6}$ cycloalkyl, $C_{6-10}$ aryl, 4-6 membered heterocycloalkyl, or 5-10 membered heteroaryl, wherein said $C_{3-6}$ cycloalkyl, $C_{6-10}$ aryl, 4-6 membered heterocycloalkyl, and 5-10 membered heteroaryl are each optionally substituted by 1, 2, or 3 substituents independently selected from $Cy^2$ and $R^B$, wherein no more than one of said 1, 2, or 3 substituents is $Cy^2$;

$Cy^1$ is $C_{3-6}$ cycloalkyl, $C_{6-10}$ aryl, 4-6 membered heterocycloalkyl, or 5-6 membered heteroaryl, wherein said $C_{3-6}$ cycloalkyl, $C_{6-10}$ aryl, 4-6 membered heterocycloalkyl, and 5-6 membered heteroaryl are each optionally substituted with 1, 2, or 3 substituents independently selected from $R^C$;

$Cy^2$ is $C_{3-6}$ cycloalkyl, $C_{6-10}$ aryl, 4-6 membered heterocycloalkyl, or 5-6 membered heteroaryl, wherein said $C_{3-6}$ cycloalkyl, $C_{6-10}$ aryl, 4-6 membered heterocycloalkyl, and 5-6 membered heteroaryl are each optionally substituted with 1, 2, or 3 substituents independently selected from $R^D$;

$R^A$, $R^B$, $R^C$, and $R^D$ are each independently selected from halo, CN, $C_{1-3}$ alkyl, $C_{1-3}$ haloalkyl, $NO_2$, $OR^{a2}$, $C(O)R^{b2}$, $C(O)NR^{c2}R^{d2}$, $C(O)OR^{a2}$, $OC(O)R^{b2}$, $NR^{c1}R^{d1}$, $NR^{c2}C(O)R^{b2}$, $NR^{c2}C(O)NR^{c2}R^{d2}$, $NR^{c2}C(O)OR^{a2}$, $S(O)_2R^{b2}$, $NR^{c2}S(O)_2R^{b2}$, and $S(O)_2NR^{c2}R^{d2}$;

$R^a$, $R^b$, $R^c$, $R^d$, $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl, wherein said $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl are each optionally substituted with 1, 2, 3, 4, or 5 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

or $R^c$ and $R^d$ together with the N atom to which they are attached form a 4-, 5-, 6- or 7-membered heterocycloalkyl group or 5-membered heteroaryl group, each optionally substituted with 1, 2, or 3 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $C(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

or $R^{c1}$ and $R^{d1}$ together with the N atom to which they are attached form a 4-, 5-, 6- or 7-membered heterocycloalkyl group or 5-membered heteroaryl group, each optionally substituted with 1, 2, or 3 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $C(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

$R^{a2}$, $R^{b2}$, $R^{c2}$, and $R^{d2}$ are each independently selected from H, $C_{1-3}$ alkyl, and $C_{3-6}$ cycloalkyl;

or $R^{c2}$ and $R^{d2}$ together with the N atom to which they are attached form a 4-, 5-, or 6-membered heterocycloalkyl group or 5-membered heteroaryl group;

$R^{a3}$, $R^{b3}$, $R^{a1}$, and $R^{d3}$ are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c3}$ and $R^{d3}$ together with the N atom to which they are attached form a 4-, 5-, 6- or 7-membered heterocycloalkyl group or 5-membered heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$ and $R^f$ are each independently selected from H and $C_{1-4}$ alkyl;

$R^g$ is H, CN, or $NO_2$;

n is 0 or 1;
p is 0 or 1; and
q is 0 or 1.

In some embodiments, X is $CR^4$; Y is $CR^5$; and Z is $CR^6$.
In some embodiments, X is N; Y is $CR^5$; and Z is $CR^6$.
In some embodiments, X is $CR^4$; Y is N; and Z is $CR^6$.
In some embodiments, X is $CR^4$; Y is $CR^5$; and Z is N.

In some embodiments, $R^2$ is H, $C_{1-6}$ alkyl, $C_{3-6}$ cycloalkyl, or 4-6 membered heterocycloalkyl, wherein said 4-6 membered heterocycloalkyl is optionally substituted by $C_{1-3}$ alkyl.

In some embodiments, $R^2$ is H or $C_{1-6}$ alkyl.
In some embodiments, $R^3$ is H.
In some embodiments, $R^2$ and $R^3$ are both H.

In some embodiments, $R^1$ is H, F, Cl, Br, CN, $C_{1-6}$ alkyl, $C_{2-6}$ alkynyl, $C_{6-10}$ aryl, or 5-10 membered heteroaryl, wherein said $C_{1-6}$ alkyl, $C_{2-6}$ alkynyl, $C_{6-10}$ aryl, 4-6 membered heterocycloalkyl, and 5-10 membered heteroaryl are each optionally substituted with one substituent selected from halo, $C_{1-6}$ alkyl, $OR^a$, $SR^a$, and $C(O)NR^cR^d$.

In some embodiments, $R^1$ is selected from H, F, Cl, Br, CN, methyl, methoxymethyl, ethoxymethyl, n-propyloxymethyl, isopropyloxymethyl, cyclobutyloxymethyl, cyclopropylmethyloxymethyl, methylthiomethyl, ethylthiomethyl, phenyl, thienyl, pyridinyl, methylpyrazolyl, thiazolyl, naphthyl, pyrimidinyl, fluoropyridinyl, methoxypyridinyl, methylaminocarbonylpyridinyl, and hydroxymethylbutynyl.

In some embodiments, $R^1$ is selected from H, F, Cl, Br, CN, and methyl.

In some embodiments, $R^1$ is H.

In some embodiments, A is phenyl optionally substituted with 1, 2, 3, 4, or 5 substituents independently selected from Q.

In some embodiments, A is 5-10 membered heteroaryl optionally substituted with 1, 2, 3, 4, or 5 substituents independently selected from Q.

In some embodiments, A is selected from pyridinyl, thienyl, thiazolyl, and pyrazolyl, each optionally substituted with 1, 2, 3, 4, or 5 substituents independently selected from Q.

In some embodiments, A is $C_{3-7}$ cycloalkyl optionally substituted with 1, 2, 3, 4, or 5 substituents independently selected from Q.

In some embodiments, A is cyclohexyl or cyclopropyl.

In some embodiments, Q is independently selected from $Cy^1$, halo, $C_{2-6}$ alkynyl, $C_{1-6}$ haloalkyl, CN, and $OR^{a1}$.

In some embodiments, Q is independently selected from F, trifluoromethyl, methoxy, CN, acetylene, methylpyrazolyl, thienyl, pyridinyl, and pyrimidinyl.

In some embodiments, $R^4$, $R^5$, and $R^6$ are each H.
In some embodiments, $R^7$ is methyl, ethyl, or isobutyl.
In some embodiments, $R^7$ is methyl
In some embodiments, n is 1.
In some embodiments, n is 0.
In some embodiments,
X is N or CH;
Y is N or CH;
Z is N or CH, provided at least two of X, Y, and Z are CH;
$R^1$ is H, F, Cl, Br, CN, methyl, methoxymethyl, ethoxymethyl, n-propyloxymethyl, isopropyloxymethyl, cyclobutyloxymethyl, cyclopropylmethyloxymethyl, methylthiomethyl, ethylthiomethyl, phenyl, thienyl, pyridinyl, methylpyrazolyl, thiazolyl, naphthyl, pyrimidinyl, fluoropyridinyl, methoxypyridinyl, methylaminocarbonylpyridinyl, or hydroxymethylbutynyl;
$R^2$ is H or methyl;
$R^3$ is H or methyl;
$R^7$ is methyl;

A is phenyl, pyridinyl, thienyl, thiazolyl, pyrazolyl, cyclohexyl, or cyclopropyl, each optionally substituted with 1, 2, or 3 substituents independently selected from F, trifluoromethyl, methoxy, CN, acetylene, methylpyrazolyl, thienyl, pyridinyl, and pyrimidinyl; and n is 0 or 1.

In some embodiments, the compounds of the invention have Formula IIa or IIb:

In some embodiments, the compounds of the invention have Formula III:

In some embodiments, the compounds of the invention have Formula IV:

In some embodiments, the compounds of the invention have Formula V:

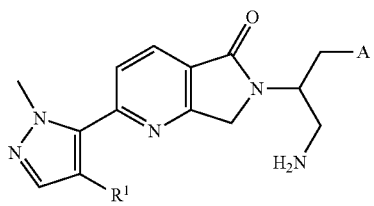

V

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. A linking alkyl group is referred to herein as "alkylene."

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, "halo" or "halogen", employed alone or in combination with other terms, includes fluoro, chloro, bromo, and iodo.

As used herein, the term "$C_{n-m}$ haloalkyl" refers to a $C_{n-m}$ alkyl group having up to {2(n to m)+1} halogen atoms which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, the term "$C_{n-m}$ alkoxy" refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms.

As used herein, the term "$C_{n-m}$ haloalkoxy" refers to a group of formula —O-haloalkyl, wherein the alkyl group has n to m carbons. Example alkoxy groups include trifluoromethoxy and the like. In some embodiments, the haloalkoxy group has 1 to 6, 1 to 4, or 1 to 3 carbon atoms.

As used herein, "$C_{n-m}$ aryl", employed alone or in combination with other terms, refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like, wherein the aryl group has n to m ring carbons. In some embodiments, aryl groups have from 6 to about 20 carbon atoms, from 6 to about 15 carbon atoms, or from 6 to about 10 carbon atoms. In some embodiments, the aryl group is phenyl.

As used herein, "heteroaryl", employed alone or in combination with other terms, refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl group having five ring atoms wherein one or more (e.g., 1, 2, or 3) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl group having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "$C_{n-m}$ cycloalkyl", employed alone or in combination with other terms, refers to a non-aromatic cyclic hydrocarbon including cyclized alkyl and alkenyl groups, and which has n to m ring member carbon atoms. Cycloalkyl groups can include mono- or polycyclic (e.g., having 2, 3 or 4 fused rings) groups and spirocycles. Cycloalkyl groups can have 3, 4, 5, 6, or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, the term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members or 4-6 ring members. Included in heterocycloalkyl are monocyclic 4-, 5-, 6-, and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2, or 3 heteroatoms independently selected from nitrogen, sulfur and oxygen. Examples of heterocycloalkyl groups include azetidine, pyrrolidine, piperidine, piperazine, morpholine, thiomorpholine, pyran, and the like. Ring-forming carbon atoms and heteroatoms of a heterocycloalkyl group can be optionally substituted by oxo or sulfido (e.g., C(O), S(O), C(S), or S(O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

As used herein, "$C_{n-m}$ aryl-$C_{n-m}$ alkyl" refers to a $C_{n-m}$ alkyl group substituted by one $C_{n-m}$ aryl group. In some embodiments, the $C_{n-m}$ aryl-$C_{n-m}$ alkyl group is benzyl.

As used herein, "5-10 membered heteroaryl-$C_{1-3}$ alkyl" refers to a $C_{1-3}$ alkyl group substituted by one 5-10 membered heteroaryl group. An example is pyridylmethyl.

As used herein, "$C_{3-7}$ cycloalkyl-$C_{1-3}$ alkyl" refers to a $C_{1-3}$ alkyl group substituted by one $C_{3-7}$ cycloalkyl group. An example is cyclopentylmethyl.

As used herein, "4-10 membered heterocycloalkyl-$C_{1-3}$ alkyl" refers to a $C_{1-3}$ alkyl group substituted by one 4-10 membered heterocycloalkyl group. An example is piperidinylmethyl.

At certain places, the definitions or embodiments refer to specific rings (e.g., an azetidine ring, a pyridine ring, etc.). Unless otherwise indicated, these rings can be attached any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

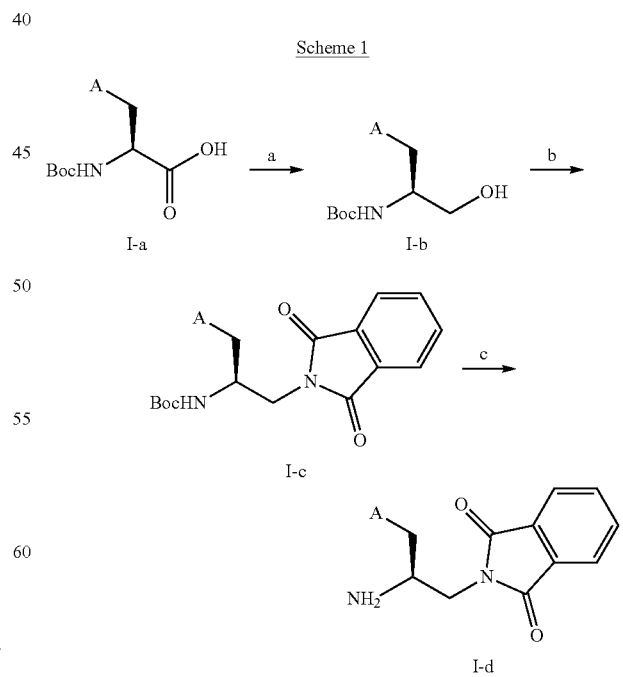

Scheme 1 Reagents: (a) BH$_3$/THF/rt; (b) phthalimide/PPh$_3$/DEAD/THF/rt; (c) 4M HCl/dioxane/THF The α-amino carboxylic acid (I-a, A is aryl, heteroaryl, or cycloalkyl) can be converted to the α-amino alcohol (I-b) by using reducing agents such as BH₃ and LAH. The α-amino alcohol (I-b) can be reacted under Mistsunobu conditions to provide the protected diamine (I-c). Methods and reaction conditions for Mitsunobo transformations are discussed in *Synthesis* 1981, 1-28. Selective deprotection of the Boc group of (I-c) can be carried out using strong acids such as 4 M HCl dioxane or TFA in a polar solvent such as methanol or DCM to afford amine (I-d). Many different protecting groups are available to one skilled in the art and can be used here as long as they do not interfere with the transformations. Methods for the protection of amines are described in standard reference volumes, such as Wuts and Greene, supra.

in a water-containing ethereal solvents such as dioxane, THF or DME. Methods for palladium-mediated coupling are described in standard reference volumes, such as Schlosser, ed. *Organometallics in Synthesis*, John Wiley & Sons Ltd., New York, N.Y., 2002. Basic treatment of II-c with hydrazine to remove the phthalimide protecting group can produce amine (II-d).

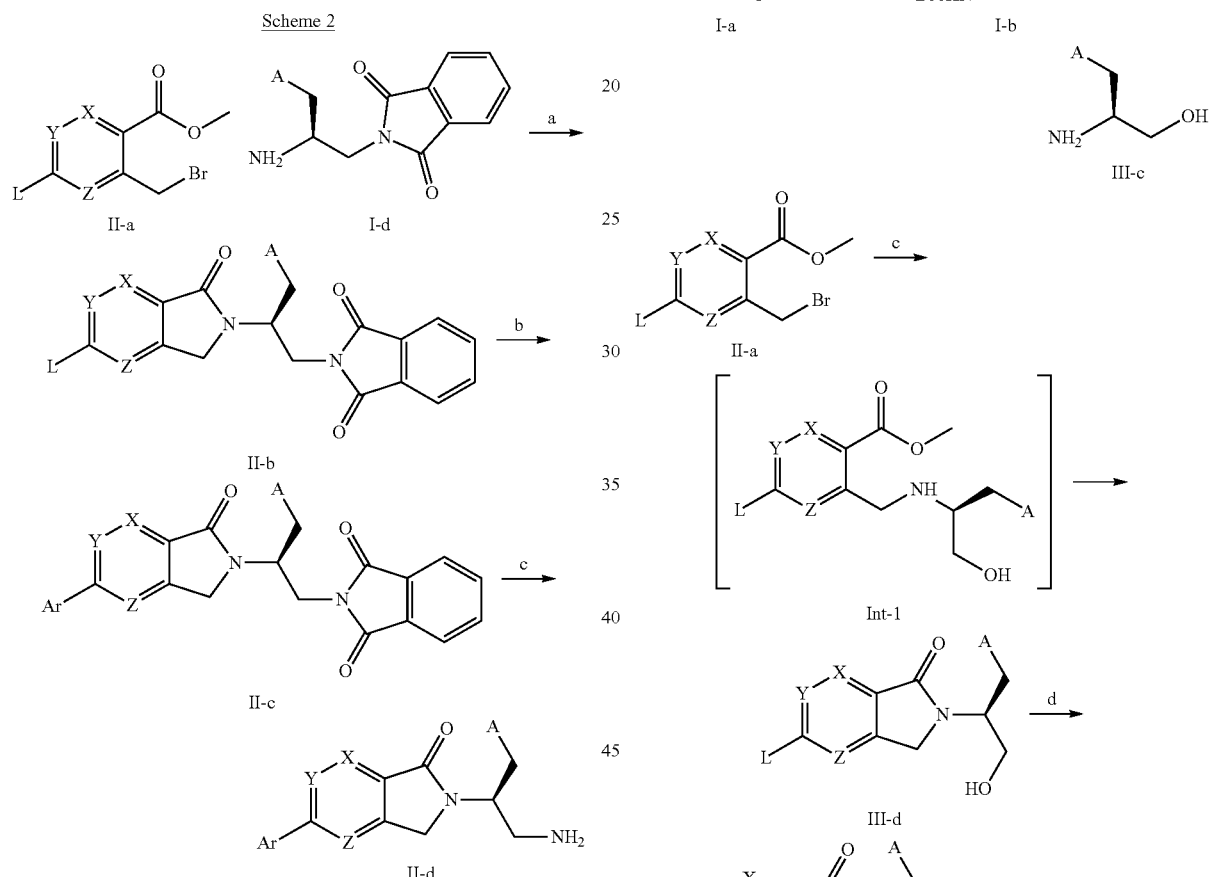

Scheme 2 Reagents: (a) DIPEA/1-butanol/140° C./microwave; (b) arylboronic acid, pinacol ester/bis(tri-t-butylphophine)palladium/DIPEA/dioxane/H₂O/110° C.; (c) hydrazine/MeOH/THF/rt.

Intermolecular cyclization of ester (II-a, L=Cl or Br; X, Y, and Z are each nitrogen or carbon ring members as defined hereinthroughout) and amine (I-d) in a polar solvent such as 1-butanol or dioxane using an organic base such as DIPEA or TEA can provide di-substituted isoindolone or aza-isoindolone (II-b). High temperatures and/or microwave irradiation can facilitate the cyclization reaction. Halide (II-b) can be coupled with arylboronic acid pinacol ester using a Suzuki coupling procedure to form intermediate II-c (where Ar is the aromatic group in the arylboronic acid pinacol ester, such as a pyrazole group). Suzuki-like coupling typically runs using a palladium (0) catalyst such as Pd(PPh₃)₄ or bis(tri-t-butylphosphine)palladium (0) with an inorganic or organic base

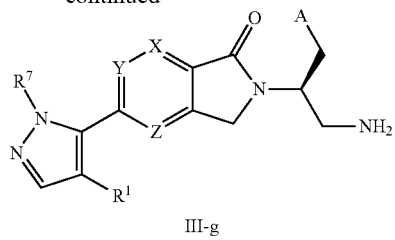

III-g

Scheme 3 Reagents: (a) BH₃/THF/rt; (b) 4M HCl/Dioxane/THF; (c) DIPEA/1-butanol/140° C./microwave; (d) phthalimide/PPh₃/DEAD/THF/rt; (e) 4-substituted-1-(C₁₋₃ alkyl)-5-(4,4,5,5-tetramethyl-1,3,2-dioxaborolan-2-yl)-1H-pryrazole/bis(tri-t-butylphosphine)palladium/DIPEA/dioxane/H₂O/110° C.; (f) hydrazine/MeOH/THF.

The α-amino carboxylic acid (I-a) can be easily converted to α-amino alcohol (III-c) by using reducing agents such as BH₃ and LAH, followed by acidic treatment of I-b with HCl or TFA to remove the Boc protective group. Intermolecular halor-replacement of ester (II-a, L=Cl or Br) with α-amino alcohol (III-c) in a polar solvent such as 1-butanol using an organic base such as DIPEA can result in the intermediate (Int-1) which undergoes an intramolecular cyclization to produce the isoindolone or aza-isoindolone (III-d). The Br-replacement proceeds well under mild condition such as room temperature. The cyclization reaction can benefit from high temperatures and microwave irradiation. The alcohol (III-d) can be reacted under Mistsunobu conditions to provide the phthalimide protected amine (III-e). Halide (III-e) can be coupled with 4-substituted-1-methyl-5-(4,4,5,5-tetramethyl-1,3,2-dioxaborolan-2-yl)-1H-pyrazole using Suzuki coupling procedures. Basic treatment of III-f with hydrazine to remove the phthalimide protecting group can produce amine (III-g).

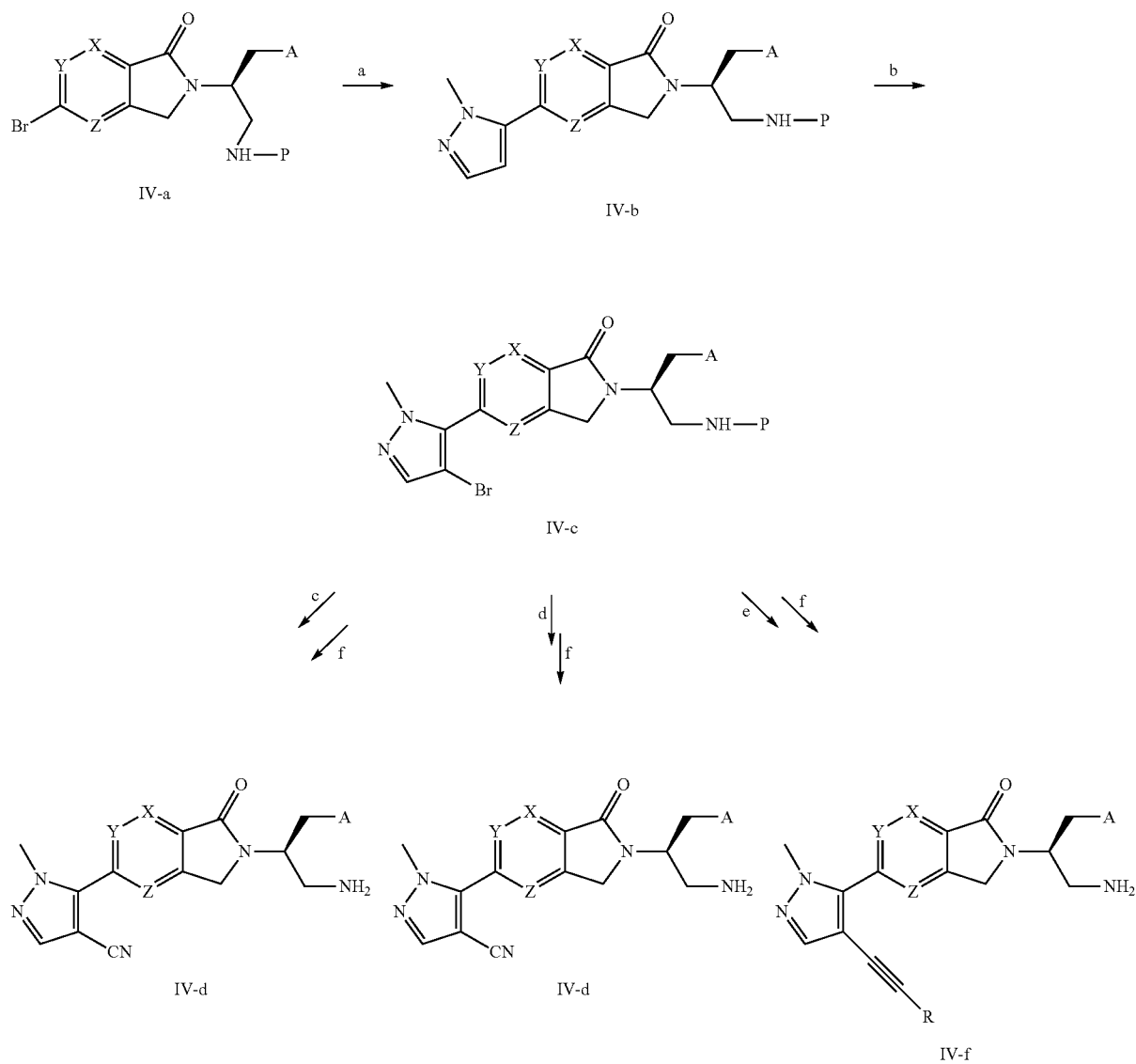

Scheme 4 Reagents: (a) 1-methyl-1H-pyrazole-5-boronic acid pinacol ester/bis(tri-t-butylphosphine)palladium/DIPEA/diozane/H₂O; (b) NBS/THF; (c) Zn(CN)₂/Pd(PPh₃)₄/NMPD/190° C.; (d) arylbornoic acid/bis(tri-t-butylphosphine)palladium/DIPEA/dioxane/H₂O/110 °C.; (e) HC≡CR /CuI/Pd(PPh₃)₂Cl₂/DIPEA/65° C.; (f) hydrazine/MeOH/THF Bromide (IV-a, P is an amino protecting group) can be coupled with 1-methyl-5-(4,4,5,5-tetramethyl-1,3,2-dioxaborolan-2-yl)-1H-pyrazole using Suzuki coupling procedures. The resulting compound (IV-b) can be brominated using NBS to form bromide (IV-c). Bromide (IV-c) can then be reacted with a variety of arylboronic acids (Ar—B(OH)$_2$ where Ar is an aromatic moiety) using bis(tri-t-butylphosphine)palladium as catalyst, followed by basic treatment with hydrazine to remove the protecting group, thereby generating a variety of aryl substituted compounds (IV-e). Bromide (IV-c) can also be reacted with zinc cyanide using tetra(triphenylphosphine)palladium (0) as catalyst, followed by basic treatment with hydrazine to remove phthalimide protecting group, to generate the cyano substituted compound (IV-d). Bromide (IV-c) can also be reacted with a variety of alkynes using a Sanagoshia coupling procedure, followed by basic treatment with hydrazine to remove phthalimide protecting group, to generate a variety of alkynyl substituted compounds (IV-f).

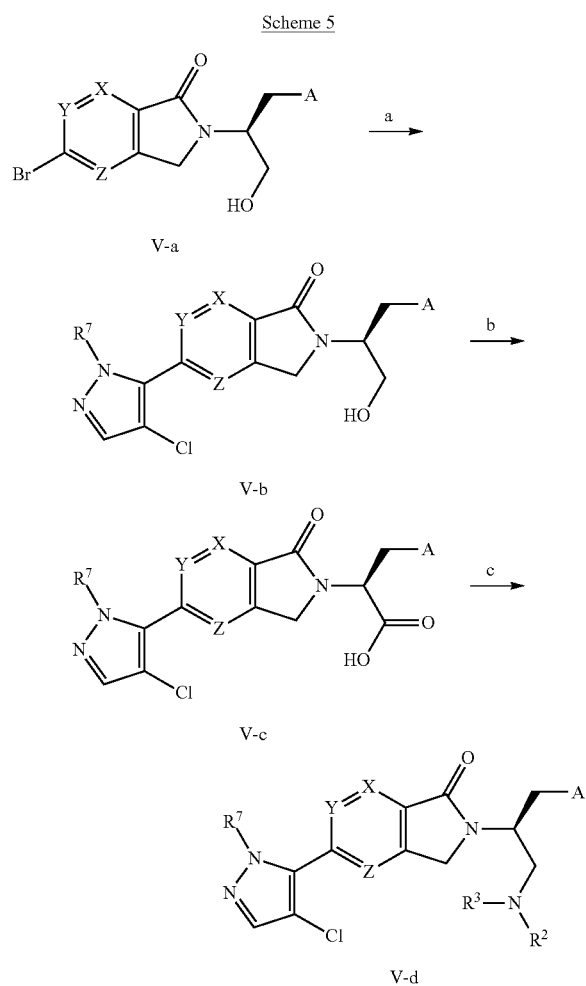

Scheme 5 Reagents: (a) 4-chloro-1-(C$_{1-3}$ alkyl)-1H-pyrazole-5-boronic acid pinacol ester/bis(tri-t-butylphosphine)palladium/DIPEA/dioxane/H$_2$O; (b) Dess-Martin periodinane/DCM/rt; (c) NHR$_1$R$_2$/NaBH(OAc)$_3$/THF.

Bromide (V-a) can be reacted with 4-chloro-1-methyl-1H-pyrazole-5-boronic acid pinacol ester using Suzuki coupling procedures. The resulting alcohol (V-b) can be oxidized by Dess-Martin periodinane to generate the aldehyde (V-c), which can be reacted with a variety of amines to produce the reductive amination products (V-d).

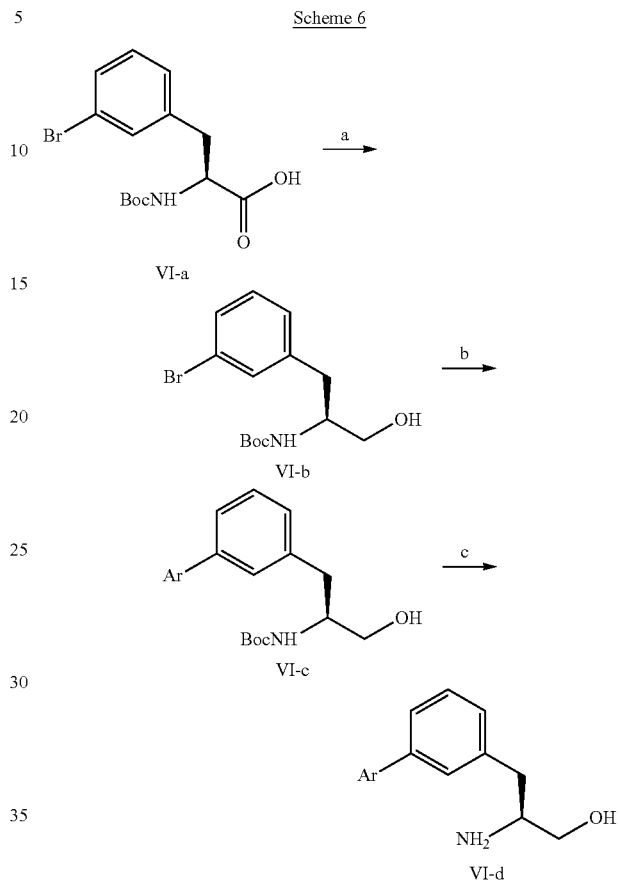

Scheme 6 Reagents: (a) BH$_3$/THF/rt; (b) Arylboronic acid/Pd(PPh$_3$)$_4$/Na$_2$CO$_3$/Dioxane/H$_2$O; (c) 4M HCl/Dioxane/THF α-Amino carboxylic acid (VI-a) can be easily converted to α-amino alcohol (VI-b) by using reducing agents such as BH$_3$ and LAH. The resulting bromide (VI-b) can be reacted with a variety of aryl boronic acids (Ar—B(OH)$_2$ where Ar is an aromatic moiety) under Suzuki coupling conditions to provide a variety of the biaryl products (VI-c). Acidic treatment of VI-c with strong acids such as 4 M HCl dioxane or TFA in polar solvents such as methanol or DCM to remove Boc-protecting group can afford/the α-amino alcohol (VI-d).

Utility

Compounds of the invention can inhibit the activity of one or more members of the Akt kinase family and are, thus, useful in treating diseases and disorders associated with dysregulation of Akt signaling or dysregulation of a signaling pathway in which Akt plays a role, such as the PI3K/PTEN/Akt/mTOR pathway.

The compounds of the invention can inhibit one or more of Akt1, Akt2, and Akt3. In some embodiments the compounds are selective for one Akt over another. By "selective" is meant that the compound binds to or inhibits an Akt kinase with greater affinity or potency, respectively, compared to a reference enzyme, such as another Akt kinase. For example, the compounds can be selective for Akt1 over Akt2 and Akt2, selective for Akt2 over Akt1 and Akt3, or selective for Akt3 over Akt1 and Akt2. In some embodiments, the compounds inhibit all of the Akt family members (e.g., Akt1, Akt2, and Akt3). In some embodiments, the compounds can be selective for Akt over other kinases such as receptor and non-receptor Ser/Thr kinases such as TGF-βR, PKA, PKG, PKC, CaM-kinase, phosphorylase kinase, MEKK, ERK, MAPK, and mTOR; receptor Tyr kinases such as EGFR, HER2, HER3, HER4, INS-R, IGF-1R, IR-R, PDGFαR, PDGFIβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK, or ABL. In general, selectivity can be at least about 5-fold, at least about 10-fold, at least about 20-fold, at least about 50-fold, at least about 100-fold, at least about 200-fold, at least about 500-fold or at least about 1000-fold.

Another aspect of the present invention pertains to methods of treating an Akt kinase-associated disease or disorder in an individual (e.g., patient) by administering to the individual in need of such treatment a therapeutically effective amount or dose of a compound of the present invention or a pharmaceutical composition thereof. An Akt kinase-associated disease can include any disease, disorder or condition that is directly or indirectly linked to expression or activity of the Akt kinase, including overexpression and/or abnormal activity levels. Abnormal activity levels can be determined by comparing activity level in normal, healthy tissue or cells with activity level in diseased cells. An Akt kinase-associated disease can also include any disease, disorder or condition that can be prevented, ameliorated, inhibited or cured by modulating Akt kinase activity. In some embodiments, the disease is characterized by the abnormal activity or expression (e.g., overexpression) of one or more Akt1, Akt2, and Akt3. In some embodiments, the disease is characterized by mutant Akt1, Akt2, or Akt3.

Examples of Akt kinase-associated diseases include cancer such as ovarian cancer, pancreatic cancer, breast cancer, prostate cancer, colon cancer, brain cancer, lung cancer, head and neck cancer, melanoma, gastric cancer, hepatocellular carcinoma (HCC), endometrial cancer, renal cancer, leukemia (e.g., chronic lymphocyte leukemia (CLL)), and lymphoma (e.g., Mantle cell lymphoma (MCL), diffuse large B-cell lymphoma (DLBCL), etc.).

The compounds of the invention can also be useful in the treatment of Cowden Syndome, or the symptoms thereof.

As used herein, the terms "individual" or "patient," used interchangeably, refer to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing the disease; for example, preventing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it would be useful to combine different kinase inhibitors, exhibiting different preferences in the kinases which they modulate the activities of, to treat such conditions. This approach could prove highly efficient by targeting multiple signaling pathways, thereby reducing the likelihood of drug-resistance arising in a cell, and reducing the toxicity of treatments.

Accordingly, the Akt inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK, B-Raf, and Pim. Additionally, the Akt inhibitors of the invention can be combined with inhibitors of kinases associated with the same pathway as Akt, such as PI3K, and mTOR kinases.

The Akt inhibitors of the present invention can further be used in combination with one or more anti-cancer drugs, such as a chemotherapeutics. Example chemotherapeutics include proteosome inhibitors (e.g., bortezomib), thalidomide, revlimid, cisplatin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, melphalan, doxorubicin, vincristine, carmustine, and the like The Akt inhibitors of the present invention can further be used in combination with one or more anti-inflammatory agents, steroids, immunosuppressants, or therapeutic antibodies.

When more than one pharmaceutical agent is administered to a patient, they can be administered simultaneously, sequentially, or combination thereof (e.g., for more than two agents).

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Akt in tissue samples, including human, and for identifying Akt ligands by inhibition binding of a labeled compound. Accordingly, the present invention includes Akt assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro Akt labeling and competition assays, compounds that incorporate $^3$H, $^{14}$C, $^{82}$Br, $^{125}$I, $^{131}$I, $^{35}$S or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms. Synthetic methods for incorporating radio-isotopes into organic compounds arel known in the art.

Specifically, a labeled compound of the invention can be used in a screening assay to identify and/or evaluate compounds. For example, a newly synthesized or identified compound (i.e., test compound) which is labeled can be evaluated for its ability to bind an Akt by monitoring its concentration variation when contacting with the Akt, through tracking of the labeling. For example, a test compound (labeled) can be evaluated for its ability to reduce binding of another compound which is known to bind to an Akt (i.e., standard compound). Accordingly, the ability of a test compound to compete with the standard compound for binding to the Akt directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of Akt-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Akt inhibitors according to at least one assay described infra.

EXAMPLES

Experimental procedures for compounds of the invention are provided below. Open Access Prep LC-MS Purification of some of the compounds prepared was performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions set out below in Methods A and B.

Unless otherwise indicated, the example compounds were purified by preparative HPLC using acidic conditions (method A) and were obtained as a TFA salt, or using basic conditions (method B) and were obtained as a free base.

Method A:

Column: Waters Sun Fire C18, 5 μm particle size, 30×100 mm;

Mobile phase: water (0.1% TFA)/acetonitrile

Flow rate: 60 mL/min

Gradient: 5 min or 12 min from 5% acetonitrile/95% water to 100% acetonitrile

Method B:

Column: Waters X Bridge C18, 5 μm particle size, 30×100 mm;

Mobile phase: water (0.15% $NH_4OH$)/acetonitrile

Flow rate: 60 mL/min

Gradient: 5 min or 12 min from 5% acetonitrile/95% water to 100% acetonitrile

The example compounds and intermediates below containing one or more chiral centers were obtained in enantiomerically pure form or as scalemic or racemic mixtures, unless otherwise specified.

Intermediate 1

4-Chloro-1-methyl-5-(4,4,5,5-tetramethyl-1,3,2-dioxaborolan-2-yl)-1H-pyrazole

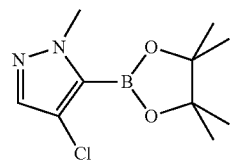 [SMILES: Cn1ncc(Cl)c1B1OC(C)(C)C(C)(C)O1]

A solution of 1-methyl-5-(4,4,5,5-tetramethyl-1,3,2-dioxaborolan-2-yl)-1H-pyrazole (1.00 g, 4.81 mmol) and N-chlorosuccinimide (0.671 g, 5.05 mmol) in tetrahydrofuran (10 mL, 100 mmol) was stirred at 70° C. for 2 hrs. The reaction mixture was concentrated under reduced pressure and the residue was purified by combi-flash chromatography and eluted with EtOAc/hexane (10-80%). The purification afforded 1.08 g (78% yield) of the desired product as white solid.

Intermediate 2

1,4-dimethyl-5-(4,4,5,5-tetramethyl-1,3,2-dioxaborolan-2-yl)-1H-pyrazole

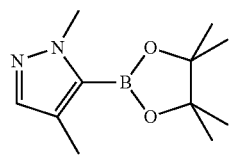 [SMILES: Cc1cnn(C)c1B1OC(C)(C)C(C)(C)O1]

A solution of 1,4-dimethyl-1H-pyrazole (480.0 mg, 4.993 mol) in tetrahydrofuran (20 mL, 300 mmol) at 0° C. was added 1.6 M n-butyllithium in hexane (4.7 mL, 7.5 mmol). The solution was stirred at room temperature for 1 h and then cooled to −78° C. To the solution was added 2-isopropoxy-4,4,5,5-tetramethyl-1,3,2-dioxaborolane (1.63 mL, 7.99 mmol). The reaction mixture was stirred at −78° C. for 0.5 h, then warmed up to 0° C. (taking 0.5 h). The reaction was quenched with brine and extracted with EtOAc (3×). The combined organic phases were washed with brine, dried over $Na_2SO_4$, and concentrated under reduced pressure. The residue was purified by combi-flash chromatography and eluted with EtOAc/hexane (0-60%). The purification gave 142 mg of product as white solid.

Intermediate 3

4-(methoxymethyl)-1-methyl-5-(4,4,5,5-tetramethyl-1,3,2-dioxaborolan-2-yl)-1H-pyrazole

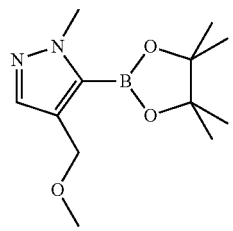 [SMILES: COCc1cnn(C)c1B1OC(C)(C)C(C)(C)O1]

Step A: (1-methyl-1,1-pyrazol-4-yl)methanol

To a solution of 1-methyl-1H-pyrazole-4-carbaldehyde (0.500 g, 4.54 mmol) in methanol (10 mL, 200 mmol) at 0° C. was added sodium tetrahydroboride (0.515 g, 13.6 mmol). The reaction was stirred at room temperature for 1 h, and then quenched with brine, and extracted with ethyl acetate (EtOAc) (3×). The combined organic phases were washed with water, brine, dried over $Na_2SO_4$, and concentrated to give 0.308 g (60.5% yield) of the final product as colorless oil, which was used directly for the next step without further purification. LC/MS found: 113.1 $(M+1)^+$.

Step B: 4-(methoxymethyl)-1-methyl-1,1-pyrazole

To a suspension of sodium hydride (0.128 g, 3.21 mmol) in tetrahydrofuran (5 mL, 60 mmol) at 0° C. was added (1-methyl-1H-pyrazol-4-yl)methanol (0.300 g, 2.68 mmol) in tetrahydrofuran (2 mL, 20 mmol). The reaction was stirred at room temperature for 1 h, and then cooled down with ice bath. Methyl iodide (0.83 mL, 13 mmol) was added. The reaction was stirred at room temperature overnight. The reaction mixture was quenched with brine and extracted with EtOAc (3×). The combined organic phases were washed with water, brine, then dried over $Na_2SO_4$, and concentrated under reduced pressure to give 261 mg (77.2% yield) of the desired product as colorless oil, which was directly used for the next reaction. LC/MS found: 127.2 $(M+1)^+$.

Step C: 4-(methoxymethyl)-1-methyl-5-(4,4,5,5-tetramethyl-1,3,2-dioxaborolan-2-yl)-1H-pyrazole To a solution of 4-(methoxymethyl)-1-methyl-1H-pyrazole (261.0 mg, 2.069 mmol) in tetrahydrofuran (5 mL, 60 mmol) at 0° C. was added 1.6 M n-butyllithium in hexane (3.88 mL, 6.21 mmol). The solution was stirred at room temperature for 1 h and cooled to −78° C. To the solution was added 2-isopropoxy-4,4,5,5-tetramethyl-1,3,2-dioxaborolane (0.46 mL, 2.3 mmol). The reaction was stirred at −78° C. for 0.5 h and then warmed up to 0° C. (taking 0.5 h). The reaction mixture was quenched with brine, adjusted to pH=6-7 with 1 N HCl aqueous solution, and extracted with EtOAc (3×). The combined organic phases were washed with brine, dried over $Na_2SO_4$, and concentrated to give brown oil, which was purified by combi-flash chromatography. LC/MS found: 253.1 $(M+1)^+$.

Intermediate 4

4-(ethoxymethyl)-1-methyl-5-(4,4,5,5-tetramethyl-1,3,2-dioxaborolan-2-yl)-1H-pyrazole

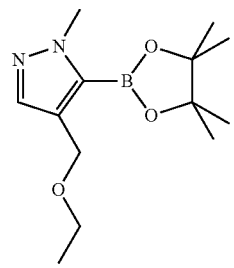 [SMILES: CCOCc1cnn(C)c1B1OC(C)(C)C(C)(C)O1]

The title compound was prepared substantially as described for Intermediate 3, except substituting iodoethane for iodomethane. LC-MS found: 267.2 $(M+H)^+$.

Intermediate 5

4-(2-propoxymethyl)-1-methyl-5-(4,4,5,5-tetramethyl-1,3,2-dioxaborolan-2-yl)-1H-pyrazole

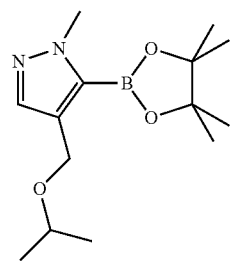 [SMILES: CC(C)OCc1cnn(C)c1B1OC(C)(C)C(C)(C)O1]

Step A: 4-(chloromethyl)-1-methyl-1,1-pyrazole

To a solution of (1-methyl-1H-pyrazol-4-yl)methanol (1.29 g, 11.5 mmol) (prepared from Intermediate 3 Step A) in methylene chloride (4 mL) at 0° C. was added thionyl chloride (4 mL, 50 mmol). The solution was stirred at room temperature for 3 h. Concentration under reduced pressure gave 1.50 g (100% yield) of the desired product as white solid, which was used for the next step directly.

Step B: 4-(isopropoxymethyl)-1-methyl-1,1-pyrazole

To a suspension of sodium hydride (0.689 g, 17.2 mmol) in tetrahydrofuran (20 mL) at 0° C. was added isopropyl alcohol (1.06 mL, 13.8 mmol). The mixture was stirred at room temperature for 1 h. After cooling with an ice bath, the mixture was added to a solution of 4-(chloromethyl)-1-methyl-1H-pyrazole (1.50 g, 11.5 mmol) in N,N-dimethylformamide (20 mL). The reaction was stirred at room temperature overnight. The reaction mixture was cooled down with an ice bath, then quenched with brine, and extracted with EtOAc (2×). The combined organic phases were washed with water, brine, dried over $Na_2SO_4$, filtered and concentrated. The residue was purified by combi-flash chromatography eluted with EtOAc/hexane (50-100%). The purification gave 1.35 g (76.2% yield) of the product as white solid. LC/MS found: 155.0 $(M+1)^+$

Step C: 4-(isopropoxymethyl)-1-methyl-5-(4,4,5,5-tetramethyl-1,3,2-dioxaborolan-2-yl)-1,1-pyrazole To a solution of 4-(isopropoxymethyl)-1-methyl-1H-pyrazole (1.35 g, 8.75 mmol) in tetrahydrofuran (10 mL) at 0° C. was added 1.6 M n-butyllithium in hexane (19.2 mL, 30.6 mmol). The solution was stirred at room temperature for 1 h and then cooled down to −78° C. To the resulting solution was added 2-isopropoxy-4,4,5,5-tetramethyl-1,3,2-dioxaborolane (2.1 mL, 10.0 mmol). The reaction was continued at −78° C. for 0.5 h, then warmed up to 0° C. (taking about 0.5 h). The reaction mixture was quenched with brine, adjusted to pH=6-7 with 1 N HCl aqueous solution, and extracted with EtOAc (2×). The combined organic phases were washed with brine and dried over $Na_2SO_4$. Concentration under reduced pressure gave a brown oil which was purified by combi-flash chromatography to give 2.24 g (91.3% yield) of the desired product. LC-MS found: 281.0 $(M+H)^+$.

Intermediate 6

4-(1-propoxymethyl)-1-methyl-5-(4,4,5,5-tetramethyl-1,3,2-dioxaborolan-2-yl)-1H-pyrazole

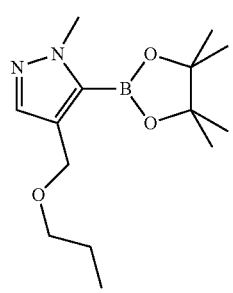 [SMILES: CCCOCc1cnn(C)c1B1OC(C)(C)C(C)(C)O1]

The title compound was prepared substantially as described for Intermediate 5, except substituting 1-propanol for 2-propanol. LC-MS found: 281.0 $(M+H)^+$.

Intermediate 7

4-(cyclobutoxymethyl)-1-methyl-5-(4,4,5,5-tetramethyl-1,3,2-dioxaborolan-2-yl)-1H-pyrazole

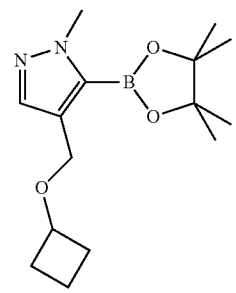

The title compound was prepared substantially as described for Intermediate 5, except substituting cyclobutanol for 2-propanol. LC-MS found: 293.1 $(M+H)^+$.

Intermediate 8

4-(cyclopropylmethoxymethyl)-1-methyl-5-(4,4,5,5-tetramethyl-1,3,2-dioxaborolan-2-yl)-1H-pyrazole

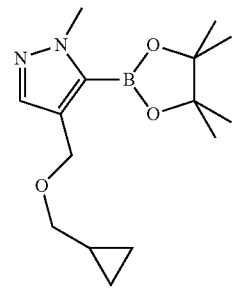 [SMILES: Cn1ncc(COCC2CC2)c1B1OC(C)(C)C(C)(C)O1]

The title compound was prepared substantially as described for Intermediate 5, except substituting cyclopropyl carbinol for 2-propanol. LC-MS found: 293.0 $(M+H)^+$.

Intermediate 9

4-(2-methoxyethyl)-1-methyl-5-(4,4,5,5-tetramethyl-1,3,2-dioxaborolan-2-yl)-1H-pyrazole

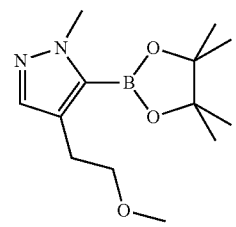 [SMILES: COCCc1cnn(C)c1B1OC(C)(C)C(C)(C)O1]

Step A: 4-(2-methoxyethyl)-1-methyl-1,1-pyrazole

To a suspension of sodium hydride (0.476 g, 11.9 mmol) in N,N-dimethylformamide (10 mL) at 0° C. was added 2-(1-methyl-1H-pyrazol-4-yl)ethanol (1.00 g, 7.93 mmol). The reaction was stirred at room temperature for 1 h. After cooling down with an ice bath, the reaction mixture was added to methyl iodide (2.5 mL, 40 mmol). The reaction was stirred at room temperature overnight. The reaction mixture was quenched with brine and extracted with EtOAc (2×). The combined organic phases were washed with water, brine, dried over $Na_2SO_4$, and concentrated under reduced pressure to give a brown residue which was purified by combi-flash chromatography eluted with EtOAC/hexane (50-100%). The purification gave 0.401 g (36.1% yield) of the desired product as colorless oil. LC/MS found: 141.1 (M+1).

Step B: 4-(2-methoxyethyl)-1-methyl-5-(4,4,5,5-tetramethyl-1,3,2-dioxaborolan-2-yl)-1H-pyrazole To a solution of 4-(2-methoxyethyl)-1-methyl-1H-pyrazole (0.400 g, 2.85 mmol) in tetrahydrofuran (10 mL) at 0° C. was added 1.6 M n-butyllithium in hexane (6.24 mL, 9.99 mmol). The solution was stirred at room temperature for 1 h and then cooled down to −78° C. To the solution was added 2-isopropoxy-4,4,5,5-tetramethyl-1,3,2-dioxaborolane (0.70 mL, 3.4 mmol). The reaction was continued at −78° C. for 0.5 h, then warmed up to 0° C. (taking 0.5 h). The reaction mixture was quenched with brine, adjusted to pH=6-7 with 1 N HCl aqueous solution, and extracted with EtOAc (2×). The combined organic phases were washed with brine, dried over $Na_2SO_4$, and concentrated to give a brown oil which was further purified to provide 0.33 g (43% yield) of the desired product. LC-MS found: 267.1 (M+H)+.

Intermediate 10

4-[(ethylthio)methyl]-1-methyl-5-(4,4,5,5-tetramethyl-1,3,2-dioxaborolan-2-yl)-1H-pyrazole

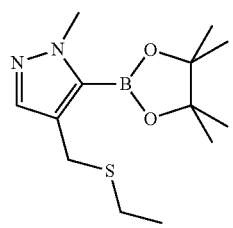 [SMILES: CCSCc1cnn(C)c1B1OC(C)(C)C(C)(C)O1]

Step A: 4-[(ethylthio)methyl]-1-methyl-1H-pyrazole

A mixture of 4-(chloromethyl)-1-methyl-1H-pyrazole (2.0 g, 15 mmol) (prepared according to Intermediate 5 Step A) and sodium ethanethiolate (2.6 g, 31 mmol) in N,N-dimethylformamide (20.0 mL) was stirred at room temperature overnight. The reaction mixture was quenched with brine and extracted with EtOAc (3×). The combined extracts were dried over $Na_2SO_4$, filtered and concentrated under reduced pressure to give an oil residue which was purified by combi-flash chromatography eluted with 20% EtOAc in hexane to give 1.9 g (79% yield) of the desired product. LC-MS found: 157.1 (M+H)+.

Step B: 4-[(ethylthio)methyl]-1-methyl-5-(4,4,5,5-tetramethyl-1,3,2-dioxaborolan-2-yl)-1H-pyrazole To a solution of 4-[(ethylthio)methyl]-1-methyl-1H-pyrazole (0.81 g, 5.2 mmol) in tetrahydrofuran (3.0 mL) at 0° C. was added 1.6 M n-butyllithium in hexane (6.3 mL, 10. mmol). The solution was stirred at room temperature for 1 h and then cooled down to −78° C. To the solution was added 2-isopropoxy-4,4,5,5-tetramethyl-1,3,2-dioxaborolane (2.06 mL, 10.1 mmol). The reaction was continued at −78° C. for 0.5 h, then warmed up to 0° C. (taking about 0.5 h). The reaction mixture was quenched with brine, adjusted to PH=6-7 with 1 N HCl aqueous solution, extracted with EtOAc (2×). The combined organic phases were washed with brine, dried over $Na_2SO_4$, and concentrated under reduced pressure to give one oil residue which was purified by combi-flash chromatography eluted with EtOAc/hexane (20-100%). The purification gave 1.2 g (86% yield) of the desired product as yellowish oil. LC-MS found: 283.1 (M+H)+.

Intermediate 11

4-[(methylthio)methyl]-1-methyl-5-(4,4,5,5-tetramethyl-1,3,2-dioxaborolan-2-yl)-1H-pyrazole

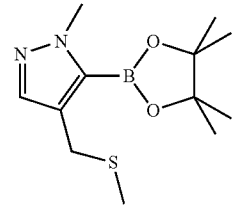 [SMILES: CSCc1cnn(C)c1B1OC(C)(C)C(C)(C)O1]

The title compound was prepared substantially as described for Intermediate 10, except substituting sodium methanethiolate for sodium ethanethiolate. LC-MS found: 269.0 (M+H)+.

Intermediate 12

(2S)-2-amino-3-(2-fluorophenyl)propan-1-ol

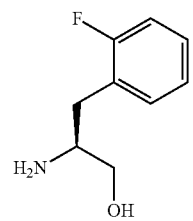 [SMILES: N[C@H](CO)Cc1ccccc1F]

To a solution of (2S)-2-amino-3-(2-fluorophenyl)propanoic acid (10.00 g, 54.59 mmol) in tetrahydrofuran (25 mL) with stirring was added 1.0 M borane-THF complex in THF (100.0 mL) (freshly opened) dropwise to keep the internal temperature around 0° C. After addition, the reaction mixture was stirred at room temperature for 3 hrs. Then the mixture was cooled with an ice-bath, quenched with AcOH:MeOH (1:5, 50 mL), and partitioned between saturated aqueous $NaHCO_3$ solution and dichloromethane (DCM). The organic phases were dried over sodium sulfate, filtered, and evaporated under vacuum to give an oil residue which was purified on prep. HPLC to give the purified desired product. LC-MS found: 170.1 (M+H)+.

Intermediate 13

(2S)-2-amino-3-(benzothien-3-yl)propan-1-ol

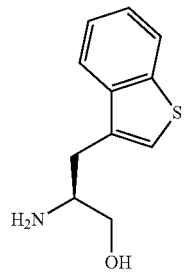 [SMILES: N[C@H](CO)Cc1csc2ccccc12]

The title compound was prepared substantially as described in Intermediate 12, except substituting (2S)-2-amino-3-(benzothien-3-yl)propanoic acid for (2S)-2-amino-3-(2-fluorophenyl)propanoic acid.

Intermediate 14

(2S)-2-amino-3-[3-(trifluoromethyl)phenyl]propan-1-ol

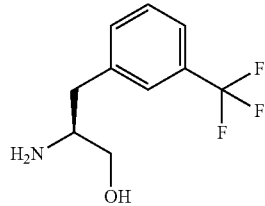 [SMILES: N[C@H](CO)Cc1cccc(C(F)(F)F)c1]

To a solution of (2S)-2-[(tert-butoxycarbonyl)amino]-3-[3-(trifluoromethyl)phenyl]-propanoic acid (Aldrich) (10.00 g, 30.00 mmol) in tetrahydrofuran (25 mL) with stirring, 1.0 M borane-THF complex in THF (100.0 mL, 100.0 mmol) (newly opened) was added dropwise to keep the internal temperature at 0° C. (release gas, about 15 min). After addition the reaction was stirred at room temperature (rt) for 6 hrs, cooled down with ice-bath, quenched with AcOH:MeOH (1:5, 50 mL), and partitioned between saturated aqueous NaHCO₃ and DCM, dried over sodium sulfate, filtered, and evaporated under reduced pressure to give an oil residue, which was purified by combi-flash chromatography to give the desired intermediate. LC-MS found: 320.1 (M+H)+.

The intermediate was dissolved in 4 N HCl dioxane solution (20 mL) and methanol (20 mL). The resulted solution was stirred at room temperature for 2 h. Direct evaporation under reduced pressure afforded the final product. LC-MS found: 220.1 (M+H)+.

Intermediate 15

(2S)-2-amino-3-(3-cyano-phenyl)propan-1-ol

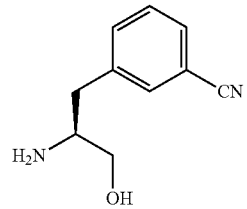 [SMILES: N#Cc1cccc(C[C@H](N)CO)c1]

Step A: tert-butyl[(1S)-1-(3-bromobenzyl)-2-hydroxyethyl]carbamate

To a solution of (2S)-3-(3-bromophenyl)-2-[(tert-butoxycarbonyl)amino]propanoic acid (Chem-Impex) (15 g, 44 mmol) in tetrahydrofuran (31 mL, 380 mmol) with stirring, 1.0 M borane-THF complex in THF (130 mL) was added dropwise to keep temperature at 0° C. (about 15 min). After addition the reaction mixture was stirred at room temperature for 1 h, cooled with an ice-bath, quenched with AcOH:MeOH (1:5, 70 mL), and partitioned between saturated aqueous NaHCO₃ solution and DCM, dried over sodium sulfate and evaporated under reduced pressure to give 13.2 g (92% yield) of the crude desired product, which was used in the next reaction with no further purification. LC-MS found: 330.1 (M+H)+.

Step B: (2S)-2-amino-3-(3-cyano-phenyl)propan-1-ol

To a solution of tert-butyl[(1S)-1-(3-bromobenzyl)-2-hydroxyethyl]carbamate (1.00 g, 3.03 mmol) in N,N-dimethylformamide (10.0 mL) was added zinc cyanide (0.533 g, 4.54 mmol) and tetrakis(triphenylphosphine)palladium(0) (350 mg, 0.30 mmol). The reaction was degassed by bubbling N₂ for 1 min. The reaction mixture was heated at 130° C. for 2 h. The crude was filtered and then purified by silica gel column chromatography (40 g column, 0 to 50% EtOAc in hexane) to give 0.488 g (58% yield) of the desired intermediate as off-white powder. LC-MS found: 177.1 (M−Boc+H)+.

The white intermediate was dissolved in methanol (2 mL) and 4 N HCl dioxane solution (2 mL, 8 mmol). The resulting mixture was stirred at room temperature for 2 h. Direct evaporation under vacuum afforded the desired final product. LC-MS found: 177.1 (M+H)+.

Intermediate 16

(2S)-2-amino-3-(4-cyano-phenyl)propan-1-ol

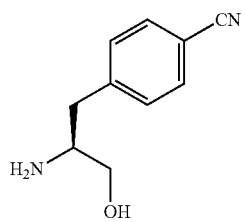 [SMILES: N#Cc1ccc(C[C@H](N)CO)cc1]

The title compound was prepared substantially as described in Intermediate 15, except substituting (2S)-3-(4-bromophenyl)-2-[(tert-butoxycarbonyl)amino]propanoic acid (Chem-Impex) for (2S)-3-(3-bromophenyl)-2-[(tert-butoxycarbonyl)amino]propanoic acid.

Intermediate 17

(2S)-2-amino-3-(2-methoxypyridin-4-yl)propan-1-ol

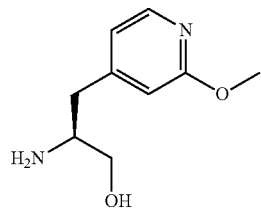

Step A: methyl (2S)-2-[(tert-butoxycarbonyl)amino]-3-(2-methoxypyridin-4-yl)propanoate Methyl (2S)-2-amino-3-(2-methoxypyridin-4-yl)propanoate[2.0]-hydrogen chloride (Netchem Product List) (2.0 g, 7.1 mmol) and di-tert-butyldicarbonate (1.7 g, 7.8 mmol) and sodium carbonate (1.6 g, 15 mmol) and water (20 mL) and acetone (20 mL) were mixed together and stirred at rt for 1 h. The solvent was removed under vacuum. Purification on combi-flash column (40 g silica gel, 0-25% MeOH in EtOAc) afforded 1.03 g (47% yield) of the desired product. LC-MS found: 311.0 (M+H)+.

Step B: (2S)-2-[(tert-butoxycarbonyl)amino]-3-(2-methoxypyridin-4-yl)propanoic acid Methyl (2S)-2-[(tert-butoxycarbonyl)amino]-3-(2-methoxypyridin-4-yl)propanoate (1.42 g, 4.58 mmol) was mixed with methanol (10.0 mL) and a solution of lithium hydroxide (0.66 g, 14 mmol) in water (5.0 mL). The mixture was stirred at rt for 1 h. The mixture was then acidified with 4 N HCl dioxane solution and condensed under vacuum directly to give the white solid mixture, which was used directly in the next step. LC-MS found: 297.1 (M+H)+.

Step C: tert-butyl {(1S)-2-hydroxy-1[(2-methoxypyridin-4-yl)methyl]ethyl}carbamate To a solution of (2S)-2-[(tert-butoxycarbonyl)amino]-3-(2-methoxypyridin-4-yl)propanoic acid (1.3 g, 4.4 mmol) in tetrahydrofuran (5.0 mL) with stirring, 1.0 M borane-THF complex in THF (13 mL) was added dropwise to keep the internal temperature at 0° C. (about 15 min). After addition, the mixture was stirred at rt for 3 h, cooled with an ice-bath, quenched with AcOH:MeOH (1:5, 5 mL), partitioned between saturated aqueous NaHCO3 and DCM, dried over Na2SO4, filtered, and evaporated under reduced pressure to give 0.5 g (40% yield) of the desired product. LC-MS found: 283.0 (M+H)+.

Step D: (2S)-2-amino-3-(2-methoxypyridin-4-yl)propan-1-ol

To a vial was added tert-butyl {(1S)-2-hydroxy-1-[(2-methoxypyridin-4-yl)methyl]ethyl}carbamate (0.50 g, 1.8 mmol) and methanol (2.0 mL) and 4.0 M hydrogen chloride in dioxane (5.0 mL, 20. mmol). The reaction was stirred at room temperature overnight. Direct evaporation under reduced pressure afforded the final compound. LC-MS found: 183.0 (M+H)+.

Intermediate 18

(2S)-2-amino-3-pyridin-3-ylpropan-1-ol

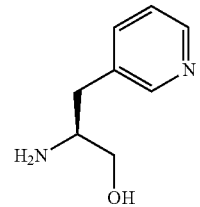

The title compound was prepared substantially as described in Intermediate 14, except substituting Boc-L-3-(3-pyridyl)-ananine (Matrix Scientific) for (2S)-2-[(tert-butoxycarbonyl)amino]-3-[3-(trifluoromethyl)phenyl]-propanoic acid.

Intermediate 19

(2S)-2-amino-3-pyridin-2-ylpropan-1-ol

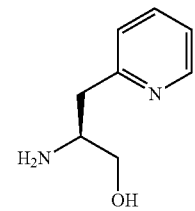 [SMILES: N[C@H](CO)Cc1ccccn1]

The title compound was prepared substantially as described in Intermediate 14, except substituting Boc-L-3-(2- pyridyl)-ananine (Matrix Scientific) for (2S)-2-[(tert-butoxycarbonyl)amino]-3-[3-(trifluoromethyl)phenyl]-propanoic acid.

Intermediate 20

(2S)-2-amino-3-(2-thienyl)propan-1-ol

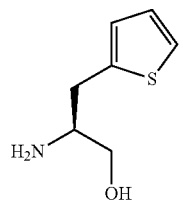

The title compound was prepared substantially as described in Intermediate 14, except substituting Boc-L-3-(2-thienyl)-ananine (Aldrich) for (2S)-2-[(tert-butoxycarbonyl)amino]-3-[3-(trifluoromethyl)phenyl]-propanoic acid.

Intermediate 21

(2S)-2-amino-3-(3-thienyl)propan-1-ol

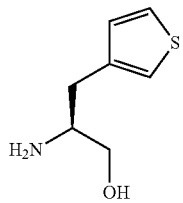

The title compound was prepared substantially as described in Intermediate 14, except substituting Boc-L-3-(3-thienyl)-ananine (3B Scientific Corporation Product List) for (2S)-2-[(tert-butoxycarbonyl)amino]-3-[3-(trifluoromethyl)phenyl]-propanoic acid.

Intermediate 22

(2S)-2-amino-3-(1,3-thiazol-4-yl)propan-1-ol

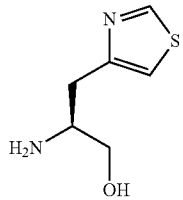

The title compound was prepared substantially as described in Intermediate 14, except substituting Boc-L-3-(4-thiazolyl)-ananine (3B Scientific Corporation Product List) for (2S)-2-[(tert-butoxycarbonyl)amino]-3-[3-(trifluoromethyl)phenyl]-propanoic acid.

Intermediate 23

(2S)-2-amino-3-[3-(1-methyl-1H-pyrazol-4-yl)phenyl]propan-1-ol

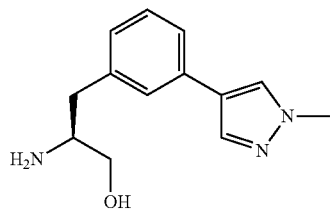 [SMILES: Cn1cc(-c2cccc(C[C@H](N)CO)c2)cn1]

Step A: tert-butyl {(1S)-2-hydroxy-1-[3-(1-methyl-1H-pyrazol-4-yl)benzyl]ethyl}carbamate To 0.7 M potassium carbonate in water was added tert-butyl[(1S)-1-(3-bromobenzyl)-2-hydroxyethyl]carbamate [prepared according to Intermediate 15, Step A] (1.00 g, 3.03 mmol) and 1-methyl-4-(4,4,5,5-tetramethyl-1,3,2-dioxaborolan-2-yl)-1H-pyrazole (0.82 g, 3.9 mmol) and 1,4-dioxane (26 mL, 340 mmol) and 2.0 M sodium carbonate in water (6.0 mL, 12 mmol). The mixture was flushed with nitrogen for 10 min. To the mixture was then added tetrakis(triphenylphosphine)palladium(0) (0.17 g, 0.15 mmol) and the mixture was heated at 100° C. for 30 min. The resulting mixture was purified on 40 g silica gel, 0-100% EtOAc in hexanes, and the pure fractions were combined, and solvent removed under vacuum to give 0.45 g of white solid. LC-MS found: 332.2 (m+1).

Step B: (2S)-2-amino-3-[3-(1-methyl-1H-pyrazol-4-yl)phenyl]propan-1-ol

The product of Step A (0.45 g, 1.4 mmol) was combined with methanol (2.0 mL, 49 mmol) and 4.0 M HCl in dioxane (6.0 mL, 24 mmol). The reaction mixture was stirred at rt for 30 min yielding the titled compound. LC-MS found: 232.2 (m+1).

Intermediate 24

(2S)-2-amino-3-[3-(3-thiophenyl)phenyl]propan-1-ol

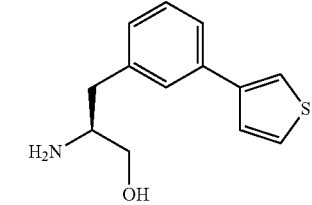 [SMILES: N[C@H](CO)Cc1cccc(-c2ccsc2)c1]

The title compound was prepared substantially as described in Intermediate 23, except substituting thiophene- 3-boronic acid (Aldrich) for 1-methyl-4-(4,4,5,5-tetramethyl-1,3,2-dioxaborolan-2-yl)-1H-pyrazole.

Intermediate 25

(2S)-2-amino-3-[3-(4-pyridinyl)phenyl]propan-1-ol

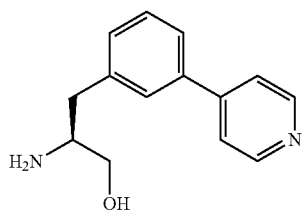 [SMILES: N[C@H](CO)Cc1cccc(-c2ccncc2)c1]

The title compound was prepared substantially as described in Intermediate 23, except substituting pyridine-4-boronic acid (Aldrich) for 1-methyl-4-(4,4,5,5-tetramethyl-1,3,2-dioxaborolan-2-yl)-1H-pyrazole.

Intermediate 26

(2S)-2-amino-3-[3-(3-pyridinyl)phenyl]propan-1-ol

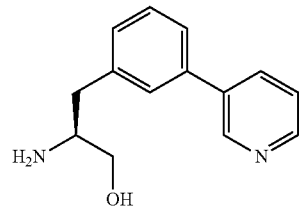 [SMILES: N[C@H](CO)Cc1cccc(-c2cccnc2)c1]

The title compound was prepared substantially as described in Intermediate 23, except substituting pyridine-3-boronic acid (Aldrich) for 1-methyl-4-(4,4,5,5-tetramethyl-1,3,2-dioxaborolan-2-yl)-1H-pyrazole.

Intermediate 27

(2S)-2-amino-3-[3-(5-pyrimidinyl)phenyl]propan-1-ol

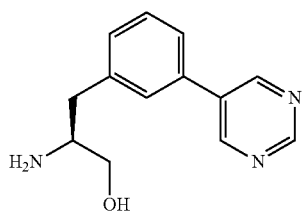 [SMILES: N[C@H](CO)Cc1cccc(-c2cncnc2)c1]

The title compound was prepared substantially as described in Intermediate 23, except substituting pyrimidine-5-boronic acid (Matrix Scientific) for 1-methyl-4-(4,4,5,5-tetramethyl-1, 3,2-dioxaborolan-2-yl)-1H-pyrazole.

Intermediate 28 tert-butyl[2-amino-2-(3-fluorophenyl)-ethyl]carbamate

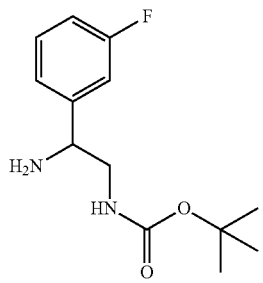 [SMILES: CC(C)(C)OC(=O)NCC(N)c1cccc(F)c1]

Step A:
tert-butyl[2-(3-fluorophenyl)-2-oxoethyl]carbamate

To a solution of tert-butyl {2-[methoxy(methyl)amino]-2-oxoethyl} carbamate [Aldrich] (1.00 g, 4.58 mmol) in tetrahydrofuran (18.3 mL, 226 mmol) at 0° C. was added 0.5 M 3-fluorophenylmagnesium bromide in THF (11.0 mL, 5.50 mmol). The reaction mixture was stirred at 0° C. for 1 h, then quenched at 0° C. with saturated $NH_4Cl$ aqueous solution. The organic layer was separated and the aqueous phase was extracted with EtOAc. The combined extracts were dried over sodium sulfate, filtered and evaporated in vacuo. The residue was purified on combi-flash column eluted with 0-40% EtOAc in hexanes to give 0.322 g (27.8% yield) of the desired product as clear oil. LC-MS found: 254.1 $(M+H)^+$.

Step B: tert-butyl[2-amino-2-(3-fluorophenyl)ethyl] carbamate

To a flask were added tert-butyl[2-(3-fluorophenyl)-2-oxoethyl]carbamate (0.32 g, 1.3 mmol) and ammonium acetate (2.02 g, 26.2 mmol) and methanol (10 mL) and sodium cyanoborohydride (0.22 g, 3.5 mmol). The mixture was refluxed for 2 h. The solvent was removed under vacuum. To the residue was added EtOAc and 50 mL of 1M NaOH. The aqueous phase was extracted again with fresh EtOAc. The combined organic extracts were dried over sodium sulfate, filtered and dried under vacuum to give 0.301 g (94% yield) of the final product as oil. LC-MS found: 155.1 $(M-Boc)^+$.

Intermediate 29 tert-butyl[2-amino-2-(4-fluorophenyl)-ethyl]carbamate

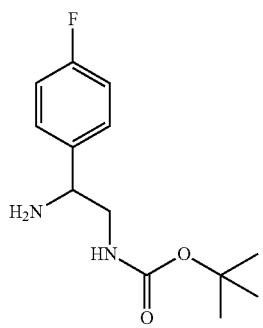 [SMILES: CC(C)(C)OC(=O)NCC(N)c1ccc(F)cc1]

The title compound was prepared substantially as described for Intermediate 28, except substituting 4-fluorophenylmagnesium bromide for 3-fluorophenylmagnesium bromide. LC-MS found: 155.1 (M−Boc)+.

Intermediate 30: tert-butyl[2-amino-2-(3-methoxyphenyl)-ethyl]carbamate

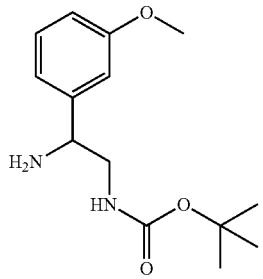 [SMILES: COc1cccc(C(N)CNC(=O)OC(C)(C)C)c1]

The title compound was prepared substantially as described for Intermediate 28, except substituting 3-methoxyphenylmagnesium bromide for 3-fluorophenylmagnesium bromide. LC-MS found: 167.1 (M−Boc)+.

Intermediate 31 tert-butyl[2-amino-2-(4-methoxyphenyl)-ethyl]carbamate

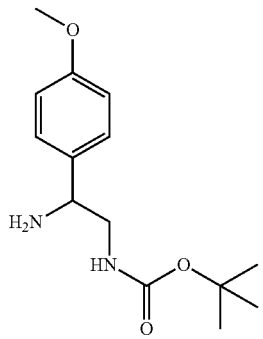 [SMILES: COc1ccc(C(N)CNC(=O)OC(C)(C)C)cc1]

The title compound was prepared substantially as described for Intermediate 28, except substituting 4-methoxyphenylmagnesium bromide for 3-fluorophenylmagnesium bromide. LC-MS found: 167.1 (M−Boc)+.

Example 1

2-[(1S)-2-Amino-1-(3-fluorobenzyl)ethyl]-5-(1-methyl-1H-pyrazol-5-yl)isoindolin-1-one

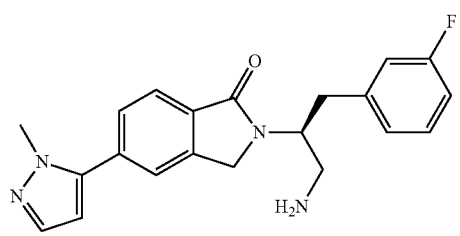 [SMILES: Cn1nccc1-c1ccc2c(c1)CN([C@H](CN)Cc1cccc(F)c1)C2=O]

Step A: tert-butyl[(1S)-1-(3-fluorobenzyl)-2-hydroxyethyl]carbamate

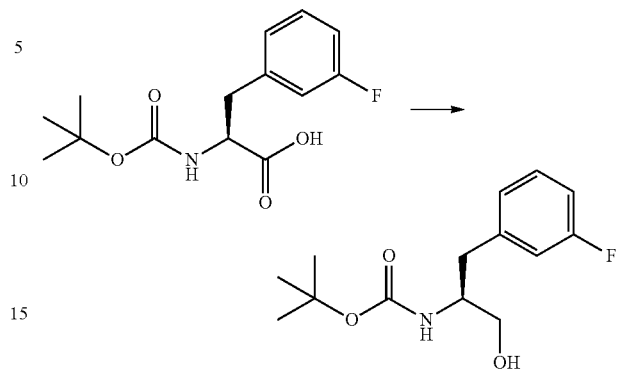

To a solution of (2S)-2-[(tert-butoxycarbonyl)amino]-3-(3-fluorophenyl)propanoic acid [Aldrich] (3.00 g, 10.6 mmol) in tetrahydrofuran (30 mL, 400 mmol) at 0° C. was added 1.0 M borane-THF complex in tetrahydrofuran (32 mL, 32 mmol). The reaction mixture was stirred at room temperature for 3 hrs, cooled with an ice bath, quenched with AcOH:MeOH (1:5, 10 mL and partitioned between saturated aqueous NaHCO$_3$ and DCM. The aqueous phase was then extracted several times with DCM. The combined organic fractions were dried over Na$_2$SO$_4$ and concentrated under reduced pressure. The residue was used directly for the next reaction. LCMS (ES) m/e 270 (M+H)+.

Step B: 2-[(2S)-2-amino-3-(3-fluorophenyl)propyl]-1H-isoindole-1,3(2H)-dione [1.0]-hydrogen chloride

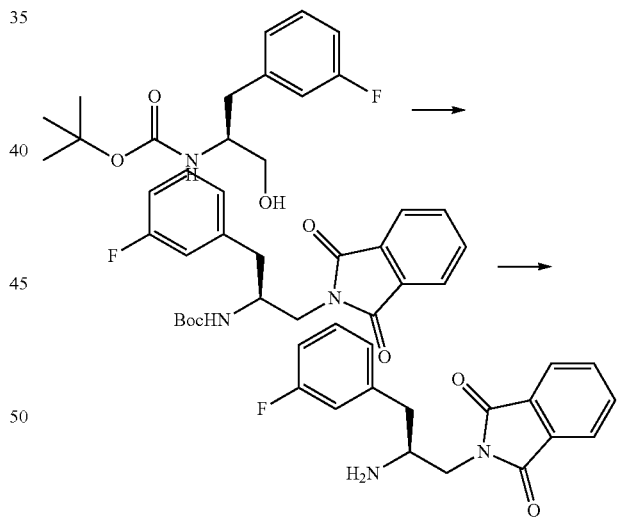

To a solution of tert-butyl[(1S)-1-(3-fluorobenzyl)-2-hydroxyethyl]carbamate (9.40 g, 34.9 mmol), triphenylphosphine (9.15 g, 34.9 mmol), and phthalimide (5.14 g, 34.9 mmol) in tetrahydrofuran (100 mL, 1000 mmol) at room temperature was added diethyl azodicarboxylate (17.9 mL, 45.4 mmol). The reaction was stirred at room temperature for 2 hr and then concentrated under reduced pressure. The residue was purified by combi-flash chromatography eluted with EtOAc/hexane (0-40%) to give the desired intermediate. LCMS found: 399.0 (M+1).

To the solution of the purified intermediate in methanol (20 mL, 400 mmol) was added 4.0 M hydrogen chloride in dioxane (30 mL, 100 mmol). The mixture was stirred at room temperature for 2 h and then concentrated under reduced pressure to give 3.1 g (26% total yield for the two steps) of the final product, 2-[(2S)-2-amino-3-(3-fluorophenyl)propyl]-1H-isoindole-1,3(2H)-dione [1.0]-Hydrogen chloride, as white solid. LC/MS found: 299.0 (M+H)+.

Step C: 2-[(2S)-2-(5-bromo-1-oxo-1,3-dihydro-2H-isoindol-2-yl)-3-(3-fluorophenyl)propyl]-1H-isoindole-1,3(2H)-dione

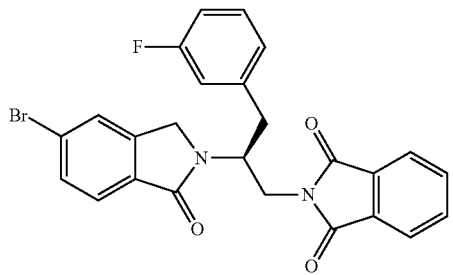 [SMILES: O=C1c2ccccc2C(=O)N1C[C@H](Cc1cccc(F)c1)N1Cc2cc(Br)ccc2C1=O]

A solution of methyl 4-bromo-2-(bromomethyl)benzoate (1.34 g, 4.34 mmol), 2-[(2S)-2-amino-3-(3-fluorophenyl)propyl]-1H-isoindole-1,3(2H)-dione [1.0]-Hydrogen chloride [prepared according to the above Step B] (1.32 g, 3.94 mmol) and N,N-diisopropylethylamine (2.06 mL, 11.8 mmol) in 1-butanol (8 mL, 90 mmol) was stirred at 140° C. for 2 h by microwave. After the reaction mixture was concentrated under reduced pressure, the residue was dissolved in water (30 mL) and EtOAc (30 mL). The organic phase was separated and the aqueous layer was extracted with EtOAc (2×30 mL). The combined organic phases were washed with water, brine and dried over Na2SO4, filtered, and concentrated under reduced pressure. The residue was purified by combi-flash chromatography eluted with EtOAc/hexane (10-60%). The purification gave 1.12 g of the final product as off-white solid. LC/MS found: 492.9 (M+H)+.

Step D: 2-[(2S)-2-[5-(1-methyl-1H-pyrazol-5-yl)-1-oxo-1,3-dihydro-2H-isoindol-2-yl]-3-(3-fluorophenyl)propyl]-1H-isoindole-1,3(2H)-dione

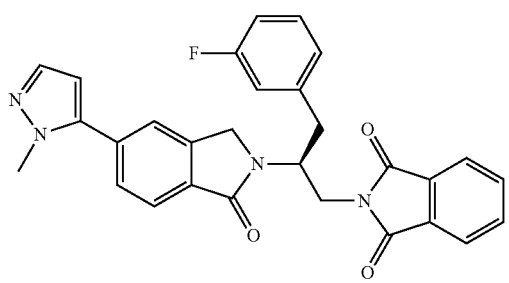 [SMILES: Cn1nccc1-c1ccc2c(c1)CN([C@@H](Cc1cccc(F)c1)CN1C(=O)c3ccccc3C1=O)C2=O]

A mixture of 1-methyl-5-(4,4,5,5-tetramethyl-1,3,2-dioxaborolan-2-yl)-1H-pyrazole (0.557 g, 2.68 mmol), bis(tri-t-butylphosphine)palladium (0.114 g, 0.223 mmol), 2-[(2S)-2-(5-bromo-1-oxo-1,3-dihydro-2H-isoindol-2-yl)-3-(3-fluorophenyl)propyl]-1H-isoindole-1,3(2H)-dione (1.10 g, 2.23 mmol) and N,N-diisopropylethylamine (1.16 mL, 6.69 mmol) in 1,4-dioxane (12 mL, 150 mmol) and water (0.60 mL, 33 mmol) was stirred under microwave at 110° C. for 15 minutes. The reaction mixture was filtered through a pad of celite and the filtrate was concentrated under reduced pressure. The residue was purified by combi-flash chromatography eluted with EtOAc/hexane (30-100%) to give 0.72 g (61% yield) of the desired product. LCMS found: 495.1 (M+H)+.

Step E: 2-[(1S)-2-amino-1-(3-fluorobenzyl)ethyl]-5-(1-methyl-1H-pyrazol-5-yl)isoindolin-1-one The product of Step D (0.72 g, 1.45 mmol) was dissolved in methanol (4 mL, 100 mmol) and tetrahydrofuran (4 mL, 50 mmol). To the resulting solution was added hydrazine (2 mL, 60 mmol). The solution was stirred at 50° C. for 2 h. The reaction mixture was concentrated under reduced pressure and the residue was purified by combi-flash chromatography eluting with MeOH/EtOAc (20-60%). The product was further purified by prep.-LC/MS (pH=10). The purification afforded 345 mg (37.3% yield) of the final product as white solid. LC-MS found: 365.2 (M+1)+; 1H NMR (300 MHz, DMSO-d6) δ ppm: 7.70 (d, J=3.6 Hz, 1H), 7.66 (s, 1H), 7.58 (dd, J1=7.8 Hz, J2=1.2 Hz, 1H), 7.48 (d, J=1.8 Hz, 1H), 7.23 (dd, J1=7.8 Hz, J2=6.3 Hz, 1H), 7.03 (m, 2H), 6.93 (ddd, J1=8.7 Hz, J2=8.4 Hz, J3=2.4 Hz, 1H), 6.45 (d, J=2.1 Hz, 1H), 4.46 (s, 2H), 4.40 (m, 1H), 3.86 (s, 3H), 3.04 (dd, J1=14.4 Hz, J2=5.1 Hz, 1H), 2.88 (dd, J1=14.40 Hz, J2=4.5 Hz, 1H), 2.82 (d, J=6.9 Hz, 2H).

Example 2

2-[(1S)-2-amino-1-(3-fluorobenzyl)ethyl]-5-(4-chloro-1-methyl-1H-pyrazol-5-yl)isoindolin-1-one

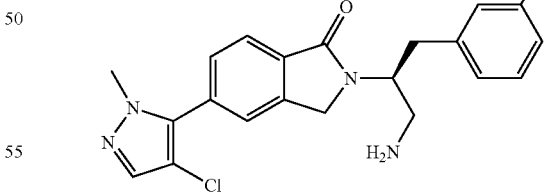

The title compound was prepared as a white solid according to Example 1, except starting with 4-chloro-1-methyl-5-(4,4,5,5-tetramethyl-1,3,2-dioxaborolan-2-yl)-1H-pyrazole [prepared in Intermediate 1] instead of 1-methyl-5-(4,4,5,5-tetramethyl-1,3,2-dioxaborolan-2-yl)-1H-pyrazole: LC-MS (ES) m/z 399.1 (M+H)+; 1H NMR (400 MHz, DMSO-d6): 7.73 (d, J=7.6 Hz, 1H), 7.69 (s, 1H), 7.68 (s, 1H), 7.55 (d, J=7.6 Hz, 1H), 7.23 (dd, J1=14.4 Hz, J2=8.00 Hz, 1H), 7.04 (m, 2H), 6.94 (t, J=8.80 Hz, 1H), 4.48 (d, J=2.40 Hz, 2H), 4.41 (m, 1H), 3.75 (s, 3H), 3.03 (dd, J$^1$=14.40 Hz, J$^2$=5.20 Hz, 1H), 2.88 (dd, J$^1$=14.40 Hz, J$^2$=10.00 Hz, 1H), 2.80 (d, J=6.80 Hz, 2H).

Example 3

2-[(1S)-2-amino-1-(3-fluorobenzyl)ethyl]-5-(4-methyl-1-methyl-1H-pyrazol-5-yl)isoindolin-1-one

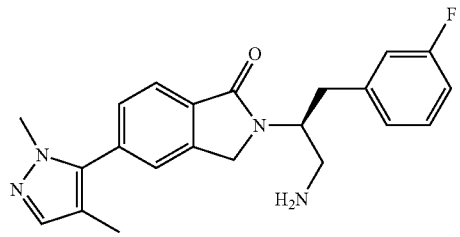 [SMILES: Cc1cnn(C)c1-c1ccc2c(c1)CN([C@H](CN)Cc1cccc(F)c1)C2=O]

The title compound was prepared as a white solid according to Example 1, except starting with 4-methyl-1-methyl-5-(4,4,5,5-tetramethyl-1,3,2-dioxaborolan-2-yl)-1H-pyrazole [prepared in Intermediate 2] instead of 1-methyl-5-(4,4,5,5-tetramethyl-1,3,2-dioxaborolan-2-yl)-1H-pyrazole. LC-MS found: 379.1 (M+H)$^+$; $^1$H NMR (400 MHz, DMSO-d$_6$): 7.69 (d, J=7.60 Hz, 1H), 7.59 (s, 1H), 7.45 (dd, J$^1$=7.60 Hz, J$^2$=1.20 Hz, 1H), 7.34 (s, 1H), 7.24 (m, 1H), 7.04 (m, 2H), 6.94 (dt, J=8.00 Hz, 1.60 Hz, 1H), 4.46 (d, J=4.40 Hz, 2H), 4.42 (m, 1H), 3.69 (s, 3H), 3.03 (dd, J$^1$=14.80 Hz, J$^2$=5.60 Hz, 1H), 2.90 (dd, J$^1$=14.4 Hz, J$^2$=9.60 Hz, 1H), 2.80 (d, J1=6.80 Hz, 2H), 1.85 (s, 3H).

Example 4

2-[(1S)-2-amino-1-(3-fluorobenzyl)ethyl]-5-(4-methoxymethyl-1-methyl-1H-pyrazol-5-yl)isoindolin-1-one

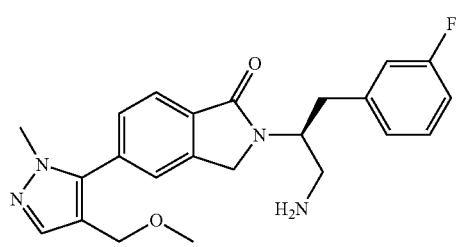 [SMILES: COCc1cnn(C)c1-c1ccc2c(c1)CN([C@H](CN)Cc1cccc(F)c1)C2=O]

The title compound was prepared as a white solid according to Example 1, except starting with 4-methoxymethyl-1-methyl-5-(4,4,5,5-tetramethyl-1,3,2-dioxaborolan-2-yl)-1H-pyrazole [prepared in Intermediate 3] instead of 1-methyl-5-(4,4,5,5-tetramethyl-1,3,2-dioxaborolan-2-yl)-1H-pyrazole: LC-MS (ES) m/z 409.1 (M+H)$^+$; $^1$H NMR (400 MHz, DMSO-d$_6$) δ: 7.71 (d, J=8.00 Hz, 1H), 7.64 (s, 1H), 7.54 (s, 1H), 7.52 (d, J=8.40 Hz, 1H), 7.24 (m, 1H), 7.05 (m, 2H), 6.94 (m, 1H), 4.48 (d, J=3.20 Hz, 2H), 4.43 (m, 1H), 4.12 (s, 2H), 3.75 (s, 3H), 3.16 (s, 3H), 3.04 (m, 1H), 2.89 (m, 1H), 2.81 (d, J=6.80 Hz, 2H).

Example 5

2-[(1S)-2-amino-1-(3-fluorobenzyl)ethyl]-5-(4-ethoxymethyl-1-methyl-1H-pyrazol-5-yl)isoindolin-1-one

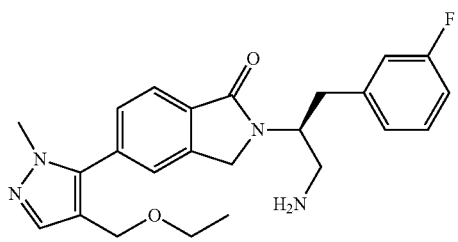 [SMILES: CCOCc1cnn(C)c1-c1ccc2c(c1)CN([C@H](CN)Cc1cccc(F)c1)C2=O]

The title compound was prepared as a white solid according to Example 1, except starting with 4-ethoxymethyl-1-methyl-5-(4,4,5,5-tetramethyl-1,3,2-dioxaborolan-2-yl)-1H-pyrazole [prepared in Intermediate 4] instead of 1-methyl-5-(4,4,5,5-tetramethyl-1,3,2-dioxaborolan-2-yl)-1H-pyrazole. LC-MS found: 423.1 (M+H)$^+$.

Example 6

2-[(1S)-2-amino-1-(3-fluorobenzyl)ethyl]-5-[4-(2-propoxymethyl)-1-methyl-1H-pyrazol-5-yl]isoindolin-1-one

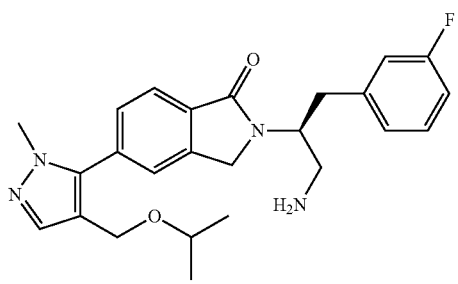 [SMILES: CC(C)OCc1cnn(C)c1-c1ccc2c(c1)CN([C@H](CN)Cc1cccc(F)c1)C2=O]

The title compound was prepared as a white solid according to Example 1, except starting with 4-(2-propoxymethyl)-1-methyl-5-(4,4,5,5-tetramethyl-1,3,2-dioxaborolan-2-yl)-1H-pyrazole [prepared in Intermediate 5] instead of 1-methyl-5-(4,4,5,5-tetramethyl-1,3,2-dioxaborolan-2-yl)-1H-pyrazole. LC-MS found: 437.1 (M+H)$^+$; $^1$H NMR (400 MHz, DMSO-d$_6$) of example: 7.69 (m, 2H), 7.55 (m, 1H), 7.51 (s, 1H), 7.22 (m, 1H), 7.03 (m, 3H), 4.39 (m, 3H), 4.14 (s, 2H), 3.75 (s, 3H), 3.52 (m, 1H), 2.81 (m, 4H), 1.03 (d, J=8.0 Hz, 6H).

Example 7

2-[(1S)-2-amino-1-(3-fluorobenzyl)ethyl]-5-[4-(1-propoxymethyl)-1-methyl-1H-pyrazol-5-yl]isoindolin-1-one

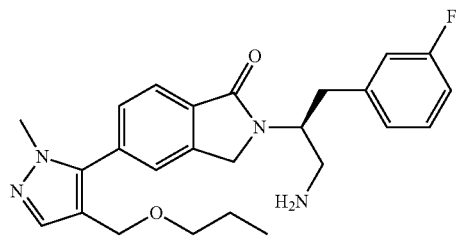 [SMILES: CCCOCc1cnn(C)c1-c1ccc2c(c1)CN([C@H](CN)Cc1cccc(F)c1)C2=O]

The title compound was prepared as a white solid according to Example 1, except starting with 4-(1-propoxymethyl)-1-methyl-5-(4,4,5,5-tetramethyl-1,3,2-dioxaborolan-2-yl)-1H-pyrazole [prepared in Intermediate 6] instead of 1-methyl-5-(4,4,5,5-tetramethyl-1,3,2-dioxaborolan-2-yl)-1H-pyrazole. LC-MS found: 437.1 (M+H)$^+$; $^1$H NMR (300 MHz, DMSO-d$_6$) of example: 7.69 (m, 2H), 7.54 (m, 2H), 7.25 (m, 1H), 7.00 (m, 3H), 4.51 (m, 3H), 4.16 (s, 2H), 3.76 (s, 3H), 3.28 (t, J=6.5 Hz, 2H), 2.92 (m, 4H), 1.46 (m, 2H), 0.80 (t, J=7.4 Hz, 3H).

Example 8

2-[(1S)-2-amino-1-(3-fluorobenzyl)ethyl]-5-(4-cyclobutoxymethyl-1-methyl-1H-pyrazol-5-yl)isoindolin-1-one

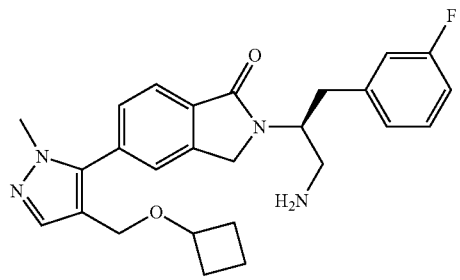 [SMILES: Cn1ncc(COC2CCC2)c1-c1ccc2c(c1)CN([C@H](CN)Cc1cccc(F)c1)C2=O]

The title compound was prepared as a white solid according to Example 1, except starting with 4-cyclobutoxymethyl-1-methyl-5-(4,4,5,5-tetramethyl-1,3,2-dioxaborolan-2-yl)-1H-pyrazole [prepared in Intermediate 7] instead of 1-methyl-5-(4,4,5,5-tetramethyl-1,3,2-dioxaborolan-2-yl)-1H-pyrazole. LC-MS found: 449.1 (M+H)$^+$; $^1$H NMR (300 MHz, DMSO-d$_6$) of example: 7.70 (m, 2H), 7.55 (d, J=1.3 Hz, 1H), 7.53 (s, 1H), 7.24 (m, 1H), 7.01 (m, 3H), 4.47 (m, 3H), 4.07 (s, 2H), 3.88 (m, 1H), 3.75 (s, 3H), 2.91 (m, 4H), 2.02 (m, 2H), 1.74 (m, 4H).

Example 9

2-[(1S)-2-amino-1-(3-fluorobenzyl)ethyl]-5-(4-cyclopropylmethoxymethyl-1-methyl-1H-pyrazol-5-yl)isoindolin-1-one

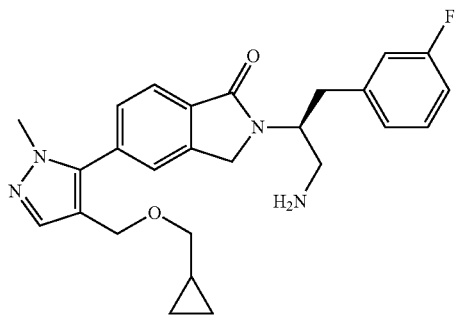 [SMILES: Cn1ncc(COCC2CC2)c1-c1ccc2c(c1)CN([C@H](CN)Cc1cccc(F)c1)C2=O]

The title compound was prepared as a white solid according to Example 1, except starting with 4-cyclopropylmethoxymethyl-1-methyl-5-(4,4,5,5-tetramethyl-1,3,2-dioxaborolan-2-yl)-1H-pyrazole [prepared in Intermediate 8] instead of 1-methyl-5-(4,4,5,5-tetramethyl-1,3,2-dioxaborolan-2-yl)-1H-pyrazole. LC-MS found: 449.1 (M+H)$^+$; $^1$H NMR (400 MHz, DMSO-d$_6$) of example: 7.70 (m, 2H), 7.55 (m, 2H), 7.25 (m, 1H), 7.03 (m, 3H), 4.46 (m, 3H), 4.18 (s, 2H), 3.76 (s, 3H), 3.17 (d, J=6.8 2H), 2.98 (m, 2H), 2.82 (d, J=6.9 Hz, 2H), 0.94 (m, 1H), 0.41 (m, 2H), 0.09 (m, 2H).

Example 10

2-[(1S)-2-amino-1-(3-fluorobenzyl)ethyl]-5-[(methylthio)methyl-1-methyl-1H-pyrazol-5-yl)]isoindolin-1-one

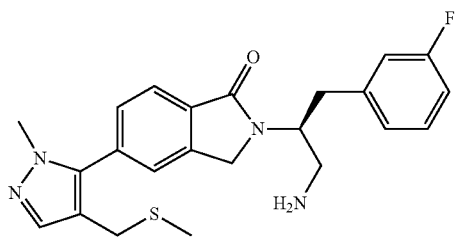

The title compound was prepared as a white solid according to Example 1, except starting with 4-(methylthio)methyl-1-methyl-5-(4,4,5,5-tetramethyl-1,3,2-dioxaborolan-2-yl)-1H-pyrazole [prepared in Intermediate 11] instead of 1-methyl-5-(4,4,5,5-tetramethyl-1,3,2-dioxaborolan-2-yl)-1H-pyrazole. LC-MS found: 425.1 (M+H)⁺.

Example 11

2-[(1S)-2-amino-1-(3-fluorobenzyl)ethyl]-5-(4-fluoro-1-methyl-1H-pyrazol-5-yl)isoindolin-1-one

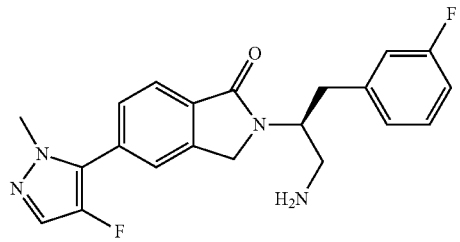 [SMILES: Cn1ncc(F)c1-c1ccc2c(c1)CN([C@H](CN)Cc1cccc(F)c1)C2=O]

Step A: 2-[(2S)-2-[5-(4-fluoro-1-methyl-1H-pyrazol-5-yl)-1-oxo-1,3-dihydro-2H-isoindol-2-yl]-3-(3-fluorophenyl)propyl]-1H-isoindole-1,3(2H)-dione

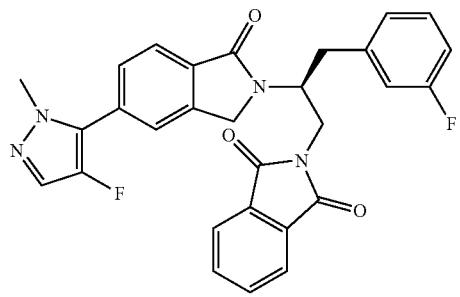 [SMILES: Cn1ncc(F)c1-c1ccc2c(c1)CN([C@@H](Cc1cccc(F)c1)CN1C(=O)c3ccccc3C1=O)C2=O]

To a solution of 2-{(2S)-3-(3-fluorophenyl)-2-[5-(1-methyl-1H-pyrazol-5-yl)-1-oxo-1,3-dihydro-2H-isoindol-2-yl]propyl}-1H-isoindole-1,3(2H)-dione (200.0 mg, 0.4044 mmol) [prepared in Example 1] in tetrahydrofuran (7 mL) and water (0.5 mL) was added SELECTFLUOR® fluorinating reagent (1-chloromethyl-4-fluoro-1,4-diazoniabicyclo[2.2.2]-octane bis(tetrafluoroborate) (212.0 mg, 0.60 mmol). The reaction mixture was sealed and stirred at 70° C. for 1 h and then additional SELECTFLUOR® fluorinating reagent (212.0 mg, 0.60 mmol) was added. The reaction mixture was sealed again and stirred at 70° C. overnight. The reaction mixture was then filtered and the filtrate was concentrated under reduced pressure. The residue was purified by prep.—HPLC. The purification afforded 61 mg (30% yield) of the desired product as white solid. LC/MS found: 513.0 (M+1)⁺.

Step B: 2-[(1S)-2-amino-1-(3-fluorobenzyl)ethyl]-5-(4-fluoro-1-methyl-1H-pyrazol-5-yl)isoindolin-1-one A solution of 2-[(2S)-2-[5-(4-fluoro-1-methyl-1H-pyrazol-5-yl)-1-oxo-1,3-dihydro-2H-isoindol-2-yl]-3-(3-fluorophenyl)propyl]-1H-isoindole-1,3(2H)-dione (30.0 mg, 0.058 mmol) and hydrazine (0.2 mL, 6 mmol) in methanol (1.0 mL) and tetrahydrofuran (1.0 mL) was stirred at room temperature overnight. Direct purification on prep.—HPLC (pH=10) gave 8.1 mg of the desired product as white solid. LC/MS found: 383.0 (M+1)⁺; ¹H NMR (400 MHz, DMSO-d₆) δ ppm: 7.73 (d, J=7.8 Hz, 1H), 7.71 (s, 1H), 7.61 (d, J=4.9 Hz, 1H), 7.57 (d, J=7.9 Hz, 1H), 7.23 (ddd, J¹=8.2 Hz, J²=7.8 Hz, J³=6.4 Hz, 1H), 7.03 (m, 2H), 6.93 (dddd, J¹=8.6 Hz, J²=8.4 Hz, J³=2.6 Hz, J⁴=0.8 Hz, 1H), 4.48 (s, 2H), 4.42 (m, 1H), 3.79 (s, 3H), 3.05 (dd, J¹=14.40 Hz, J²=5.20 Hz, 1H), 2.88 (dd, J¹=14.40 Hz, J²=10.00 Hz, 1H), 2.81 (d, J=6.70 Hz, 2H).

Example 12

2-[(1S)-2-amino-1-(3-fluorobenzyl)ethyl]-5-(4-bromo-1-methyl-1H-pyrazol-5-yl)isoindolin-1-one

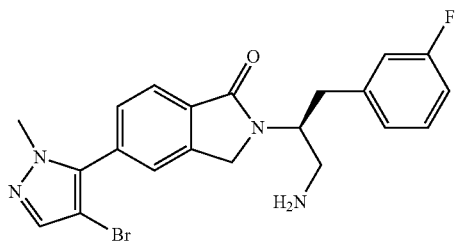

Step A: 2-[(2S)-2-[5-(4-bromo-1-methyl-1H-pyrazol-5-yl)-1-oxo-1,3-dihydro-2H-isoindol-2-yl]-3-(3-fluorophenyl)propyl]-1H-isoindole-1,3(2H)-dione

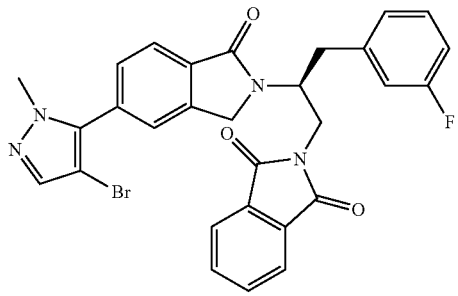 [SMILES: Cn1ncc(Br)c1-c1ccc2c(c1)CN([C@@H](Cc1cccc(F)c1)CN1C(=O)c3ccccc3C1=O)C2=O]

To a solution of 2-{(2S)-3-(3-fluorophenyl)-2-[5-(1-methyl-1H-pyrazol-5-yl)-1-oxo-1,3-dihydro-2H-isoindol-2-yl]propyl}-1H-isoindole-1,3(2H)-dione (200.0 mg, 0.4044 mmol) [prepared in Example 1] in tetrahydrofuran (5 mL) was added N-bromosuccinimide (72.0 mg, 0.404 mmol). The solution was stirred at room temperature for 1 h and then concentrated under reduced pressure. The residue was purified by combi-flash chromatography eluted with EtOAc/hexane (50-100%). The purification afforded 231 mg (99.6% yield) of the desired product as white solid. LC/MS found: 573.0 (M+1)⁺.

Step B: 2-[(1S)-2-amino-1-(3-fluorobenzyl)ethyl]-5-(4-bromo-1-methyl-1H-pyrazol-5-yl)isoindolin-1-one A solution of 2-[(2S)-2-[5-(4-bromo-1-methyl-1H-pyrazol-5-yl)-1-oxo-1,3-dihydro-2H-isoindol-2-yl]-3-(3-fluorophenyl)propyl]-1H-isoindole-1,3(2H)-dione (30.0 mg, 0.0523 mmol) and hydrazine (0.2 mL, 6 mmol) in methanol (1.0 mL) and tetrahydrofuran (1.0 mL) was stirred at room temperature overnight. Direct purification on prep.—HPLC (pH=10) gave 7.8 mg of the desired product as white solid. LC/MS found: 443.0 (M+1)⁺; ¹H NMR (400 MHz, DMSO-d₆) δ: 7.74 (d, J=7.60 Hz, 1H), 7.68 (m, 2H), 7.54 (dd, J¹=8.00 Hz, J²=1.60 Hz, 1H), 7.24 (m, 1H), 7.05 (m, 2H), 6.95 (dt, J¹=8.40 Hz, J²=2.00 Hz, 1H), 4.49 (d, J=2.80 Hz, 2H), 4.42

(m, 1H), 3.76 (s, 3H), 3.04 (dd, J¹=14.00 Hz, J²=5.20 Hz, 1H), 2.90 (dd, J¹=14.40 Hz, J²=9.60 Hz, 1H), 2.81 (d, J=6.80 Hz, 2H).

Example 13

2-[(1S)-2-amino-1-(3-fluorobenzyl)ethyl]-5-(4-cyano-1-methyl-1H-pyrazol-5-yl)isoindolin-1-one

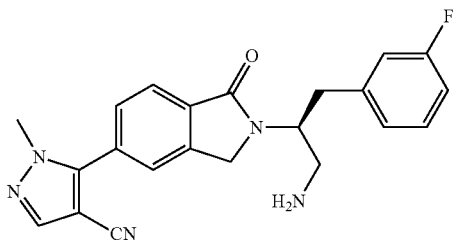 [SMILES: Cn1ncc(C#N)c1-c1ccc2c(c1)CN([C@H](CN)Cc1cccc(F)c1)C2=O]

A mixture of zinc cyanide (64.5 mg, 0.549 mmol), 2-[(2S)-2-[5-(4-bromo-1-methyl-1H-pyrazol-5-yl)-1-oxo-1,3-dihydro-2H-isoindol-2-yl]-3-(3-fluorophenyl)propyl]-1H-isoindole-1,3(2H)-dione (105.0 mg, 0.1831 mmol) [prepared in Example 12] and tetrakis(triphenylphosphine)palladium(0) (21 mg, 0.018 mmol) in N-methylpyrrolidinone (1 mL) in a sealed tube was microwaved at 190° C. for 1 h. The reaction mixture was filtered and the filtrate was diluted with EtOAc (50 mL). The organic phase was washed with water, brine and concentrated under reduced pressure. Direct purification on prep.—HPLC (pH=10) gave the desired intermediate as white solid. LC-MS found: 520.1 (M+H)⁺.

The above intermediate was dissolved in methanol (2 mL), tetrahydrofuran (2 mL) and hydrazine (0.2 mL, 6 mmol). The solution was stirred at 50° C. for 2 h. Direct purification on prep.—HPLC (pH=10) gave 7.4 mg of the desired product as white solid. LC/MS found: 390.1 (M+1)⁺; ¹H NMR (400 MHz, DMSO-d₆) δ: 8.13 (s, 1H), 7.77 (s, 1H), 7.75 (d, J=8.00 Hz, 1H), 7.62 (dd, J¹=7.60 Hz, J²=1.20 Hz, 1H), 7.18 (m, 1H), 7.00 (m, 2H), 6.89 (dt, J¹=8.40 Hz, J²=2.40 Hz, 1H), 4.47 (s, 2H), 4.38 (m, 1H), 3.80 (s, 3H), 3.00 (dd, J¹=14.4 Hz, J²=5.20 Hz, 1H), 2.85 (dd, J¹=14.00 Hz, J²=9.60 Hz, 1H), 2.77 (d, J=6.80 Hz, 2H).

Example 14

2-[(1S)-2-amino-1-(3-fluorobenzyl)ethyl]-5-(4-phenyl-1-methyl-1H-pyrazol-5-yl)isoindolin-1-one

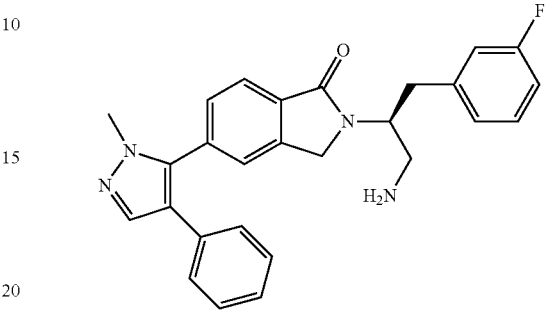

A mixture of phenylboronic acid (12.8 mg, 0.105 mmol), bis(tri-t-butylphosphine)palladium (4.46 mg, 0.00872 mmol), 2-[(2S)-2-[5-(4-bromo-1-methyl-1H-pyrazol-5-yl)-1-oxo-1,3-dihydro-2H-isoindol-2-yl]-3-(3-fluorophenyl)propyl]-1H-isoindole-1,3(2H)-dione (see Example 12) (50.0 mg, 0.0872 mmol) and N,N-diisopropylethylamine (45.6 µL, 0.262 mmol) in 1,4-dioxane (1 mL) and water (50 µL) was microwaved at 110° C. for 15 minutes. The reaction mixture was filtered through a pad of celite and the filtrate was concentrated under reduced pressure. The residue was purified by combi-flash chromatography eluted with EtOAc/hexane (50-100%) to give the desired intermediate. LC-MS found: 571.1 (M+H)⁺.

The above intermediate was dissolved in methanol (1 mL), tetrahydrofuran (1 mL) and hydrazine (0.2 mL, 6 mmol). The resulting solution was stirred at 50° C. for 2 h. Direct purification on prep.—HPLC (pH=10) gave 10.2 mg of the final product as white solid. LC/MS found: 441.1 (M+1)⁺.

The following compounds listed in Table 1 were prepared by a method analogous to that for Example 14.

TABLE 1

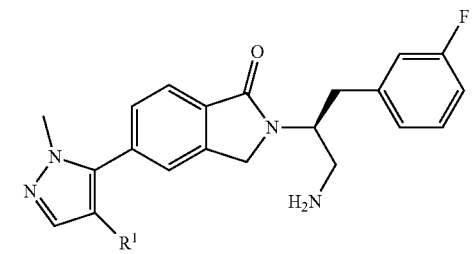

| Ex. # | R¹ | Compound | LC-MS (M + H)⁺ |
|---|---|---|---|
| 15 | 2-thienyl | 2-[(1S)-2-amino-1-(3-fluorobenzyl)ethyl]-5-[1-methyl-4-(2-thienyl)-1H-pyrazol-5-yl]isoindolin-1-one | 447.2 |
| 16 | 3-thienyl | 2-[(1S)-2-amino-1-(3-fluorobenzyl)ethyl]-5-[1-methyl-4-(3-thienyl)-1H-pyrazol-5-yl]isoindolin-1-one | 447.1 |

TABLE 1-continued

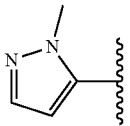 [SMILES: *c1ccnn1C]

| Ex. # | R¹ | Compound | LC-MS (M + H)⁺ |
|---|---|---|---|
| 17 | 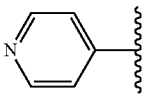 | 2-[(1S)-2-amino-1-(3-fluorobenzyl)ethyl]-5-(1',2-dimethyl-1'H,2H-3,4'-bipyrazol-5'-yl)isoindolin-1-one | 445.1 |
| 18 | 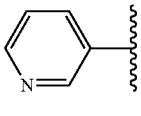 | 2-[(1S)-2-amino-1-(3-fluorobenzyl)ethyl]-5-(1-methyl-4-pyridin-4-yl-1H-pyrazol-5-yl)isoindolin-1-one | 442.0 |
| 19 | 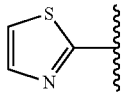 | 2-[(1S)-2-amino-1-(3-fluorobenzyl)ethyl]-5-(1-methyl-4-pyridin-4-yl-1H-pyrazol-5-yl)isoindolin-1-one | 442.0 |
| 20 | 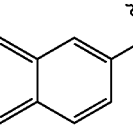 | 2-[(1S)-2-amino-1-(3-fluorobenzyl)ethyl]-5-[1-methyl-4-(1,3-thiazol-2-yl)-1H-pyrazol-5-yl]isoindolin-1-one | 448.1 |
| 21 | 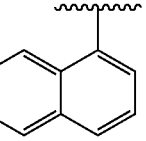 | 2-[(1S)-2-amino-1-(3-fluorobenzyl)ethyl]-5-[1-methyl-4-(2-naphthyl)-1H-pyrazol-5-yl]isoindolin-1-one | 491.2 |
| 22 | 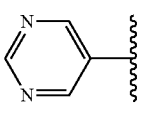 [SMILES: *c1cncnc1] | 2-[(1S)-2-amino-1-(3-fluorobenzyl)ethyl]-5-[1-methyl-4-(1-naphthyl)-1H-pyrazol-5-yl]isoindolin-1-one | 491.2 |
| 23 | 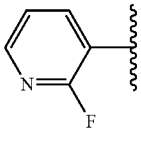 [SMILES: *c1cccnc1F] | 2-[(1S)-2-amino-1-(3-fluorobenzyl)ethyl]-5-(1-methyl-4-pyrimidin-5-yl-1H-pyrazol-5-yl)isoindolin-1-one | 443.1 |
| 24 | 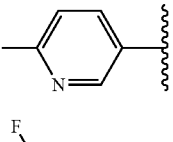 | 2-[(1S)-2-amino-1-(3-fluorobenzyl)ethyl]-5-[4-(2-fluoropyridin-3-yl)-1-methyl-1H-pyrazol-5-yl]isoindolin-1-one | 460.1 |
| 25 | 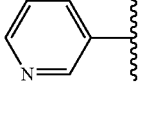 | 2-[(1S)-2-amino-1-(3-fluorobenzyl)ethyl]-5-[4-(6-fluoropyridin-3-yl)-1-methyl-1H-pyrazol-5-yl]isoindolin-1-one | 460.1 |
| 26 | | 2-[(1S)-2-amino-1-(3-fluorobenzyl)ethyl]-5-[4-(5-fluoropyridin-3-yl)-1-methyl-1H-pyrazol-5-yl]isoindolin-1-one | 460.1 |

TABLE 1-continued

| Ex. # | R¹ | Compound | LC-MS (M + H)⁺ |
|---|---|---|---|
| 27 | (3-pyridyl with 2-methoxy) | 2-[(1S)-2-amino-1-(3-fluorobenzyl)ethyl]-5-[4-(2-methoxypyridin-3-yl)-1-methyl-1H-pyrazol-5-yl]isoindolin-1-one | 472.1 |
| 28 | (3-pyridyl with 6-methoxy) | 2-[(1S)-2-amino-1-(3-fluorobenzyl)ethyl]-5-[4-(6-methoxypyridin-3-yl)-1-methyl-1H-pyrazol-5-yl]isoindolin-1-one | 472.0 |
| 29 | (N-methylpyridine-2-carboxamide) | 5-(5-{2-[(1S)-2-amino-1-(3-fluorobenzyl)ethyl]-1-oxo-2,3-dihydro-1H-isoindol-5-yl}-1-methyl-1H-pyrazol-4-yl)-N-methylpyridine-2-carboxamide | 499.3 |

Example 30

5-(4-chloro-1-methyl-1H-pyrazol-5-yl)-2-[(1S)-1-(3-fluorobenzyl)-2-(methylamino)ethyl]isoindolin-1-one

Step A: (2S)-2-amino-3-(3-fluorophenyl)propan-1-ol [1.0]-hydrogen chloride

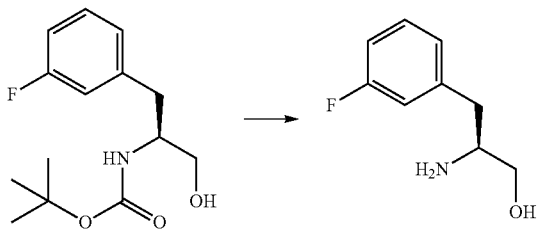 [SMILES: CC(C)(C)OC(=O)N[C@H](CO)Cc1cccc(F)c1 ; N[C@H](CO)Cc1cccc(F)c1]

A mixture of tert-butyl[(1S)-1-(3-fluorobenzyl)-2-hydroxyethyl]carbamate [prepared in Example 1] (11.5 g, 42.7 mmol) and 4.0 M hydrogen chloride in dioxane (50 mL, 200 mmol) in methanol (50 mL) was stirred at room temperature for 1 h. Concentration of the reaction mixture under reduced pressure gave 8.77 g (99.1% yield) of the desired product as white solid. LC/MS found: 170.1 (M+1)⁺.

Step B: 5-bromo-2-[(1S)-1-(3-fluorobenzyl)-2-hydroxyethyl]isoindolin-1-one

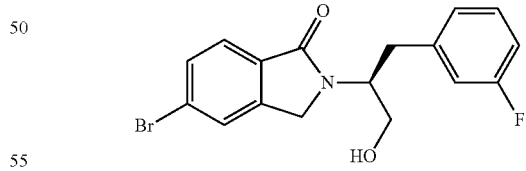

A solution methyl 4-bromo-2-(bromomethyl)benzoate (14.8 g, 48.1 mmol), (2S)-2-amino-3-(3-fluorophenyl)propan-1-ol[1.0]-hydrogen chloride (8.24 g, 40.1 mmol) and N,N-diisopropylethylamine (20.9 mL, 1.20E2 mmol) in 1-butanol (20 mL) in a sealed tube was stirred at 140° C. for 2 h. The reaction mixture was concentrated under reduced pressure and the residue was purified by combi-flash chromatography eluted with EtOAc/hexane (50-100%) to give 9.51 g (65.2% yield) of the desired product as off-white solid. LC/MS found: 363.9 (M+1)⁺.

Step C: 5-(4-chloro-1-methyl-1H-pyrazol-5-yl)-2-[(1S)-1-(3-fluorobenzyl)-2-hydroxyethyl]isoindolin-1-one

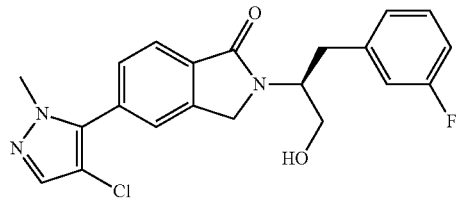 [SMILES: Cn1ncc(Cl)c1-c1ccc2c(c1)CN([C@H](CO)Cc1cccc(F)c1)C2=O]

A mixture of 4-chloro-1-methyl-5-(4,4,5,5-tetramethyl-1,3,2-dioxaborolan-2-yl)-1H-pyrazole (177.0 mg, 0.7297 mmol), bis(tri-t-butylphosphine)palladium (31.1 mg, 0.0608 mmol), 5-bromo-2-[(1S)-1-(3-fluorobenzyl)-2-hydroxyethyl]isoindolin-1-one (220.0 mg, 0.6081 mmol) and N,N-diisopropylethylamine (0.318 mL, 1.82 mmol) in 1,4-dioxane (3 mL, 40 mmol) and water (150 μL, 8.3 mmol) was microwaved at 110° C. for 15 minutes. The reaction mixture was filtered through a pad of celite and the filtrate was concentrated under reduced pressure. The residue was purified by combi-flash chromatography eluting with EtOAc/hexane (30-100%) to give 0.162 g (67% yield) of the desired product as yellowish solid. LC/MS found: 399.9 (M+1)⁺.

Step D: (2S)-2-[5-(4-chloro-1-methyl-1H-pyrazol-5-yl)-1-oxo-1,3-dihydro-2H-isoindol-2-yl]-3-(3-fluorophenyl)propanal

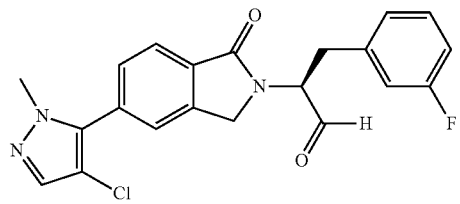 [SMILES: Cn1ncc(Cl)c1-c1ccc2c(c1)CN([C@H](C=O)Cc1cccc(F)c1)C2=O]

To a solution of 5-(4-chloro-1-methyl-1H-pyrazol-5-yl)-2-[(1S)-1-(3-fluorobenzyl)-2-hydroxyethyl]isoindolin-1-one (0.8 g, 2.001 mmol) in methylene chloride (10 mL, 200 mmol) at 0° C. was added Dess-Martin periodinane (1.02 g, 2.40 mmol). The reaction mixture was stirred at room temperature for 1 h, and then quenched with 1 N NaOH aqueous solution, and extracted with DCM (2×). The combined organic phases were washed with water, brine and dried over Na₂SO₄, filtered and concentrated under reduced pressure to give 685 mg (86% yield) of the desired product as yellowish solid. LC/MS found: 398.1 (M+H)⁺.

Step E: 5-(4-chloro-1-methyl-1H-pyrazol-5-yl)-2-[(1S)-1-(3-fluorobenzyl)-2-(methylamino)ethyl]isoindolin-1-one A mixture of (2S)-2-[5-(4-chloro-1-methyl-1H-pyrazol-5-yl)-1-oxo-1,3-dihydro-2H-isoindol-2-yl]-3-(3-fluorophenyl)propanal (40.0 mg, 0.100 mmol), methylamine (20.3 μL, 0.151 mmol) and sodium triacetoxyborohydride (42.6 mg, 0.201 mmol) in tetrahydrofuran (1 mL) was stirred at room temperature overnight. Direct purification on prep.—HPLC (pH=10) gave the desired product as white solid. LC-MS found: 413.1 (M+H)⁺.

The following compounds listed in Table 2 were prepared by a method analogous to that for Example 30.

TABLE 2

| Ex. # | R³ | R² | Compound | LC-MS (M+H)⁺ |
|---|---|---|---|---|
| 31 | H | Et | 5-(4-chloro-1-methyl-1H-pyrazol-5-yl)-2-[(1S)-2-(ethylamino)-1-(3-fluorobenzyl)ethyl]isoindolin-1-one | 426.9 |
| 32 | H | i-Pr | 5-(4-chloro-1-methyl-1H-pyrazol-5-yl)-2-[(1S)-1-(3-fluorobenzyl)-2-(isopropylamino)ethyl]isoindolin-1-one | 441.1 |
| 33 | H | cyclopropyl | 5-(4-chloro-1-methyl-1H-pyrazol-5-yl)-2-[(1S)-2-(cyclopropylamino)-1-(3-fluorobenzyl)ethyl]isoindolin-1-one | 438.9 |
| 34 | H | cyclobutyl | 5-(4-chloro-1-methyl-1H-pyrazol-5-yl)-2-[(1S)-2-(cyclobutylamino)-1-(3-fluorobenzyl)ethyl]isoindolin-1-one | 453.0 |
| 35 | H | cyclopentyl | 5-(4-chloro-1-methyl-1H-pyrazol-5-yl)-2-[(1S)-2-(cyclopentylamino)-1-(3-fluorobenzyl)ethyl]isoindolin-1-one | 467.0 |
| 36 | H | tetrahydropyran-4-yl | 5-(4-chloro-1-methyl-1H-pyrazol-5-yl)-2-[(1S)-1-(3-fluorobenzyl)-2-(tetrahydro-2H-pyran-4-ylamino)ethyl]isoindolin-1-one | 483.1 |
| 37 | H | 1-methylpiperidin-4-yl | 5-(4-chloro-1-methyl-1H-pyrazol-5-yl)-2-{(1S)-1-(3-fluorobenzyl)-2-[(1-methylpiperidin-4-yl)amino]ethyl}isoindolin-1-one | 496.0 |
| 38 | Me | Me | 5-(4-chloro-1-methyl-1H-pyrazol-5-yl)-2-[(1S)-2-(dimethylamino)-1-(3-fluorobenzyl) | 426.9 |

TABLE 2-continued

| Ex. # | R³ | R² | Compound | LC-MS (M + H)⁺ |
|---|---|---|---|---|
| 39 | Et | Et | 5-(4-chloro-1-methyl-1H-pyrazol-5-yl)-2-[(1S)-2-(diethylamino)-1-(3-fluorobenzyl)ethyl]isoindolin-1-one | 455.0 |

(structure shown with R²-N-R³ substituent on isoindolinone core bearing 4-chloro-1-methylpyrazole and 3-fluorobenzyl groups)

Example 40

2-[(1S)-2-amino-1-(3,5-difluorobenzyl)ethyl]-5-(1-methyl-1H-pyrazol-5-yl)isoindolin-1-one

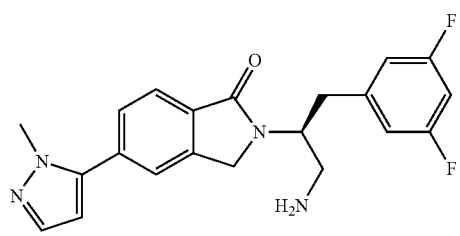 [SMILES: Cn1nccc1-c1ccc2c(c1)CN([C@H](CN)Cc1cc(F)cc(F)c1)C2=O]

Step A: tert-butyl[(1S)-1-(3,5-difluorobenzyl)-2-hydroxyethyl]carbamate

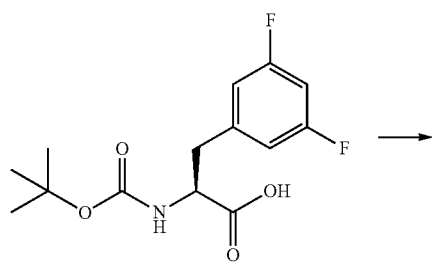

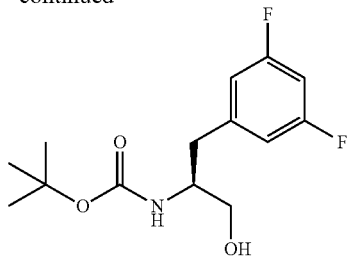

To a solution of (2S)-2-[(tert-butoxycarbonyl)amino]-3-(3,5-difluorophenyl)propanoic acid [Aldrich] (3.00 g, 9.96 mmol) in tetrahydrofuran (30 mL) at 0° C. was added 1.0 M borane-THF complex in tetrahydrofuran (32 mL, 32 mmol). The reaction mixture was stirred at room temperature for 3 hrs, and then cooled with an ice bath, quenched with AcOH:MeOH (1:5, 10 mL), and partitioned between saturated aqueous NaHCO₃ solution and dichloromethane (DCM). The aqueous phase was then extracted several times with DCM. The combined organic fractions were dried over Na₂SO₄ and concentrated under reduced pressure. The residue was used directly for the next reaction. LCMS (ES) m/e 288.1 (M+H)⁺.

Step B: 2-[(2S)-2-amino-3-(3,5-difluorophenyl)propyl]-1H-isoindole-1,3(2H)-dione [1.0]-hydrogen chloride

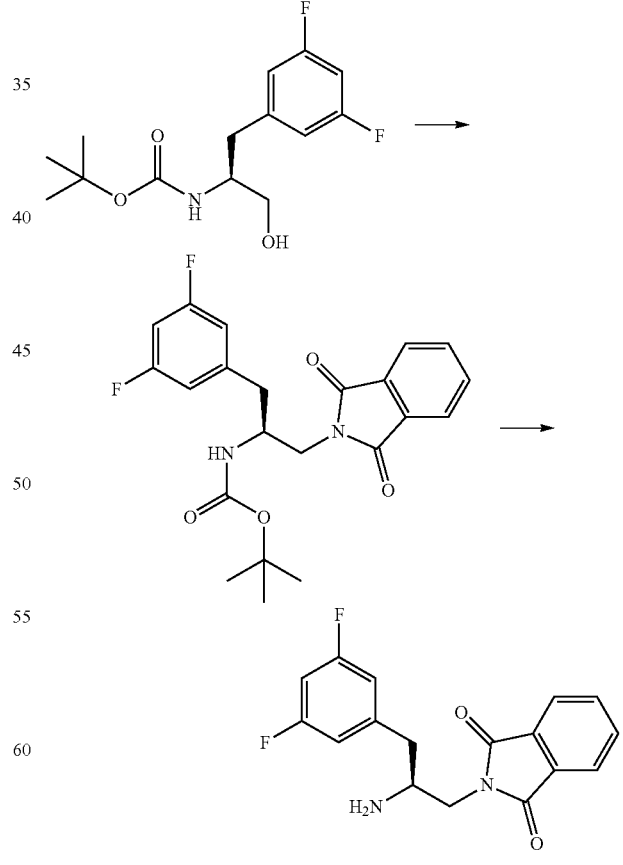

To a solution of tert-butyl[(1S)-1-(3,5-difluorobenzyl)-2-hydroxyethyl]carbamate (9.40 g, 32.8 mmol), triphenylphosphine (9.15 g, 34.9 mmol) and phthalimide (5.14 g, 34.9 mmol) in tetrahydrofuran (100 mL) at room temperature was added diethyl azodicarboxylate (17.9 mL, 45.4 mmol). The reaction was stirred at room temperature for 2 hr and then concentrated under reduced pressure. The residue was purified by combi-flash chromatography eluted with EtOAc/hexane (0-40%) to give the desired intermediate. LCMS found: 417.1 (M+H)$^+$.

To the solution of the above purified intermediate in methanol (20 mL) was added 4.0 M hydrogen chloride in dioxane (30 mL, 100 mmol). The mixture was stirred at room temperature for 2 h and then concentrated under reduced pressure to give 3.1 g (26% total yield for the two steps) of the final product, 2-[(2S)-2-amino-3-(3,5-difluorophenyl)propyl]-1H-isoindole-1,3(2H)-dione [1.0]-hydrogen chloride, as white solid. LC/MS found: 317.0 (M+H)$^+$.

Step C: 2-[(2S)-2-(5-bromo-1-oxo-1,3-dihydro-2H-isoindol-2-yl)-3-(3,5-difluorophenyl)propyl]-1H-isoindole-1,3(2H)-dione

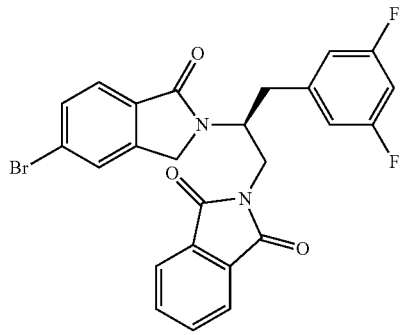

A solution of methyl 4-bromo-2-(bromomethyl)benzoate (1.34 g, 4.34 mmol), 2-[(2S)-2-amino-3-(3,5-difluorophenyl)propyl]-1H-isoindole-1,3(2H)-dione [1.0]-hydrogen chloride (1.32 g, 3.74 mmol) and N,N-diisopropylethylamine (2.06 mL, 11.8 mmol) in 1-butanol (8 mL) was stirred at 140° C. for 2 h under microwave irradiation. After the reaction mixture was concentrated under reduced pressure, the residue was dissolved in water (30 mL) and EtOAc (30 mL). The organic phase was separated and the aqueous layer was extracted with EtOAc (2×30 mL). The combined organic phases were washed with water, brine and dried over Na$_2$SO$_4$, filtered and concentrated under reduced pressure. The residue was purified by combi-flash chromatography eluted with EtOAc/hexane (10-60%). The purification gave 1.05 g (55.1% yield) of the final product as off-white solid. LC/MS found: 510.9 (M+H)$^+$.

Step D: 2-[(2S)-2-[5-(1-methyl-1H-pyrazol-5-yl)-1-oxo-1,3-dihydro-2H-isoindol-2-yl]-3-(3,5-di fluorophenyl)propyl]-1H-isoindole-1,3(2H)-dione

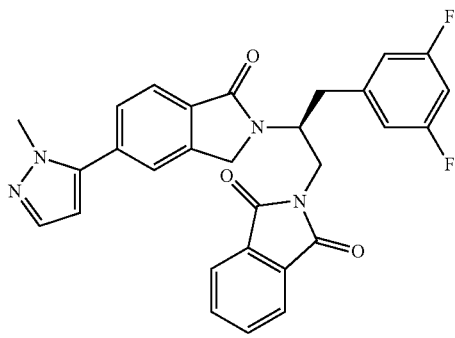 [SMILES: Cn1nccc1-c1ccc2c(c1)CN([C@@H](Cc1cc(F)cc(F)c1)CN1C(=O)c3ccccc3C1=O)C2=O]

A mixture of 1-methyl-5-(4,4,5,5-tetramethyl-1,3,2-dioxaborolan-2-yl)-1H-pyrazole (0.557 g, 2.68 mmol), bis(tri-t-butylphosphine)palladium (0.114 g, 0.223 mmol), 2-[(2S)-2-(5-bromo-1-oxo-1,3-dihydro-2H-isoindol-2-yl)-3-(3,5-difluorophenyl)propyl]-1H-isoindole-1, 3(2H)-dione (1.05 g, 2.06 mmol) and N,N-diisopropylethylamine (1.16 mL, 6.69 mmol) in 1,4-dioxane (12 mL, 150 mmol) and water (0.60 mL, 33 mmol) was stirred under microwave at 110° C. for 15 minutes. The reaction mixture was filtered through a pad of celite and the filtrate was concentrated under reduced pressure. The residue was purified by combi-flash chromatography eluted with EtOAc/hexane (30-100%) to give 0.72 g (68.4% yield) of the desired product. LCMS found: 513.1 (M+H)$^+$.

Step E: 2-[(1S)-2-amino-1-(3,5-difluorobenzyl) ethyl]-5-(1-methyl-1H-pyrazol-5-yl)isoindolin-1-one The product of Step D (0.72 g, 1.41 mmol) was dissolved in methanol (4 mL) and tetrahydrofuran (4 mL). To the resulting solution was added hydrazine (2 mL, 60 mmol). The solution was stirred at 50° C. for 2 h. The reaction mixture was concentrated under reduced pressure and the residue was purified by combi-flash chromatography eluting with MeOH/EtOAc (20-60%). The product was further purified by prep.-LC/MS (pH=10). The purification afforded 210 mg (39.0% yield) of the final product as a white solid. LC/MS found: 383.1 (M+1)$^+$; $^1$H NMR (300 MHz, DMSO-d$_6$) δ: 7.9 (d, J=13.8 Hz, 2H), 7.58 (dd, J$^1$=7.9 Hz, J$^2$=1.1 Hz, 1H), 7.48 (d, J=1.9 Hz, 1H), 6.96 (m, 3H), 6.45 (d, J=1.9 Hz, 1H), 4.47 (s, 2H), 4.41 (m, 1H), 3.86 (s, 3H), 3.04 (dd, J$^1$=14.3 Hz, J$^2$=4.8 Hz, 1H), 2.89 (dd, J$^1$=14.0 Hz, J$^2$=3.9 Hz, 1H), 2.85 (d, J=6.80 Hz, 2H).

Example 41

2-[(1S)-2-amino-1-(3,5-difluorobenzyl)ethyl]-5-(4-chloro-1-methyl-1H-pyrazol-5-yl)isoindolin-1-one

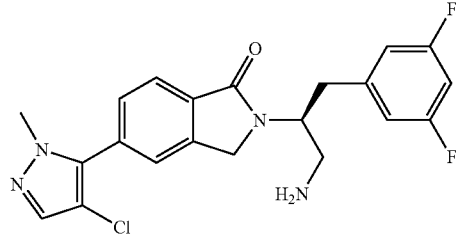 [SMILES: Cn1ncc(Cl)c1-c1ccc2c(c1)CN([C@H](CN)Cc1cc(F)cc(F)c1)C2=O]

The title compound was prepared as a white solid according to Example 40, except starting with 4-chloro-1-methyl-5-(4,4,5,5-tetramethyl-1,3,2-dioxaborolan-2-yl)-1H-pyrazole [prepared in Intermediate 1] instead of 1-methyl-5-(4,4,5,5-tetramethyl-1,3,2-dioxaborolan-2-yl)-1H-pyrazole. LC-MS (ES) m/z 417.1 (M+H)$^+$.

Example 42

2-[(1S)-2-amino-1-(3,5-difluorobenzyl)ethyl]-5-(4-methyl-1-methyl-1H-pyrazol-5-yl)isoindolin-1-one

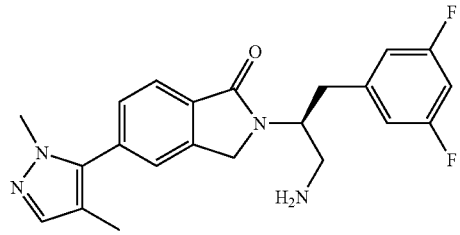 [SMILES: Cc1cnn(C)c1-c1ccc2c(c1)CN([C@H](CN)Cc1cc(F)cc(F)c1)C2=O]

The title compound was prepared as a white solid according to Example 40, except starting with 4-methyl-1-methyl-5-(4,4,5,5-tetramethyl-1,3,2-dioxaborolan-2-yl)-1H-pyrazole [prepared in Intermediate 2] instead of 1-methyl-5-(4,4,5,5-tetramethyl-1,3,2-dioxaborolan-2-yl)-1H-pyrazole. LC-MS (ES) m/z 397.1 (M+H)$^+$; $^1$H NMR (400 MHz, CD$_3$OD) δ: 7.84 (d, J=7.9 Hz, 1H), 7.57 (s, 1H), 7.48 (d, J=7.9 Hz, 1H), 7.38 (s, 1H), 6.88 (m, 2H), 6.71 (m, 1H), 4.61 (m, 1H), 4.51 (d, J=12.17 Hz, 2H), 3.73 (s, 3H), 3.08 (m, 4H), 2.01 (s, 3H).

Example 43

2-[(1S)-2-amino-1-(3,5-difluorobenzyl)ethyl]-5-(4-methoxymethyl-1-methyl-1H-pyrazol-5-yl)isoindolin-1-one

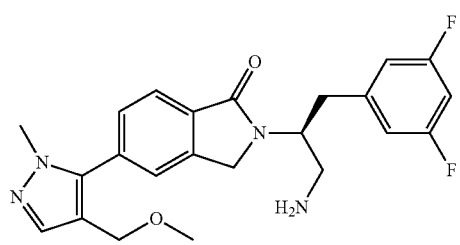 [SMILES: COCc1cnn(C)c1-c1ccc2c(c1)CN([C@H](CN)Cc1cc(F)cc(F)c1)C2=O]

The title compound was prepared as a white solid according to Example 40, except starting with 4-methoxymethyl-1-methyl-5-(4,4,5,5-tetramethyl-1,3,2-dioxaborolan-2-yl)-1H-pyrazole [prepared in Intermediate 3] instead of 1-methyl-5-(4,4,5,5-tetramethyl-1,3,2-dioxaborolan-2-yl)-1H-pyrazole. LC-MS found: 427.1 (M+H)$^+$; $^1$H NMR (400 MHz, DMSO-d$_6$) δ: 7.71 (d, J=8.00 Hz, 1H), 7.65 (s, 1H), 7.54 (s, 1H), 7.52 (dd, J$^1$=8.00 Hz, J$^2$=1.20 Hz, 1H), 6.97 (m, 3H), 4.50 (s, 2H), 4.43 (m, 1H), 4.12 (s, 2H), 3.75 (s, 3H), 3.16 (s, 3H), 3.03 (m, 1H), 2.90 (m, 1H), 2.81 (d, J=6.80 Hz, 2H).

Example 44

2-[(1S)-2-amino-1-(3,5-difluorobenzyl)ethyl]-5-(4-ethoxymethyl-1-methyl-1H-pyrazol-5-yl)isoindolin-1-one

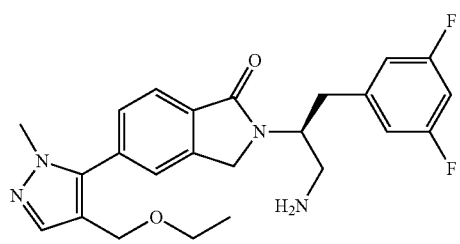

The title compound was prepared as a white solid according to Example 40, except starting with 4-ethoxymethyl-1-methyl-5-(4,4,5,5-tetramethyl-1,3,2-dioxaborolan-2-yl)-1H-pyrazole [prepared in Intermediate 4] instead of 1-methyl-5-(4,4,5,5-tetramethyl-1,3,2-dioxaborolan-2-yl)-1H-pyrazole. LC-MS found: 441.1 (M+H)$^+$; $^1$H NMR (500 MHz, DMSO-d$_6$) δ ppm 7.72 (d, J=7.8 Hz, 1H), 7.66 (s, 1H), 7.54-7.52 (m, 1H), 7.53 (s, 1H), 7.01-6.88 (m, 3H), 4.50 (s, 2H), 4.47-4.36 (m, 1H), 4.17 (s, 2H), 3.76 (s, 3H), 3.37 (q, J=7.0 Hz, 2H), 3.10-3.01 (m, 1H), 2.96-2.88 (m, 1H), 2.83 (d, J=6.8 Hz, 2H), 1.06 (t, J=7.0 Hz, 3H).

Example 45

2-[(1S)-2-amino-1-(3,5-difluorobenzyl)ethyl]-5-[4-(2-propoxymethyl)-1-methyl-1H-pyrazol-5-yl]isoindolin-1-one

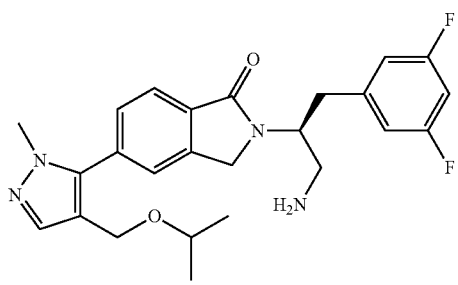 [SMILES: CC(C)OCc1cnn(C)c1-c1ccc2c(c1)CN([C@H](CN)Cc1cc(F)cc(F)c1)C2=O]

The title compound was prepared as a white solid according to Example 40, except starting with 4-(2-propoxymethyl)-1-methyl-5-(4,4,5,5-tetramethyl-1,3,2-dioxaborolan-2-yl)-1H-pyrazole [prepared in Intermediate 5] instead of 1-methyl-5-(4,4,5,5-tetramethyl-1,3,2-dioxaborolan-2-yl)-1H-pyrazole. LC-MS found: 455.1 (M+H)$^+$; $^1$H NMR (400 MHz, DMSO-d$_6$) of example: 7.75-7.66 (m, 2H), 7.56 (d, J=7.7 Hz, 1H), 7.52 (s, 1H), 7.04-6.87 (m, 3H), 4.49 (m, 3H), 4.16 (s, 2H), 3.76 (s, 3H), 3.53 (m, 1H), 3.15-2.68 (m, 4H), 1.02 (d, J=8.0 Hz, 6H).

Example 46

2-[(1S)-2-amino-1-(3,5-difluorobenzyl)ethyl]-5-[4-(1-propoxymethyl)-1-methyl-1H-pyrazol-5-]isoindolin-1-one

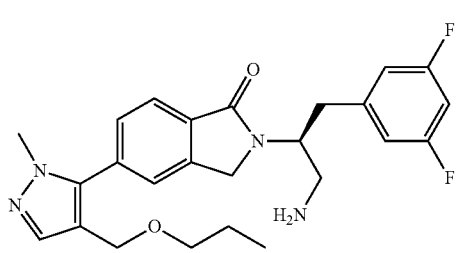

The title compound was prepared as a white solid according to Example 40, except starting with 4-(1-propoxymethyl)-1-methyl-5-(4,4,5,5-tetramethyl-1,3,2-dioxaborolan-2-yl)-1H-pyrazole [prepared in Intermediate 6] instead of 1-methyl-5-(4,4,5,5-tetramethyl-1,3,2-dioxaborolan-2-yl)-1H-pyrazole. LC-MS found: 455.1 (M+H)$^+$; $^1$H NMR (300 MHz, DMSO-d$_6$) of example: 7.70 (m, 2H), 7.55 (m, 2H), 6.97 (m, 3H), 4.46 (m, 3H), 4.16 (s, 2H), 3.76 (s, 3H), 3.38 (t, J=6.0 Hz, 2H), 2.91 (m, 4H), 1.45 (m, 2H), 0.79 (t, J=9.0 Hz, 3H).

Example 47

2-[(1S)-2-amino-1-(3,5-difluorobenzyl)ethyl]-5-[4-(cyclobutoxymethyl)-1-methyl-1H-pyrazol-5-yl]isoindolin-1-one

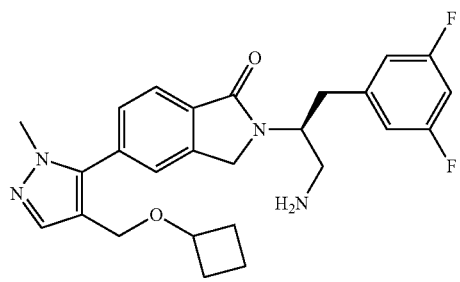 [SMILES: Cn1ncc(COC2CCC2)c1-c1ccc2c(c1)CN([C@H](CN)Cc1cc(F)cc(F)c1)C2=O]

The title compound was prepared as a white solid according to Example 40, except starting with 4-(cyclobutoxymethyl)-1-methyl-5-(4,4,5,5-tetramethyl-1,3,2-dioxaborolan-2-yl)-1H-pyrazole [prepared in Intermediate 7] instead of 1-methyl-5-(4,4,5,5-tetramethyl-1,3,2-dioxaborolan-2-yl)-1H-pyrazole. LC-MS found: 467.1 (M+H)$^+$; $^1$H NMR (300 MHz, DMSO-d$_6$) of example: 7.71 (m, 2H), 7.55 (m, 2H), 6.97 (m, 3H), 4.47 (m, 3H), 4.07 (s, 2H), 3.86 (m, 1H), 3.76 (s, 3H), 2.92 (m, 4H), 2.01 (m, 2H), 1.52 (m, 4H).

Example 48

2-[(1S)-2-amino-1-(3,5-difluorobenzyl)ethyl]-5-[4-(cyclopropylmethoxymethyl)-1-methyl-1H-pyrazol-5-yl]isoindolin-1-one

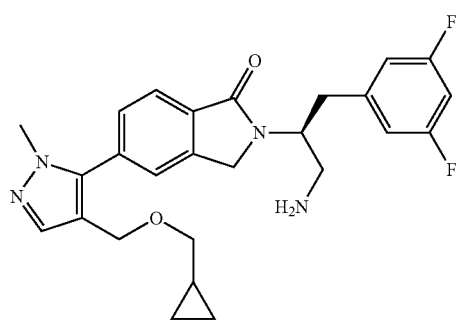 [SMILES: Cn1ncc(COCC2CC2)c1-c1ccc2c(c1)CN([C@H](CN)Cc1cc(F)cc(F)c1)C2=O]

The title compound was prepared as a white solid according to Example 40, except starting with 4-(cyclopropylmethoxymethyl)-1-methyl-5-(4,4,5,5-tetramethyl-1,3,2-dioxaborolan-2-yl)-1H-pyrazole [prepared in Intermediate 8] instead of 1-methyl-5-(4,4,5,5-tetramethyl-1,3,2-dioxaborolan-2-yl)-1H-pyrazole. LC-MS found: 467.1 (M+H)$^+$;

Example 49

2-[(1S)-2-amino-1-(3,5-difluorobenzyl)ethyl]-5-[4-(methylthio)methyl-1-methyl-1H-pyrazol-5-yl]isoindolin-1-one

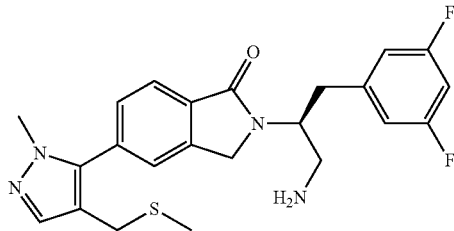 [SMILES: CSCc1cnn(C)c1-c1ccc2c(c1)CN([C@H](CN)Cc1cc(F)cc(F)c1)C2=O]

The title compound was prepared as a white solid according to Example 40, except starting with 4-(methylthio)methyl-1-methyl-5-(4,4,5,5-tetramethyl-1,3,2-dioxaborolan-2-yl)-1H-pyrazole [prepared in Intermediate 11] instead of 1-methyl-5-(4,4,5,5-tetramethyl-1,3,2-dioxaborolan-2-yl)-1H-pyrazole. LC-MS found: 443.1 (M+H)$^+$.

Example 50

2-[(1S)-2-amino-1-(3,5-difluorobenzyl)ethyl]-5-[4-(ethylthio)methyl-1-methyl-1H-pyrazol-5-yl]isoindolin-1-one

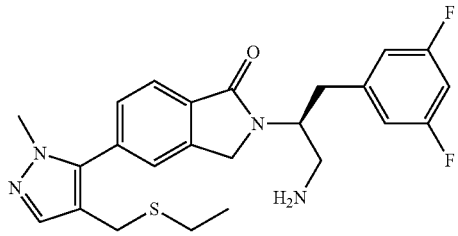 [SMILES: CCSCc1cnn(C)c1-c1ccc2c(c1)CN([C@H](CN)Cc1cc(F)cc(F)c1)C2=O]

The title compound was prepared as a white solid according to Example 40, except starting with 4-(ethylthio)methyl-1-methyl-5-(4,4,5,5-tetramethyl-1,3,2-dioxaborolan-2-yl)-1H-pyrazole [prepared in Intermediate 10] instead of 1-methyl-5-(4,4,5,5-tetramethyl-1,3,2-dioxaborolan-2-yl)-1H-pyrazole. LC-MS found: 457.1 (M+H)$^+$; $^1$H NMR (400 MHz, DMSO) δ 7.72 (d, J=7.8 Hz, 1H), 7.67 (s, 1H), 7.53 (Q, J=9.0 Hz, 1H), 7.48 (s, 1H), 7.01-6.88 (m, 3H), 4.50 (s, 2H), 4.47-4.36 (m, 1H), 3.75 (s, 3H), 3.51 (s, 2H), 3.17 (q, J=7.0 Hz, 1H), 2.84-2.93 (m, 1H), 2.82 (d, J=7.1 Hz 1H), 2.38 (q, J=7.2 Hz, 2H), 1.06 (t, J=7.2 Hz, 3H).

Example 51

2-[(1S)-2-amino-1-(3,5-difluorobenzyl)ethyl]-5-(4-fluoro-1-methyl-1H-pyrazol-5-yl)isoindolin-1-one

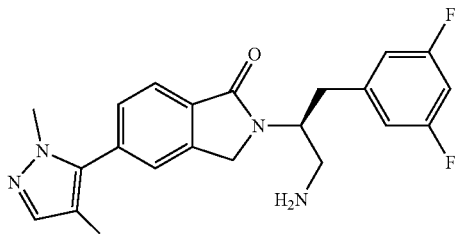

The title compound was prepared as a white solid according to Example 11. LC-MS found: 401.1 (M+H)+; 1H NMR (300 MHz, DMSO-$d_6$) δ ppm: 7.83 (d, J=8.1 Hz, 1H), 7.42 (d, J=8.0 Hz, 2H), 7.35 (d, J=4.5 Hz, 1H), 6.69 (d, J=6.0 Hz, 2H), 6.56 (m, 1H), 4.52 (m, 1H), 4.31 (d, J=3.9 Hz, 2H), 3.77 (s, 3H), 3.02 (d, J=6.6 Hz, 2H), 2.96 (d, J=7.5 Hz, 2H).

Example 52

2-[(1S)-2-amino-1-(3,5-difluorobenzyl)ethyl]-5-(4-bromo-1-methyl-1H-pyrazol-5-yl)isoindolin-1-one

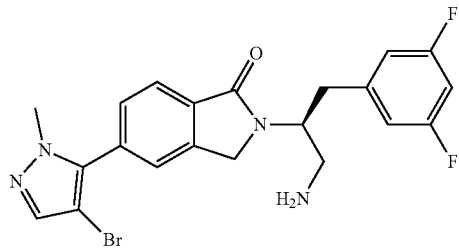 [SMILES: Cn1ncc(Br)c1-c1ccc2c(c1)CN([C@H](CN)Cc1cc(F)cc(F)c1)C2=O]

The title compound was prepared as a white solid according to Example 12. LC-MS found: 461.1 (M+H)+; 1H NMR (400 MHz, CD$_3$OD) δ: 7.85 (d, J=7.9 Hz, 1H), 7.66 (s, 1H), 7.58 (s, 1H), 7.56 (d, J=7.9 Hz, 1H), 6.87 (d, J=8.4 Hz, 2H), 6.73 (m, 1H), 4.63 (m, 1H), 4.53 (d, J=11.5 Hz, 2H), 3.14 (m, 4H).

Example 53

2-[(1S)-2-amino-1-(3,5-difluorobenzyl)ethyl]-5-(4-cyano-1-methyl-1H-pyrazol-5-yl)isoindolin-1-one

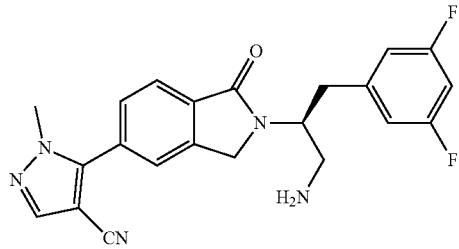 [SMILES: Cn1ncc(C#N)c1-c1ccc2c(c1)CN([C@H](CN)Cc1cc(F)cc(F)c1)C2=O]

Step A: 2-[(2S)-2-[5-(4-bromo-1-methyl-1H-pyrazol-5-yl)-1-oxo-1,3-dihydro-2H-isoindol-2-yl]-3-(3,5-difluorophenyl)propyl]-1H-isoindole-1,3(2H)-dione

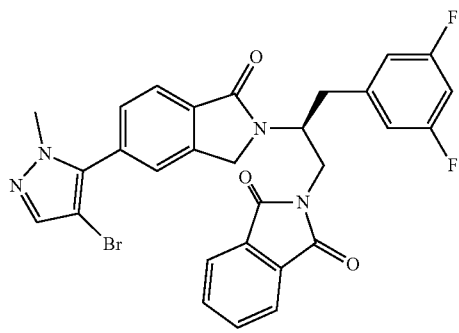 [SMILES: Cn1ncc(Br)c1-c1ccc2c(c1)CN([C@@H](Cc1cc(F)cc(F)c1)CN1C(=O)c3ccccc3C1=O)C2=O]

To a solution of 2-{(2S)-3-(3,5-difluorophenyl)-2-[5-(1-methyl-1H-pyrazol-5-yl)-1-oxo-1,3-dihydro-2H-isoindol-2-yl]propyl}-1H-isoindole-1,3(2H)-dione (200.0 mg, 0.39 mmol) [prepared in Example 40] in tetrahydrofuran (5 mL) was added N-bromosuccinimide (72.0 mg, 0.404 mmol). The solution was stirred at room temperature for 1 h and then concentrated under reduced pressure. The residue was purified by combi-flash chromatography eluting with EtOAc/hexane (50-100%). The purification afforded 177 mg (77% yield) of the desired product as white solid. LC/MS found: 591.0 (M+1)+.

Step B: 2-[(1S)-2-amino-1-(3,5-difluorobenzyl)ethyl]-5-(4-cyano-1-methyl-1H-pyrazol-5-yl)isoindolin-1-one A mixture of zinc cyanide (64.5 mg, 0.549 mmol), 2-[(2S)-2-[5-(4-bromo-1-methyl-1H-pyrazol-5-yl)-1-oxo-1,3-dihydro-2H-isoindol-2-yl]-3-(3,5-difluorophenyl)propyl]-1H-isoindole-1,3(2H)-dione (105.0 mg, 0.178 mmol) [prepared in Example 7] and tetrakis(triphenylphosphine)palladium(0) (21 mg, 0.018 mmol) in N-methylpyrrolidinone (1 mL) in a sealed tube was microwaved at 190° C. for 1 h. The reaction mixture was filtered and the filtrate was diluted with EtOAc (50 mL). The organic phase was washed with water, brine and concentrated under reduced pressure. Direct purification on prep.—HPLC (pH=10) gave the desired intermediate as white solid. LC-MS found: 538.1 (M+H)+.

The above intermediate was dissolved in methanol (2 mL), tetrahydrofuran (2 mL) and hydrazine (0.2 mL, 6 mmol). The solution was stirred at 50° C. for 2 h. Direct purification on prep.—HPLC (pH=10) gave 6.3 mg of the desired product as white solid. LC/MS found: 408.1 (M+1)+; 1H NMR (400 MHz, CD$_3$OD) δ: 7.98 (s, 1H), 7.91 (d, J=7.9 Hz, 1H), 7.69 (dd, J1=8.2 Hz, J2=1.5 Hz, 1H), 6.88 (dd, J1=8.5 Hz, J2=2.1 Hz, 2H), 6.73 (m, 2H), 4.47 (d, J=2.40 Hz, 2H), 4.90 (s, 3H), 4.61 (m, 1H), 4.56 (d, J=13.3 Hz, 1H), 3.89 (s, 2H), 3.15 (m, 3H).

Example 54

2-[(1S)-2-amino-1-(3,5-difluorobenzyl)ethyl]-5-[4-(3-hydroxy-3-methylbut-1-yn-1-yl)-1-methyl-1H-pyrazol-5-yl]isoindolin-1-one

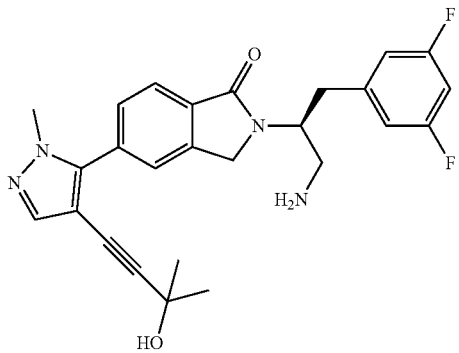 [SMILES: Cn1ncc(C#CC(C)(C)O)c1-c1ccc2c(c1)CN([C@H](CN)Cc1cc(F)cc(F)c1)C2=O]

A mixture of 2-{(2S)-3-(3,5-difluorophenyl)-2-[5-(4-iodo-1-methyl-1H-pyrazol-5-yl)-1-oxo-1,3-dihydro-2H-isoindol-2-yl]propyl}-1H-isoindole-1,3(2H)-dione [prepared in Example 40] (100 mg, 0.2 mmol), 2-methyl-3-butyn-2-ol (0.06 g, 0.7 mmol), copper(I) iodide (20 mg, 0.1 mmol), bis(triphenylphosphine)palladium(II) chloride (20.0 mg, 0.0285 mmol) and N,N-diisopropylethylamine (0.2 mL) in a sealed tube was stirred 65° C. for 3 hours. Direct purification on preparative HPLC gave the desired Suzuki coupling product. LC-MS found: 595.1 (M+H)+.

The white powder intermediate was dissolved in THF and MeOH containing 20% hydrazine and the resulting mixture was stirred at room temperature for 4 hrs. Direct purification by preparative HPLC afforded the desired final product. LC-MS found: 365.1 (M+H)+; $^1$H NMR (500 MHz, DMSO-$d_6$) δ ppm 7.78 (s, 1H), 7.73 (d, J=7.9 Hz, 1H), 7.67 (dd, J=7.8, 1.2 Hz, 1H), 7.65 (s, 1H), 6.99-6.91 (m, 3H), 5.26 (s, 1H), 4.48 (s, 2H), 4.47-4.40 (m, 1H), 3.84 (s, 3H), 3.07 (dd, J=14.3, 5.0 Hz, 1H), 2.94 (dd, J=14.3, 10.1 Hz, 1H), 2.84 (d, J=6.9 Hz, 2H), 1.34 (s, 3H), 1.33 (s, 3H).

Example 55

2-[(1S)-2-amino-1-benzyl-ethyl]-5-(1-methyl-1H-pyrazol-5-yl)isoindolin-1-one

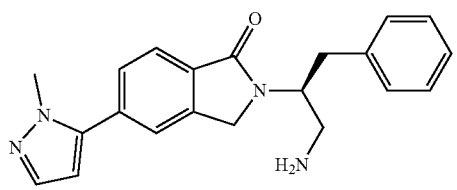 [SMILES: Cn1nccc1-c1ccc2c(c1)CN([C@H](CN)Cc1ccccc1)C2=O]

Method A

Step A: 2-[(1S)-2-amino-1-benzyl-ethyl]-5-bromo-isoindolin-1-one

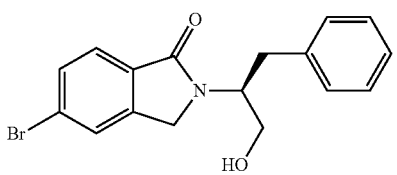 [SMILES: O=C1c2ccc(Br)cc2CN1[C@H](CO)Cc1ccccc1]

A solution of methyl 4-bromo-2-(bromomethyl)benzoate (1.0 g, 3.24 mmol), (2S)-2-amino-3-phenyl-1-propanol (0.49 g, 3.24 mmol) and N,N-diisopropylethylamine (2.06 mL, 11.8 mmol) in 1-butanol (8 mL) was stirred at 140° C. for 2 h under microwave. After the reaction mixture was concentrated under reduced pressure, the residue was dissolved in water (20 mL) and EtOAc (20 mL). The organic phase was separated and the aqueous layer was extracted with EtOAc (2×30 mL). The combined organic phases were washed with water, brine and dried over $Na_2SO_4$, filtered and concentrated under reduced pressure. The residue was purified by combi-flash chromatography eluted with MeOH/EtOAc (0-5%) to give 0.8 g (71% yield) of the final product as off-white solid. LC/MS found: 346.0 (M+H)+.

Step B: 2-[(2S)-2-(5-bromo-1-oxo-1,3-dihydro-2H-isoindol-2-yl)-3-phenyl)propyl]-1H-isoindole-1,3 (2H)-dione

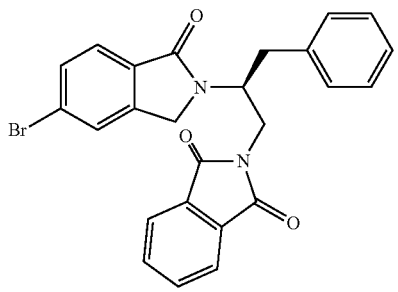 [SMILES: O=C1c2ccccc2C(=O)N1C[C@H](Cc1ccccc1)N1Cc2cc(Br)ccc2C1=O]

To a solution of triphenylphosphine (4.54 g, 17.3 mmol), phthalimide (2.8 g, 19 mmol) and diisopropyl azodicarboxylate (9.4 mL, 19 mmol) in tetrahydrofuran (50 mL) was added 2-[(1S)-1-benzyl-2-hydroxyethyl]-5-bromoisoindolin-1-one (6.0 g, 17 mmol) dropwise at 0° C. under $N_2$. The reaction mixture was stirred 0° C. for 30 min, warmed up to room temperature, and then stirred at room temperature for 60 min. The reaction was quenched with 3 mL of water, concentrated under reduced pressure. The residue was purified by combi-flash chromatography, eluted with 60% EtOAc in hexane to give 5.6 g (68% yield) of the desired product as off-white solid. LC-MS found: 475.1 (M+H)+.

Step C: 2-[(1S)-2-amino-1-benzylethyl]-5-1-methyl-1H-pyrazol-5-yl)isoindolin-1-one

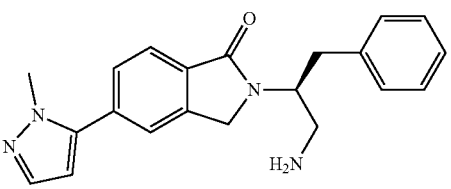 [SMILES: Cn1nccc1-c1ccc2c(c1)CN([C@H](CN)Cc1ccccc1)C2=O]

A mixture of 1-methyl-5-(4,4,5,5-tetramethyl-1,3,2-dioxaborolan-2-yl)-1H-pyrazole (1.5 g, 6.3 mmol), 2-[(2S)-2-(5-bromo-1-oxo-1,3-dihydro-2H-isoindol-2-yl)-3-phenylpropyl]-1H-isoindole-1,3(2H)-dione (1.5 g, 3.2 mmol), bis(tri-t-butylphosphine)palladium (300 mg, 0.6 mmol) and water (0.5 mL) in 1,4-dioxane (5.0 mL) and water (0.5 mL) was stirred at 110° C. for 40 min under microwave. Direct purification on prep.—HPLC (pH=10) afforded 0.45 g (28.1% yield) of the desired intermediate as white solid. LC-MS found: 477.1 (M+H)+.

The above pure intermediate was dissolved in methanol (4 mL), tetrahydrofuran (4 mL) and hydrazine (0.8 mL). The resulting reaction mixture was stirred at 50° C. for 2 h. Direct purification on prep.—HPLC (pH=10) afforded 151 mg (45.1% yield) of the desired product as white solid. LC-MS found: 347.1 (M+H)+.

Method B

Step A: tert-butyl[(2S)-2-(5-bromo-1-oxo-1,3-dihydro-2H-isoindol-2-yl)-3-phenylpropyl]carbamate

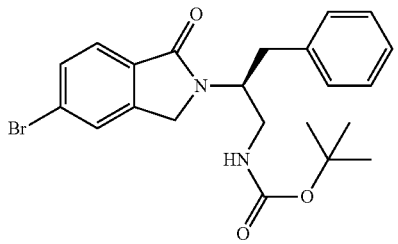 [SMILES: CC(C)(C)OC(=O)NC[C@H](Cc1ccccc1)N1Cc2cc(Br)ccc2C1=O]

Step B: 2-[(1S)-2-amino-1-benzylethyl]-5-(1-methyl-1H-pyrazol-5-yl)isoindolin-1-one

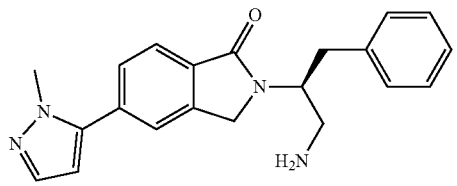

A mixture of tert-butyl[(2S)-2-(5-bromo-1-oxo-1,3-dihydro-2H-isoindol-2-yl)-3-phenylpropyl]carbamate (95.78 mg, 0.2151 mmol), 1-methyl-5-(4,4,5,5-tetramethyl-1,3,2-dioxaborolan-2-yl)-1H-pyrazole (47 mg, 0.23 mmol), N,N-diisopropylethylamine (0.11 mL, 0.63 mmol), and bis(tri-t-butylphosphine)palladium (0.011 g, 0.021 mmol) in 1,4-dioxane (4 mL) and water (0.2 mL) was stirred at 110° C. for 40 mins under microwave. Direct purification by combi-flash chromatography afforded 65 mg (68% yield) of the desired intermediate. LC-MS found: 347.1 (M−Boc)+.

The above intermediate (65 mg, 0.15 mmol) was dissolved in 4 M HCl dioxane (2 mL, 8 mmol) and THF (2.0 mL). The resulting mixture was stirred at room temperature for 2 h. Direct purification on prep. HPLC afforded 17 mg (33% yield) of the desired final product. LC-MS found: 347.1 (M+H)+.

Example 56

2-[(1S)-2-amino-1-benzyl-ethyl]-5-(4-chloro-1-methyl-1H-pyrazol-5-yl)isoindolin-1-one

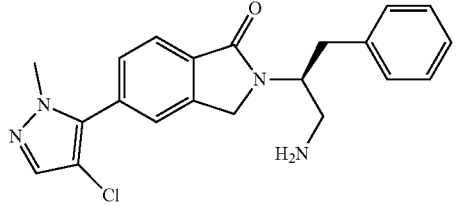

The title compound was prepared as a white solid according to Example 55 (Method A), except starting with 4-chloro-1-methyl-5-(4,4,5,5-tetramethyl-1,3,2-dioxaborolan-2-yl)-1H-pyrazole [prepared in Intermediate 1] instead of 1-methyl-5-(4,4,5,5-tetramethyl-1,3,2-dioxaborolan-2-yl)-1H-pyrazole. LC-MS found: 399.1 (M+H)+; 1H NMR (300 MHz, DMSO-$d_6$) δ: 7.73 (d, J=7.8 Hz, 1H), 7.69 (s, 1H), 7.68 (s, 1H), 7.56 (d, J=1.4 Hz, 1H), 7.4 (d, J=1.5 Hz, 1H), 7.21 (d, J=1.4 Hz, 1H), 7.20 (s, 2H), 7.12 (m, 1H), 4.47 (d, J=7.4 Hz, 2H), 4.42 (m, 1H), 3.76 (s, 3H), 3.01 (dd, J=5.9 Hz, 1H), 2.98 (d, J=9.3 Hz, 1H), 2.81 (d, J=6.9 Hz, 2H).

Example 57

2-[(1S)-2-amino-1-benzyl-ethyl]-5-(4-bromo-1-methyl-1H-pyrazol-5-yl)isoindolin-1-one

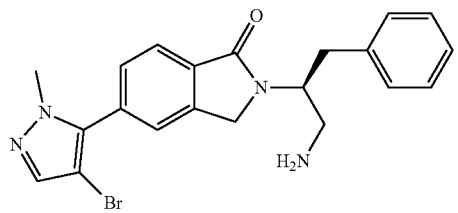 [SMILES: Cn1ncc(Cl)c1-c1ccc2c(c1)CN([C@H](CN)Cc1ccccc1)C2=O]

The title compound was prepared as a white solid according to Example 12. LC-MS found: 425.1 (M+H)+; 1H NMR (300 MHz, DMSO-$d_6$) δ: 7.73 (dd, $J^1$=7.92 Hz, $J^2$=0.62 Hz, 1H), 7.68 (s, 2H), 7.53 (dd, $J^1$=7.04 Hz, $J^2$=1.4 Hz, 1H), 7.22 (m, 4H), 7.13 (m, 1H), 4.47 (d, J=7.93 Hz, 2H), 4.41 (m, 1H), 3.76 (s, 3H), 3.03 (dd, $J^1$=14.31 Hz, $J^2$=5.8 Hz, 1H), 2.84 (dd, $J^1$=14.15 Hz, $J^2$=9.2 Hz, 1H), 2.81 (d, J=6.8 Hz, 2H).

Example 58

2-[(1S)-2-amino-1-benzyl-ethyl]-5-[4-(2-propoxymethyl)-1-methyl-1H-pyrazol-5-yl]isoindolin-1-one

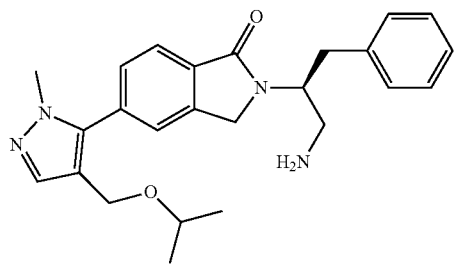 [SMILES: CC(C)OCc1cnn(C)c1-c1ccc2c(c1)CN([C@H](CN)Cc1ccccc1)C2=O]

The title compound was prepared as a white solid according to Example 55 (Method B), except starting with 4-(2-propoxymethyl)-1-methyl-5-(4,4,5,5-tetramethyl-1,3,2-dioxaborolan-2-yl)-1H-pyrazole [prepared in Intermediate 5] instead of 1-methyl-5-(4,4,5,5-tetramethyl-1,3,2-dioxaborolan-2-yl)-1H-pyrazole. LC-MS found: 419.1 (M+H)+; 1H NMR (400 MHz, DMSO-$d_6$) of example: 7.70 (m, 2H), 7.55

(m, 1H), 7.52 (s, 1H), 7.21 (m, 4H), 7.13 (m, 1H), 4.45 (m, 3H), 4.15 (s, 2H), 3.76 (s, 3H), 3.53 (m, 1H), 2.86 (m, 4H), 1.03 (d, J=5.6 Hz, 6H).

Example 59

2-[(1S)-2-amino-1-benzyl-ethyl]-5-[4-(methylthiomethyl)-1-methyl-1H-pyrazol-5-yl]isoindolin-1-one

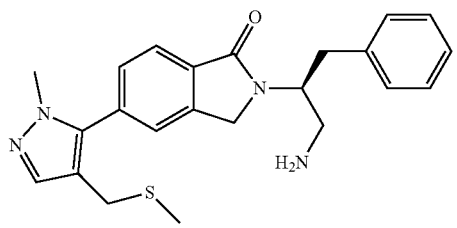 [SMILES: CSCc1cnn(C)c1-c1ccc2c(c1)CN([C@H](CN)Cc1ccccc1)C2=O]

The title compound was prepared as a white solid according to Example 55 (Method B), except starting with 4-(methylthiomethyl)-1-methyl-5-(4,4,5,5-tetramethyl-1,3,2-dioxaborolan-2-yl)-1H-pyrazole [prepared in Intermediate 11] instead of 1-methyl-5-(4,4,5,5-tetramethyl-1,3,2-dioxaborolan-2-yl)-1H-pyrazole. LC-MS found: 407.1 (M+H)+.

The following compounds listed in Table 3 were prepared by a method analogous to that for Example 55 (Method A).

TABLE 3

| Ex. # | Intermediate A | A | Compound | LC-MS (M + H)+ |
|---|---|---|---|---|
| 60 | 12 | 2-F-phenyl | 2-[2-amino-1-(2-fluorobenzyl)ethyl]-5-(4-chloro-1-methyl-1H-pyrazol-5-yl)isoindolin-1-one | 398.9 |
| 61 | 14 | 3-CF3-phenyl | 2-{2-amino-1-[3-(trifluoromethyl)benzyl]ethyl}-5-(4-chloro-1-methyl-1H-pyrazol-5-yl)isoindolin-1-one | 448.9 |
| 62 | 15 | 3-CN-phenyl | 3-{(2S)-3-amino-2-[5-(4-chloro-1-methyl-1H-pyrazol-5-yl)-1-oxo-1,3-dihydro-2H-isoindol-2-yl]propyl}benzonitrile | 405.9 |

TABLE 3-continued

| Ex. # | Intermediate A | A | Compound | LC-MS (M + H)+ |
|---|---|---|---|---|
| 63 | 16 | 4-CN-phenyl | 4-{(2S)-3-amino-2-[5-(4-chloro-1-methyl-1H-pyrazol-5-yl)-1-oxo-1,3-dihydro-2H-isoindol-2-yl]propyl}benzonitrile | 405.9 |
| 64 | 17 | 2-methoxypyridin-4-yl | 2-{(1S)-2-amino-1-[(2-methoxypyridin-4-yl)methyl]ethyl}-5-(4-chloro-1-methyl-1H-pyrazol-5-yl)isoindolin-1-one | 412.0 |
| 65 | 18 | pyridin-3-yl | 2-[(1S)-2-amino-1-(pyridin-3-ylmethyl)ethyl]-5-(4-chloro-1-methyl-1H-pyrazol-5-yl)isoindolin-1-one | 382.0 |
| 66 | 19 | pyridin-2-yl | 2-[(1S)-2-amino-1-(pyridin-2-ylmethyl)ethyl]-5-(4-chloro-1-methyl-1H-pyrazol-5-yl)isoindolin-1-one | 382.0 |
| 67 | 20 | thien-2-yl | 2-[(1S)-2-amino-1-(2-thienylmethyl)ethyl]-5-(4-chloro-1-methyl-1H-pyrazol-5-yl)isoindolin-1-one | 386.9 |
| 68 | 21 | thien-3-yl | 2-[(1S)-2-amino-1-(3-thienylmethyl)ethyl]-5-(4-chloro-1-methyl-1H-pyrazol-5-yl)isoindolin-1-one | 387.0 |

TABLE 3-continued

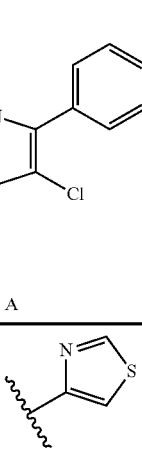

| Ex. # | Intermediate A | Compound | | LC-MS (M + H)+ |
|---|---|---|---|---|
| 69 | 22 | 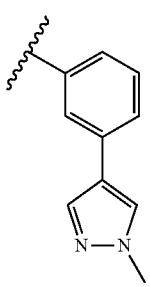 [SMILES: *c1cccc(-c2cnn(C)c2)c1] | 2-[(1S)-2-amino-1-(1,3-thiazol-4-ylmethyl)ethyl]-5-(4-chloro-1-methyl-1H-pyrazol-5-yl)isoindolin-1-one | 387.9 |
| 70 | 23 | 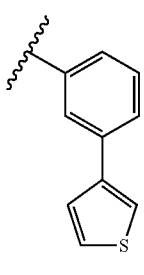 [SMILES: *c1cccc(-c2ccsc2)c1] | 2-{(1S)-2-amino-1-[3-(1-methyl-1H-pyrazol-4-yl)benzyl]ethyl}-5-(4-chloro-1-methyl-1H-pyrazol-5-yl)isoindolin-1-one | 461.0 |
| 71 | 24 | 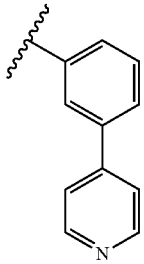 [SMILES: *c1cccc(-c2ccncc2)c1] | 2-{(1S)-2-amino-1-[3-(3-thienyl)benzyl]ethyl}-5-(4-chloro-1-methyl-1H-pyrazol-5-yl)isoindolin-1-one | 463.0 |
| 72 | 25 | 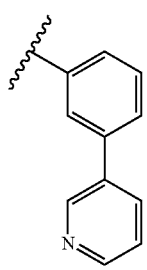 [SMILES: *c1cccc(-c2cccnc2)c1] | 2-[(1S)-2-amino-1-(3-pyridin-4-ylbenzyl)ethyl]-5-(4-chloro-1-methyl-1H-pyrazol-5-yl)isoindolin-1-one | 458.0 |

TABLE 3-continued

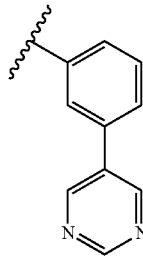

| Ex. # | Intermediate A | Compound | | LC-MS (M + H)+ |
|---|---|---|---|---|
| 73 | 26 | (3-pyridyl-benzyl image) | 2-[(1S)-2-amino-1-(3-pyridin-3-ylbenzyl)ethyl]-5-(4-chloro-1-methyl-1H-pyrazol-5-yl)isoindolin-1-one | 458.0 |
| 74 | 27 | (3-pyrimidinyl-benzyl image) | 2-[(1S)-2-amino-1-(3-pyrimidin-5-ylbenzyl)ethyl]-5-(4-chloro-1-methyl-1H-pyrazol-5-yl)isoindolin-1-one | 459.0 |

$^1$H NMR (300 MHz, DMSO-$d_6$) of Example 61 δ ppm: 7.72 (m, 1H), 7.68 (s, 1H), 7.60 (m, 2H), 7.53 (m, 2H), 7.46 (m, 2H), 4.49 (d, J=5.3 Hz, 2H), 4.46 (m, 1H), 3.76 (s, 3H), 3.10 (dd, J$^1$=14.3 Hz, J$^2$=9.3 Hz, 1H), 2.99 (dd, J$^1$=14.3 Hz, J$^2$=9.8 Hz, 1H), 2.85 (d, J=5.77 Hz, 2H).

$^1$H NMR (300 MHz, DMSO-$d_6$) of Example 63 δ ppm: 7.2 (d, J=8.9 Hz, 1H), 7.70 (d, J=2.3 Hz, 2H), 7.68 (s, 1H), 7.67 (s, 1H), 7.55 (dd, J$^1$=8.1 Hz, J$^2$=1.4 Hz, 1H), 7.41 (d, J=8.3 Hz, 2H), 4.50 (s, 2H), 4.43 (m, 1H), 3.76 (s, 3H), 3.11 (dd, J$^1$=14.8 Hz, J$^2$=4.9 Hz, 1H), 2.95 (dd, J$^1$=14.5 Hz, J$^2$=10.2 Hz, 2H).

$^1$H NMR (400 MHz, CD$_3$OD) of Example 67: δ 7.88 (d, J=8.0 Hz, 1H), 7.67 (s, 1H), 7.58 (m, 2H), 7.15 (dd, J=4.8, 1.2 Hz, 1H), 6.85 (d, J=4.8 Hz, 2H), 4.53 (m, 3H), 3.81 (s, 3H), 3.29 (m, 2H), 3.05 (m, 2H).

$^1$H NMR (300 MHz, DMSO-$d_6$) of Example 68 δ ppm: 7.5-7.8 (m, 3H), 7.56 (dd, J$^1$=1.2 Hz, J$^2$=7.9 Hz, 1H), 7.39 (dd, J$^1$=3.0 Hz, J$^2$=4.9 Hz, 1H), 7.17 (m, 1H), 6.95 (dd, J$^1$=1.2 Hz, J$^2$=4.9 Hz, 1H), 4.35-4.60 (m, 3H), 3.76 (s, 3H), 2.78-3.02 (m, 4H).

The following compounds listed in Table 4 were prepared by a method analogous to that for Example 55 (Method A).

TABLE 4

| Ex. # | Intermediate A | A | Compound | LC-MS (M+H)+ |
|---|---|---|---|---|
| 75 | 15 | 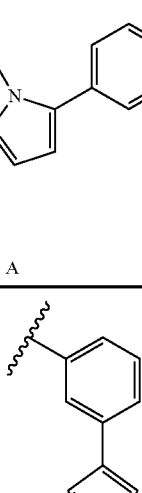 | 3-{(2S)-3-amino-2-[5-(1-methyl-1H-pyrazol-5-yl)-1-oxo-1,3-dihydro-2H-isoindol-2-yl]propyl}benzonitrile | 372.1 |
| 76 | 13 | 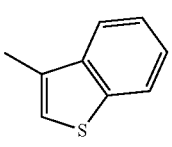 | 2-[(1S)-2-amino-1-(1-benzothien-3-ylmethyl)ethyl]-5-(1-methyl-1H-pyrazol-5-yl)isoindolin-1-one | 403.1 |
| 77 | 17 | 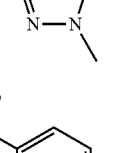 | 2-{(1S)-2-amino-1-[(2-methoxypyridin-4-yl)methyl]ethyl}-5-(1-methyl-1H-pyrazol-5-yl)isoindolin-1-one | 378.1 |
| 78 | 18 | 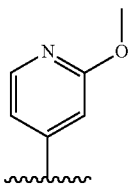 | 2-[(1S)-2-amino-1-(pyridin-3-ylmethyl)ethyl]-5-(1-methyl-1H-pyrazol-5-yl)isoindolin-1-one | 348.1 |
| 79 | 19 | 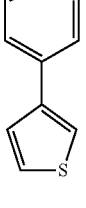 | 2-[(1S)-2-amino-1-(pyridin-2-ylmethyl)ethyl]-5-(1-methyl-1H-pyrazol-5-yl)isoindolin-1-one | 348.1 |
| 80 | 20 | 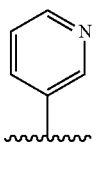 | 2-[(1S)-2-amino-1-(2-thienylmethyl)ethyl]-5-(1-methyl-1H-pyrazol-5-yl)isoindolin-1-one | 353.0 |
| 81 | 21 | 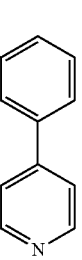 | 2-[(1S)-2-amino-1-(3-thienylmethyl)ethyl]-5-(1-methyl-1H-pyrazol-5-yl)isoindolin-1-one | 353.1 |
| 82 | 22 | 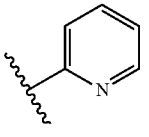 | 2-[(1S)-2-amino-1-(1,3-thiazol-4-ylmethyl)ethyl]-5-(1-methyl-1H-pyrazol-5-yl)isoindolin-1-one | 354.1 |

TABLE 4-continued

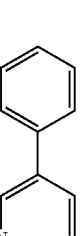

| Ex. # | Intermediate A | A | Compound | LC-MS (M+H)+ |
|---|---|---|---|---|
| 83 | 23 | 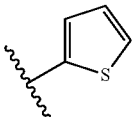 [SMILES: *c1cccs1] | 2-{(1S)-2-amino-1-[3-(1-methyl-1H-pyrazol-4-yl)benzyl]ethyl}-5-(1-methyl-1H-pyrazol-5-yl)isoindolin-1-one | 427.1 |
| 84 | 24 | 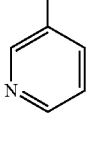 | 2-{(1S)-2-amino-1-[3-(3-thienyl)benzyl]ethyl}-5-(1-methyl-1H-pyrazol-5-yl)isoindolin-1-one | 429.1 |
| 85 | 25 | 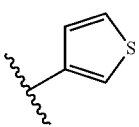 [SMILES: *c1ccsc1] | 2-[(1S)-2-amino-1-(3-pyridin-4-ylbenzyl)ethyl]-5-(1-methyl-1H-pyrazol-5-yl)isoindolin-1-one | 424.1 |
| 86 | 26 | 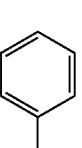 | 2-[(1S)-2-amino-1-(3-pyridin-3-ylbenzyl)ethyl]-5-(1-methyl-1H-pyrazol-5-yl)isoindolin-1-one | 424.1 |
| 87 | 27 | 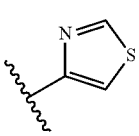 | 2-[(1S)-2-amino-1-(3-pyrimidin-5-ylbenzyl)ethyl]-5-(1-methyl-1H-pyrazol-5-yl)isoindolin-1-one | 425.1 |

<sup>1</sup>H NMR (400 MHz, CD<sub>3</sub>OD) of Example 80: δ 7.83 (d, J=8.0 Hz, 1H), 7.68 (s, 1H), 7.61 (dd, J=8.0, 1.2 Hz, 1H), 7.52 (d, J=2.0 Hz, 1H), 7.15 (dd, J=4.8, 2.0 Hz, 1H), 6.85 (d, J=4.8 Hz, 2H), 6.45 (d, J=2.0 Hz, 1H), 4.52 (m, 3H), 3.89 (s, 3H), 3.29 (m, 2H), 3.05 (m, 2H).

$^1$H NMR (300 MHz, DMSO-d$_6$) of Example 81 δ ppm: 7.66-7.72 (m, 2H), 7.58 (m, 1H), 7.48 (m, 1H), 7.38 (dd, J$^1$=2.9 Hz, J$^2$=4.9 Hz, 1H), 7.15 (m, 1H), 6.93 (m, 1H), 6.45 (t, J=1.9 Hz, 1H), 4.3-4.6 (m, 3H), 3.85 (s, 3H), 2.76-3.04 (m, 4H).

Example 88

2-[(1S)-2-amino-1-(3-ethynylbenzyl)ethyl]-5-(1-methyl-1H-pyrazol-5-yl)isoindolin-1-one

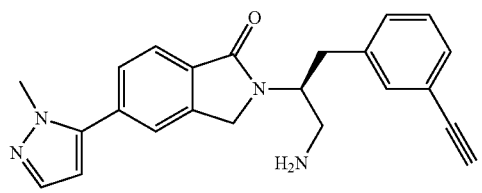 [SMILES: C#Cc1cccc(C[C@@H](CN)N2Cc3cc(-c4ccnn4C)ccc3C2=O)c1]

Step A: tert-butyl[(1S)-2-hydroxy-1-(3-iodobenzyl)ethyl]carbamate

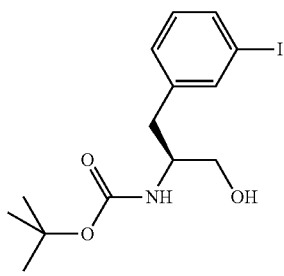 [SMILES: CC(C)(C)OC(=O)N[C@H](CO)Cc1cccc(I)c1]

To a solution of (2S)-2-[(tert-butoxycarbonyl)amino]-3-(3-iodophenyl)propanoic acid [Aldrich] (4.0 g, 10. mmol) in tetrahydrofuran (10 mL) with stirring was added 1.0 M borane-THF complex in THF (40 mL) dropwise to keep temperature at 0° C. (about 15 min). The reaction mixture was stirred at room temperature for 1 h, then cooled down with ice-bath, quenched with AcOH:MeOH (1:5, 20 mL) and partitioned between saturated aqueous NaHCO$_3$ solution and DCM, dried over sodium sulfate, filtered, and evaporated under reduced pressure. The residue was purified by combi-flash chromatography to give 2.0 g (52% yield) of the desired product. LC-MS found: 278.0 (M−Boc+H)$^+$.

Step B: tert-butyl ((1S)-2-hydroxy-1-{3-[(trimethylsilyl)ethynyl]benzyl}ethyl)carbamate

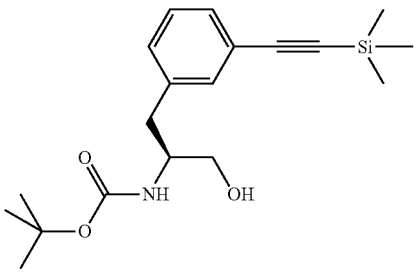 [SMILES: CC(C)(C)OC(=O)N[C@H](CO)Cc1cccc(C#C[Si](C)(C)C)c1]

tert-Butyl [(1S)-2-hydroxy-1-(3-iodobenzyl)ethyl]carbamate (1.0 g, 2.6 mmol), copper(I) iodide (0.020 g, 0.11 mmol), bis(triphenylphosphine)palladium(II) chloride (0.074 g, 0.11 mmol), tetrahydrofuran (7 mL), and triethylamine (0.41 mL, 2.9 mmol) were combined. The reaction mixture was stirred under N$_2$ for 5 min. (Trimethylsilyl)acetylene (1.1 mL, 8.0 mmol) was then added. The reaction mixture was stirred at 65° C. for 1 h, then evaporated under vacuum. The residue was purified by combi-flash chromatography to give 0.84 g (91% yield) of the desired product as light brown solid. LC-MS found: 248.0 (M−Boc+H)$^+$.

Step C: (2S)-2-amino-3-{3-[(trimethylsilyl)ethynyl]phenyl}propan-1-ol

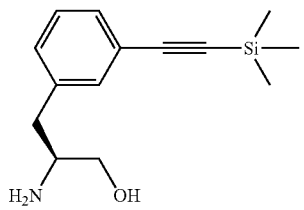 [SMILES: C[Si](C)(C)C#Cc1cccc(C[C@H](N)CO)c1]

tert-Butyl ((1S)-2-hydroxy-1-{3-[(trimethylsilyl)ethynyl]benzyl}ethyl)carbamate (0.84 g, 2.4 mmol), methanol (2.0 mL, 49 mmol), and 4.0 M hydrogen chloride in dioxane (5.0 mL, 20 mmol) were mixed together and stirred at room temperature for 1 h. The solvent was removed under vacuum to give 0.61 g (98% yield) of the desired product. LC-MS found: 248.0 (m+1).

Step D: 5-bromo-2-((1S)-2-hydroxy-1-{3-[(trimethylsilyl)ethynyl]benzyl}ethyl)isoindolin-1-one

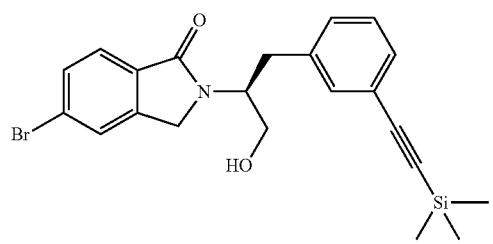 [SMILES: C[Si](C)(C)C#Cc1cccc(C[C@@H](CO)N2Cc3cc(Br)ccc3C2=O)c1]

A solution of methyl 4-bromo-2-(bromomethyl)benzoate (0.75 g, 2.4 mmol), (2S)-2-amino-3-{3-[(trimethylsilyl)ethynyl]phenyl}propan-1-ol (0.60 g, 2.4 mmol) and N,N-diisopropylethylamine (2.1 mL, 12 mmol) in 1-butanol (2 mL) in a sealed tube was stirred at 140° C. for 2 h. The solvent was removed under vacuum and the residue was eluted with 0-100% EtOAc in hexanes giving 0.78 g (73% yield) of the pure desired product as off white solid. LC/MS found: 442.0 $(M+H)^+$.

Step E: 2-((2S)-2-(5-bromo-1-oxo-1,3-dihydro-2H-isoindol-2-yl)-3-{3-[(trimethylsilyl)ethynyl]phenyl}propyl)-1H-isoindole-1,3(2H)-dione

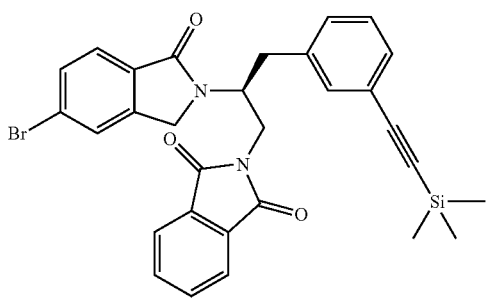 [SMILES: C[Si](C)(C)C#Cc1cccc(C[C@@H](CN2C(=O)c3ccccc3C2=O)N2Cc3cc(Br)ccc3C2=O)c1]

To a solution of diisopropyl azodicarboxylate (0.35 mL, 1.8 mmol) in tetrahydrofuran (2.9 mL) was added 5-bromo-2-((1S)-2-hydroxy-1-{3-[(trimethylsilyl)ethynyl]benzyl}ethyl)-isoindolin-1-one (0.58 g, 1.3 mmol), phthalimide (0.21 g, 1.4 mmol), and triphenylphosphine (0.35 g, 1.3 mmol). The mixture was stirred at room temperature for 4 h. Direct purification by combi-flash chromatography eluting with 0-60% EtOAc in hexanes afforded the desired product. LC-MS found: 571.1 $(M+H)^+$.

Step F: 2-[(1S)-2-amino-1-(3-ethynylbenzyl)ethyl]-5-(4-chloro-1-methyl-1H-pyrazol-5-yl)isoindolin-1-one A mixture of 1-methyl-5-(4,4,5,5-tetramethyl-1,3,2-dioxaborolan-2-yl)-1H-pyrazole (50.0 mg, 0.206 mmol), bis(tri-t-butylphosphine)palladium (20 mg, 0.04 mmol), 2-((2S)-2-(5-bromo-1-oxo-1,3-dihydro-2H-isoindol-2-yl)-3-{3-[(trimethylsilyl)ethynyl]phenyl}propyl)-1H-isoindole-1,3(2H)-dione (50.0 mg, 0.0875 mmol), and N,N-diisopropylethylamine (45 mg, 0.35 mmol) in 1,4-dioxane (1 mL) and water (60 μL) was microwaved at 130° C. for 30 minutes. The organic solvent was removed under vacuum to provide an oil residue. LC-MS found: 607.1 $(M+H)^+$.

To the residue was added methanol (0.5 mL) and hydrazine (0.3 mL). The resulting mixture was stirred at room temperature for 0.5 h. Direct purification on prep.—HPLC afforded the desired intermediate as white solid. LC-MS found: 477.1 $(M+H)^+$.

The white powder was then dissolved in 2 mL of MeOH, and stirred with solid $Na_2CO_3$ for 2 h. The mixture was filtered and rinsed with fresh MeOH. Direct purification on prep.—HPLC (pH=10) afforded the desired product. LC-MS found: 371.0 $(M+H)^+$; $^1H$ NMR (300 MHz, DMSO-$d_6$) δ ppm 7.62-7.71 (m, 2H), 7.58 (dd, $J^1$=1.35 Hz, $J^2$=7.84 Hz, 1H), 7.48 (d, J=1.9 Hz, 1H), 7.18-7.33 (m, 4H), 6.45 (d, J=1.9 Hz, 1H), 4.34-4.46 (m, 3H), 4.11 (s, 1H), 3.85 (s, 3H), 2.76-3.04 (m, 4H).

Example 89

2-[(1S)-2-amino-1-(3-ethynylbenzyl)ethyl]-5-(4-chloro-1-methyl-1H-pyrazol-5-yl)isoindolin-1-one

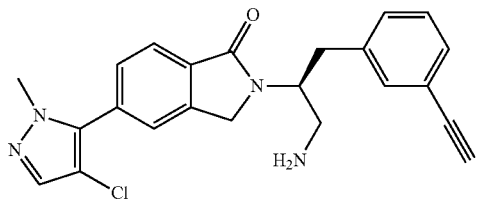 [SMILES: C#Cc1cccc(C[C@@H](CN)N2Cc3cc(-c4c(Cl)cnn4C)ccc3C2=O)c1]

The title compound was prepared as a white solid according to Example 88, except starting with 4-chloro-1-methyl-5-(4,4,5,5-tetramethyl-1,3,2-dioxaborolan-2-yl)-1H-pyrazole [prepared in Intermediate 1] instead of 1-methyl-5-(4,4,5,5-tetramethyl-1,3,2-dioxaborolan-2-yl)-1H-pyrazole. LC-MS found: 405 $(M+H)^+$.

Example 90

6-[(1S)-2-amino-1-(3-fluorobenzyl)ethyl]-3-(4-chloro-1-methyl-1H-pyrazol-5-yl)-5,6-dihydro-7H-pyrrolo[3,4-b]pyridin-7-one

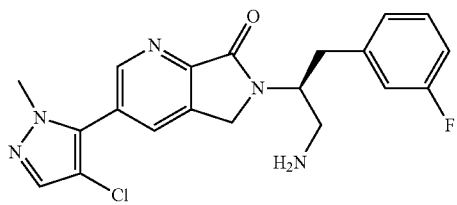 [SMILES: Cn1ncc(Cl)c1-c1cnc2c(c1)CN([C@H](CN)Cc1cccc(F)c1)C2=O]

Step A: 5-bromo-3-methylpyridine-2-carbonitrile

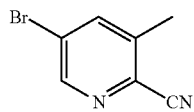

To a solution of 2,5-dibromo-3-methylpyridine (5.0 g, 20. mmol) in N,N-dimethylformamide (20.0 mL, 259 mmol) was added copper cyanide (1.8 g, 20. mmol) and the reaction was stirred at 120° C. for 12 h. The reaction was partitioned between EtOAc and water. The organic layer was washed with brine, dried over sodium sulfate, filtered, concentrated and purified by combi-flash chromatography to afford 1.94 g (49% yield) of the desired product as a white solid.

Step B: 5-bromo-3-methylpyridine-2-carboxylic acid

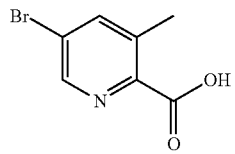

To a solution of 5-bromo-3-methylpyridine-2-carbonitrile (3.9 g, 20 mmol) in ethanol (30 mL) was added 6.0 M sodium hydroxide in water (15 mL), and the reaction was stirred at 80° C. for 1.5 h. The reaction mixture was concentrated, diluted with water and partitioned in EtOAc. The aqueous phase was acidified to pH 2-3. The product then was extracted with EtOAc, washed with brine, dried over sodium sulfate, filtered and concentrated to give 4.2 g (98% yield) of the desired product as a yellow solid.

Step C: methyl 5-bromo-3-methylpyridine-2-carboxylate

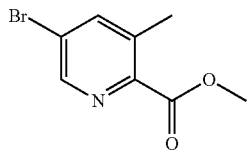

To a solution 5-bromo-3-methylpyridine-2-carboxylic acid (2.6 g, 12 mmol) in N,N-dimethylformamide (20.0 mL) was added potassium carbonate (4.99 g, 36.1 mmol) and methyl iodide (1.50 mL, 24.1 mmol) and the reaction was stirred 80° C. for 40 min. The reaction mixture was partitioned with EtOAc and water. The organic layers were washed with brine, dried over sodium sulfate, filtered and concentrated to afford 2.3 g (83% yield) of the desired product as a yellow solid.

Step D: methyl 5-bromo-3-(bromomethyl)pyridine-2-carboxylate

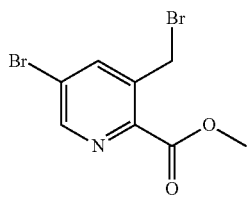

To a solution of methyl 5-bromo-3-methylpyridine-2-carboxylate (1.01 g, 4.39 mmol) in carbon tetrachloride (30.0 mL) was added N-bromosuccinimide (8.60E2 mg, 4.83 mmol) and 2,2'-azo-bis-isobutyronitrile (14.4 mg, 0.0877 mmol). The reaction mixture was stirred at 80° C. for 5 h. The reaction mixture was filtered and the filtrate was concentrated to afford 0.66 g (49% yield) of the desired product.

Step E: 2-[(2S)-2-(3-bromo-7-oxo-5,7-dihydro-6H-pyrrolo[3,4-b]pyridin-6-yl)-3-(3-fluorophenyl)propyl]-1H-isoindole-1,3(2H)-dione

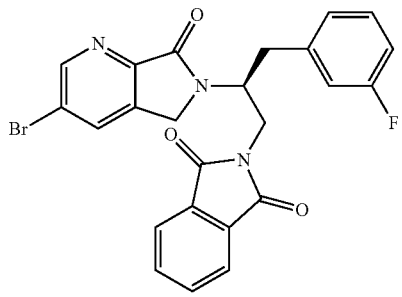 [SMILES: O=C1c2ccccc2C(=O)N1C[C@H](Cc1cccc(F)c1)N1Cc2cc(Br)cnc2C1=O]

A mixture of methyl 5-bromo-3-(bromomethyl)pyridine-2-carboxylate (500.0 mg, 1.618 mmol), 2-[(2S)-2-amino-3-(3-fluorophenyl)propyl]-1H-isoindole-1,3(2H)-dione (482.8 mg, 1.618 mmol) and N,N-diisopropylethylamine (0.564 mL, 3.24 mmol) in 1-butanol (10.0 mL) was stirred at 120° C. for 2 h under microwave. Purification by combi-flash chromatography gave 0.48 g (61% yield) of the desired product. LC-MS found: 494.1 (M+H)$^+$.

Step F: 2-[(2S)-2-[3-(4-chloro-1-methyl-1H-pyrazol-5-yl)-7-oxo-5,7-dihydro-6H-pyrrolo[3,4-b]pyridin-6-yl]-3-(3-fluorophenyl)propyl]-1H-isoindole-1,3(2H)-dione

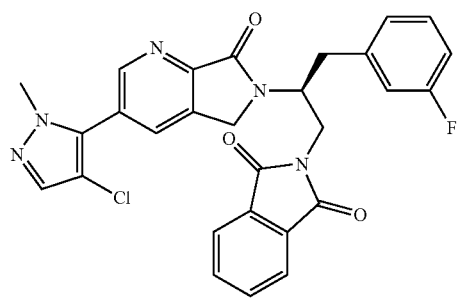 [SMILES: Cn1ncc(Cl)c1-c1cnc2c(c1)CN([C@@H](Cc1cccc(F)c1)CN1C(=O)c3ccccc3C1=O)C2=O]

A mixture of 4-chloro-1-methyl-5-(4,4,5,5-tetramethyl-1,3,2-dioxaborolan-2-yl)-1H-pyrazole (150 mg, 0.63 mmol), 2-[(2S)-2-(3-bromo-7-oxo-5,7-dihydro-6H-pyrrolo[3,4-b]pyridin-6-yl)-3-(3-fluorophenyl)propyl]-1H-isoindole-1,3 (2H)-dione (150 mg, 0.32 mmol), bis(tri-t-butylphosphine) palladium (30 mg, 0.06 mmol) and N,N-diisopropylethylamine (0.16 mL, 0.95 mmol) in 1,4-dioxane (5.0 mL, 64 mmol) and water (0.5 mL, 30 mmol) was stirred at 110° C. for 40 min at microwave. Direct purification on prep.—HPLC (pH=10) afforded 48 mg (29% yield) of the desired intermediate as white solid. LC-MS found: 530.1 (M+H)$^+$.

Step G: 6-[(1S)-2-amino-1-(3-fluorobenzyl)ethyl]-3-(4-chloro-1-methyl-1H-pyrazol-5-yl)-5,6-dihydro-7H-pyrrolo[3,4-b]pyridin-7-one 2-[(2S)-2-[3-(4-Chloro-1-methyl-1H-pyrazol-5-yl)-7-oxo-5,7-dihydro-6H-pyrrolo [3,4-b]pyridin-6-yl]-3-(3-fluorophenyl)propyl]-1H-isoindole-1,3(2H)-dione (48 mg, 0.91) was dissolved in methanol (2 mL), tetrahydrofuran (2 mL) and hydrazine (0.2 mL). The resulting reaction mixture was stirred at 50° C. for 2 h. Direct purification on prep.—HPLC (pH=10) afforded 12 mg (30.1% yield) of the desired intermediate as white solid. LC-MS found: 400.1 (M+H)$^+$; $^1$H NMR (300 MHz, DMSO-d$_6$) δ ppm: 8.78 (d, J=1.8 Hz, 1H), 8.32 (d, J=1.8 Hz, 1H), 7.74 (s, 1H), 7.26 (ddd, J$^1$=7.8 Hz, J$^2$=6.3 Hz, J$^3$=8.1 Hz, 1H), 7.06 (m, 2H), 6.96 (dd, J$^1$=8.7 Hz, J$^2$=8.4 Hz, 1H), 4.51 (s, 2H), 4.34 (m, 1H), 3.80 (s, 3H), 3.01 (m, 2H), 2.91 (m, 2H).

Example 91

6-[(1S)-2-amino-1-(3-fluorobenzyl)ethyl]-3-(4-bromo-1-methyl-1H-pyrazol-5-yl)-5,6-dihydro-7H-pyrrolo[3,4-b]pyridin-7-one

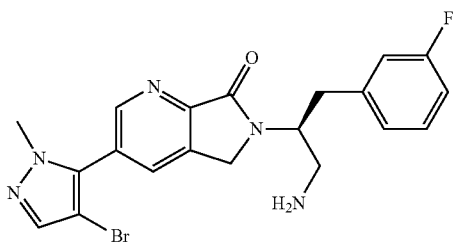 [SMILES: Cn1ncc(Br)c1-c1cnc2c(c1)CN([C@H](CN)Cc1cccc(F)c1)C2=O]

A mixture of 1-methyl-5-(4,4,5,5-tetramethyl-1,3,2-dioxaborolan-2-yl)-1H-pyrazole (42 mg, 0.202 mmol), 2-[(2S)-2-(3-bromo-7-oxo-5,7-dihydro-6H-pyrrolo[3,4-b]pyridin-6-yl)-3-(3-fluorophenyl)propyl]-1H-isoindole-1,3(2H)-dione [prepared in Example 90] (100 mg, 0.202 mmol), bis(tri-t-butylphosphine)-palladium (10 mg, 0.02 mmol) and N,N-diisopropylethylamine (0.16 mL, 0.95 mmol) in 1,4-dioxane (4.0 mL) and water (0.2 mL) was stirred at 110° C. for 30 min under microwave. Direct purification on prep.—HPLC (pH=10) afforded 35 mg (35% yield) of the desired intermediate, 2-{3-(3-fluorophenyl)-2-[3-(1-methyl-1H-pyrazol-5-yl)-7-oxo-5,7-dihydro-6H-pyrrolo[3,4-b]pyridin-6-yl]propyl}-1H-isoindole-1, 3(2H)-dione, as white solid. LC-MS found: 495.9 (M+H)$^+$.

To a solution of the above intermediate (35 mg, 0.07 mmol) in tetrahydrofuran (2 mL) was added N-bromosuccinimide (13 mg, 0.07 mmol). The mixture was stirred at room temperature overnight. Direct purification on prep.—HPLC afforded 20 mg (50% yield) of the desired white powder compound. LC-MS found: 574.1 (M+H)$^+$; LC-MS found: 574.1 (M+H)$^+$; $^1$H NMR (300 MHz, DMSO-d$_6$) δ ppm: 8.66 (d, J=1.8 Hz, 1H), 8.23 (d, J=1.8 Hz, 1H), 7.73 (s, 4H), 7.68 (d, J=4.2 Hz, 1H), 7.25 (dd, J$^1$=7.8 Hz, J$^2$=6.6 Hz, 1H), 7.07 (m, 2H), 6.94 (ddd, J$^1$=8.4 Hz, J$^2$=8.6 Hz, J$^3$=2.7 Hz, 1H), 4.90 (m, 1H), 4.70 (d, J=18 Hz, 1H), 4.47 (d, J=18 Hz, 1H), 4.00 (dd, J$^1$=10.2 Hz, J$^2$=9.9 Hz, 1H), 3.76 (s, 3H), 3.74 (m, 1H), 3.15 (m, 2H).

This white powder compound was then treated with hydrazine (0.2 mL) in MeOH (2 mL) and THF (2 mL) at 50° C. for 2 h to give 6.3 mg (41% yield) of the final product. LC-MS found: 443.9 (M+H)$^+$; $^1$H NMR (300 MHz, DMSO-d$_6$) δ ppm: 8.77 (d, J=1.8 Hz, 1H), 8.21 (d, J=1.8 Hz, 1H), 7.74 (s, 1H), 7.26 (m, 1H), 7.06 (dd, J$^1$=9.3 Hz, J$^2$=6.3 Hz, 2H), 6.97 (m, 1H), 4.51 (s, 2H), 4.50 (m, 1H), 3.80 (s, 3H), 3.00 (m, 2H), 2.90 (m, 2H).

Example 92

2-[(1S)-2-amino-1-(3-fluorobenzyl)ethyl]-6-(4-chloro-1-methyl-1H-pyrazol-5-yl)-1,2-dihydro-3H-pyrrolo[3,4-c]pyridin-3-one

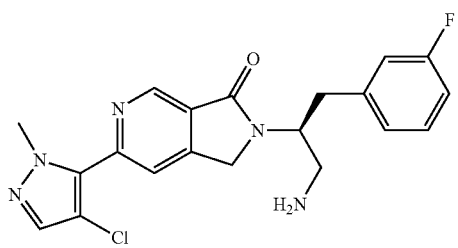 [SMILES: Cn1ncc(Cl)c1-c1cc2c(cn1)C(=O)N([C@H](CN)Cc1cccc(F)c1)C2]

Step A: methyl 4-(bromomethyl)-6-chloronicotinate

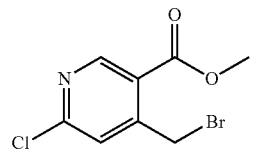

A mixture of methyl 6-chloro-4-methylnicotinate (2.50 g, 13.5 mmol), N-bromosuccinimide (2.88 g, 16.2 mmol) and benzoyl peroxide (0.14 g, 0.56 mmol) in carbon tetrachloride (100 mL) was refluxed under an atmosphere of nitrogen overnight. The mixture was cooled to room temperature, and filtered through a pad of celite. The mixture was concentrated. The residue was purified by combi-flash chromatography (ethyl acetate in hexanes: 30%) to afford the desired product.

Step B: 2-[(2S)-2-(6-chloro-3-oxo-1,3-dihydro-2H-pyrrolo[3,4-c]pyridin-2-yl)-3-(3-fluorophenyl)propyl]-1H-isoindole-1,3(2H)-dione

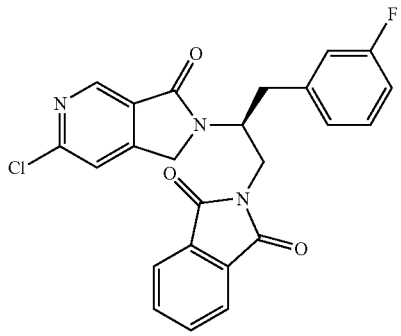 [SMILES: O=C1c2ccccc2C(=O)N1C[C@H](Cc1cccc(F)c1)N1Cc2cc(Cl)ncc2C1=O]

A solution methyl 4-(bromomethyl)-6-chloronicotinate (0.200 g, 0.756 mmol), 2-[(2S)-2-amino-3-(3-fluorophenyl)propyl]-1H-isoindole-1,3(2H)-dione [1.0]-Hydrogen chloride (0.230 g, 0.687 mmol) and N,N-diisopropylethylamine (0.359 mL, 2.06 mmol) in 1-butanol (2 mL) was stirred at 140° C. for 2 h. The mixture was concentrated, and water (30 ml) was added to the residue and extracted with EtOAc (2×30 mL). The combined organic phases were washed with water, brine and dried over $Na_2SO_4$. After concentration, the residue was purified by combi-flash chromatography eluted with EtOAc/hexane (10-60%). The purification gave 0.204 g (66% yield) of the desired product as off white solid. LC/MS found: 450.0 $(M+H)^+$.

Step C: 2-[(1S)-2-amino-1-(3-fluorobenzyl)ethyl]-6-(4-chloro-1-methyl-1H-pyrazol-5-yl)-1,2-dihydro-3H-pyrrolo[3,4-c]pyridin-3-one A mixture of 1-methyl-4-chloro-5-(4,4,5,5-tetramethyl-1,3,2-dioxaborolan-2-yl)-1H-pyrazole (19.4 mg, 0.0800 mmol), bis(tri-t-butylphosphine)palladium (3.4 mg, 0.0067 mmol), 2-[(2S)-2-(6-chloro-3-oxo-1,3-dihydro-2H-pyrrolo[3,4-c]pyridin-2-yl)-3-(3-fluorophenyl)propyl]-1H-isoindole-1,3(2H)-dione (30.0 mg, 0.0667 mmol) and N,N-diisopropylethylamine (34.8 µL, 0.200 mmol) in 1,4-dioxane (1 mL) and water (50 µL) was microwaved at 110° C. for 15 minutes. Filtered through a pad of celite and concentrated, the residue was purified by combi-flash chromatography eluted with EtOAc/hexane (50-100%). To the purified intermediate was added methanol (0.4 mL), tetrahydrofuran (0.4 mL) and hydrazine (0.2 mL, 6 mmol). The solution was stirred at room temperature overnight. Purification by prep.—HPLC (pH=10) gave the desired product as white solid. LC-MS found: 400.1 $(M+H)^+$; $^1$H NMR (300 MHz, DMSO-$d_6$) δ ppm: 8.95 (s, 1H), 7.97 (s, 1H), 7.72 (s, 1H), 7.23 (m, 1H), 6.98 (m, 2H), 6.95 (dt, $J^1$=9.30 Hz, $J^2$=1.80 Hz, 1H), 4.59 (s, 2H), 4.41 (m, 1H), 3.93 (s, 3H), 3.02 (dd, $J^1$=14.40 Hz, $J^2$=5.10 Hz, 1H), 2.89 (m, 1H), 2.81 (d, J=6.60 Hz, 2H).

The following compounds listed in Table 5 were prepared by a method analogous to that for Example 92.

TABLE 5

| Ex. # | R¹ | Compound | LC-MS (M + H)⁺ |
|---|---|---|---|
| 93 | H | 2-[(1S)-2-amino-1-(3-fluorobenzyl)ethyl]-6-(1-methyl-1H-pyrazol-5-yl)-1,2-dihydro-3H-pyrrolo[3,4-c]pyridin-3-one | 366.1 |
| 94 | Me | 2-[(1S)-2-amino-1-(3-fluorobenzyl)ethyl]-6-(4-methyl-1-methyl-1H-pyrazol-5-yl)-1,2-dihydro-3H-pyrrolo[3,4-c]pyridin-3-one | 379.9 |
| 95 | CH₂OPr$^i$ | 2-[(1S)-2-amino-1-(3-fluorobenzyl)ethyl]-6-[4-(2-propoxymethyl)-1-methyl-1H-pyrazol-5-yl]-1,2-dihydro-3H-pyrrolo[3,4-c]pyridin-3-one | 438.1 |
| 96 | CH₂OPr$^n$ | 2-[(1S)-2-amino-1-(3-fluorobenzyl)ethyl]-6-[4-(1-propoxymethyl)-1-methyl-1H-pyrazol-5-yl]-1,2-dihydro-3H-pyrrolo[3,4-c]pyridin-3-one | 438.1 |
| 97 | CH₂-O-cyclobutyl | 2-[(1S)-2-amino-1-(3-fluorobenzyl)ethyl]-6-[4-(cyclobutoxymethyl)-1-methyl-1H-pyrazol-5-yl]-1,2-dihydro-3H-pyrrolo[3,4-c]pyridin-3-one | 450.1 |
| 98 | CH₂-S-Et | 2-[(1S)-2-amino-1-(3-fluorobenzyl)ethyl]-6-[4-(ethylthiomethyl)-1-methyl-1H-pyrazol-5-yl]-1,2-dihydro-3H-pyrrolo[3,4-c]pyridin-3-one | 440.1 |
| 99 | CH₂-S-Me | 2-[(1S)-2-amino-1-(3-fluorobenzyl)ethyl]-6-[4-(methylthiomethyl)-1-methyl-1H-pyrazol-5-yl]-1,2-dihydro-3H-pyrrolo[3,4-c]pyridin-3-one | 426.1 |

$^1$H NMR (300 MHz, DMSO-$d_6$) of Example 93 δ ppm: 8.85 (s, 1H), 8.00 (s, 1H), 7.51 (d, J=2.10 Hz, 1H), 7.22 (m, 1H), 6.96 (m, 3H), 6.86 (d, J=1.80 Hz, 1H), 4.53 (s, 2H), 4.39 (m, 1H), 4.13 (s, 3H), 3.02 (m, 1H), 2.90 (m, 1H), 2.81 (d, J=6.90 Hz, 2H).

$^1$H NMR (300 MHz, DMSO-$d_6$) of Example 94 δ ppm: 8.91 (s, 1H), 7.79 (s, 1H), 7.36 (s, 1H), 7.24 (m, 1H), 7.06 (m, 2H), 6.95 (m, 1H), 4.56 (s, 2H), 4.40 (m, 1H), 3.88 (s, 3H), 3.02 (m, 1H), 2.89 (m, 1H), 2.81 (d, J=6.90 Hz, 2H), 2.09 (s, 3H).

$^1$H NMR (300 MHz, DMSO-$d_6$) of Example 96 δ ppm: 8.93 (s, 1H), 7.91 (s, 1H), 7.55 (s, 1H), 7.23 (m, 1H), 7.01 (m, 3H), 4.59 (s, 2H), 4.43 (m, 1H), 4.32 (s, 2H), 3.95 (s, 3H), 3.34 (t, J=6.5 Hz, 2H), 2.90 (m, 4H), 1.49 (m, 2H), 0.81 (m, 3H).

$^1$H NMR (300 MHz, DMSO-$d_6$) of Example 97 δ ppm: 8.93 (s, 1H), 7.92 (s, 1H), 7.55 (s, 1H), 7.24 (m, 1H), 7.02 (m, 3H), 4.59 (s, 2H), 4.43 (m, 1H), 4.24 (s, 2H), 3.93 (m, 4H), 2.92 (m, 4H), 2.07 (m, 2H), 1.67 (m, 4H).

Example 100

Preparation of 2-((1S)-2-amino-1-benzylethyl)-6-(4-chloro-1-methyl-1H-pyrazol-5-yl)-1,2-dihydro-3H-pyrrolo[3,4-c]pyridin-3-one

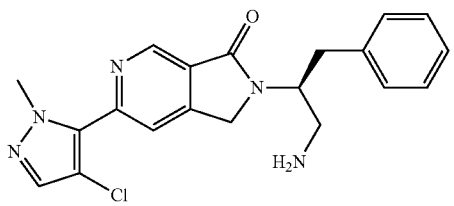 [SMILES: Cn1ncc(Cl)c1-c1cc2c(cn1)C(=O)N([C@H](CN)Cc1ccccc1)C2]

The title compound was prepared by a method analogous to that for Example 92. LC-MS found: 382.0 (M+H)⁺; ¹H NMR (300 MHz, DMSO-$d_6$) δ ppm: 8.91 (d, J=0.6 Hz, 1H), 7.92 (d, J=0.4 Hz, 1H), 7.67 (s, 1H), 7.08 (m, 5H), 4.52 (d, J=3.0 Hz, 2H), 4.36 (m, 1H), 3.88 (s, 3H), 2.95 (m, 1H), 2.83 (m, 1H), 2.77 (d, J=6.6 Hz, 2H).

Example 101

2-[(1S)-2-amino-1-(3,5-difluorobenzyl)ethyl]-6-(4-chloro-1-methyl-1H-pyrazol-5-yl)-1,2-dihydro-3H-pyrrolo[3,4-c]pyridin-3-one

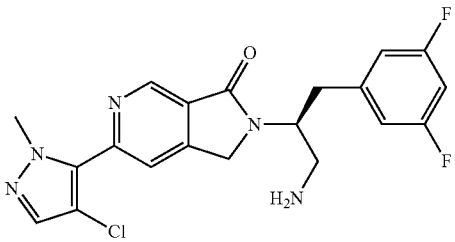 [SMILES: Cn1ncc(Cl)c1-c1cc2c(cn1)C(=O)N([C@H](CN)Cc1cc(F)cc(F)c1)C2]

Step A: 6-chloro-2-[(1S)-1-(3,5-difluorobenzyl)-2-hydroxyethyl]-1,2-dihydro-3H-pyrrolo[3,4-c]pyridin-3-one

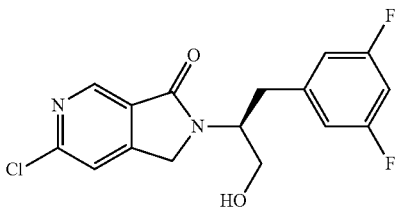 [SMILES: O=C1c2cnc(Cl)cc2CN1[C@H](CO)Cc1cc(F)cc(F)c1]

A solution of methyl 4-(bromomethyl)-6-chloronicotinate (0.400 g, 1.51 mmol), (2S)-2-amino-3-(3,5-difluorophenyl)propan-1-ol [1.0]-sodium (0.319 g, 1.52 mmol) and N,N-diisopropylethylamine (0.790 mL, 4.54 mmol) in 1-butanol (1 mL) was stirred at 140° C. for 2 h. After concentration, to the residue was added water (30 mL), which was extracted with EtOAc (2×). The combined organic phases were washed with water, brine and dried over $Na_2SO_4$. After concentration, the residue was purified by combi-flash chromatography eluted with EtOAc/hexane (50-100%). The purification gave 0.352 g (68.7% yield) of the desired product as off white solid. LC/MS found: 339.0 (M+H)⁺.

Step B: 2-[(2S)-2-(6-chloro-3-oxo-1,3-dihydro-2H-pyrrolo[3,4-c]pyridin-2-yl)-3-(3,5-difluorophenyl)propyl]-1H-isoindole-1,3(2H)-dione

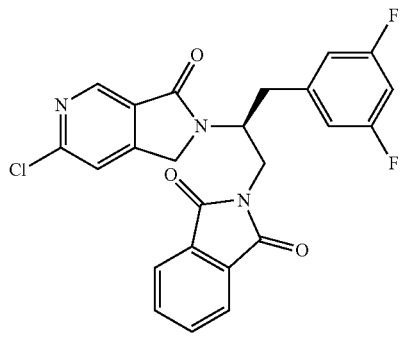 [SMILES: O=C1c2ccccc2C(=O)N1C[C@H](Cc1cc(F)cc(F)c1)N1Cc2cc(Cl)ncc2C1=O]

To a solution of 6-chloro-2-[(1S)-1-(3,5-difluorobenzyl)-2-hydroxyethyl]-1,2-dihydro-3H-pyrrolo[3,4-c]pyridin-3-one (0.340 g, 1.00 mmol), triphenylphosphine (0.263 g, 1.00 mmol) and phthalimide (0.148 g, 1.00 mmol) in tetrahydrofuran (10 mL) at 25° C. was added diethyl azodicarboxylate (0.514 mL, 1.30 mmol). The reaction was stirred at room temperature overnight. After concentration, the residue was purified by combi-flash chromatography eluting with EtOAc/hexane (10-60%). The purification gave 0.360 g (76.7% yield) of the desired product as light green solid. LC/MS found: 468.0 (M+1)⁺.

Step C: 2-[(1S)-2-amino-1-(3,5-difluorobenzyl)ethyl]-6-(4-chloro-1-methyl-1H-pyrazol-5-yl)-1,2-dihydro-3H-pyrrolo[3,4-c]pyridin-3-one The title compound was prepared according to a procedure similar to that for Example 92, Step C. LC-MS found: 418.2 (M+H)⁺; ¹H NMR (400 MHz, DMSO-$d_6$) δ ppm: 8.91 (d, J=0.80 Hz, 1H), 7.93 (s, 1H), 7.67 (s, 1H), 6.92 (m, 3H), 4.57 (dd, J¹=24.80 Hz, J²=19.20 Hz, 2H), 4.38 (m, 1H), 3.89 (s, 3H), 2.98 (m, 1H), 2.83 (m, 1H), 2.76 (m, 2H).

The following compounds listed in Table 6 were prepared according to a method analogous to that for Example 101.

TABLE 6

| Ex. # | R¹ | Compound | LC-MS (M+H)⁺ |
|---|---|---|---|
| 102 | H | 2-[(1S)-2-amino-1-(3,5-difluorobenzyl)ethyl]-6-(1-methyl-1H-pyrazol-5-yl)-1,2-dihydro-3H-pyrrolo[3,4-c]pyridin-3-one | 384.1 |

TABLE 6-continued

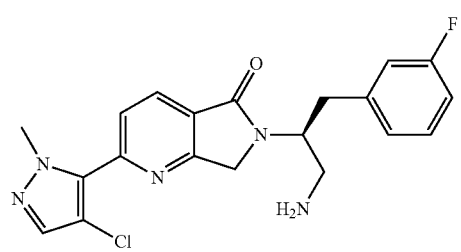 [SMILES: Cn1ncc(Cl)c1-c1ccc2c(n1)CN([C@H](CN)Cc1cccc(F)c1)C2=O]

| Ex. # | R¹ | Compound | LC-MS (M + H)⁺ |
|---|---|---|---|
| 103 | Me | 2-[(1S)-2-amino-1-(3,5-difluoro-benzyl)ethyl]-6-(4-methyl-1-methyl-1H-pyrazol-5-yl)-1,2-dihydro-3H-pyrrolo[3,4-c]pyridin-3-one | 398.1 |
| 104 | Br | 2-[(1S)-2-amino-1-(3,5-difluoro-benzyl)ethyl]-6-(4-broro-1-methyl-1H-pyrazol-5-yl)-1,2-dihydro-3H-pyrrolo[3,4-c]pyridin-3-one | 462.1 |
| 105 | CH₂OCH₃ | 2-[(1S)-2-amino-1-(3,5-difluoro-benzyl)ethyl]-6-(4-methoxymethyl-1-methyl-1H-pyrazol-5-yl)-1,2-dihydro-3H-pyrrolo[3,4-c]pyridin-3-one | 428.1 |
| 106 | CH₂OPrⁱ | 2-[(1S)-2-amino-1-(3,5-difluoro-benzyl)ethyl]-6-[4-(2-propoxy-methyl)-1-methyl-1H-pyrazol-5-yl]-1,2-dihydro-3H-pyrrolo[3,4-c]pyridin-3-one | 456.1 |
| 107 | CH₂OPrⁿ | 2-[(1S)-2-amino-1-(3,5-difluoro-benzyl)ethyl]-6-[4-(1-propoxy-methyl)-1-methyl-1H-pyrazol-5-yl]-1,2-dihydro-3H-pyrrolo[3,4-c]pyridin-3-one | 456.1 |
| 108 | 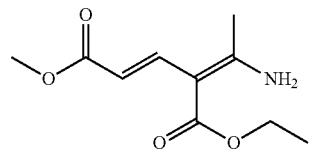 | 2-[(1S)-2-amino-1-(3,5-difluoro-benzyl)ethyl]-6-[4-(cyclobutoxy-methyl)-1-methyl-1H-pyrazol-5-yl]-1,2-dihydro-3H-pyrrolo[3,4-c]pyridin-3-one | 468.1 |

¹H NMR (400 MHz, DMSO-d₆) of Example 102 δ ppm: 8.81 (s, 1H), 7.97 (s, 1H), 7.47 (d, J=2.00 Hz, 1H), 6.90 (m, 3H), 6.82 (d, J=2.00 Hz, 1H), 4.51 (d, J=7.20 Hz, 2H), 4.35 (m, 1H), 4.08 (s, 3H), 2.98 (m, 1H), 2.83 (m, 1H), 2.76 (d, J=6.80 Hz, 2H).

¹H NMR (400 MHz, DMSO-d₆) of Example 103 δ ppm: 8.92 (d, J=0.80 Hz, 1H), 7.80 (s, 1H), 7.37 (s, 1H), 6.98 (m, 3H), 4.58 (d, J=2.40 Hz, 2H), 4.44 (m, 1H), 3.88 (s, 3H), 3.02 (m, 1H), 2.90 (m, 1H), 2.84 (d, J=6.80 Hz, 2H), 2.10 (s, 3H).

¹H NMR (400 MHz, DMSO-d₆) of Example 105 δ ppm: 8.94 (s, 1H), 7.89 (s, 1H), 7.57 (s, 1H), 6.99 (m, 3H), 4.63 (m, 3H), 4.29 (s, 2H), 3.95 (s, 3H), 3.23 (s, 3H), 2.92 (m, 4H).

¹H NMR (400 MHz, DMSO-d₆) of Example 106 δ ppm: 8.93 (s, 1H), 7.95 (s, 1H), 7.54 (s, 1H), 6.96 (m, 3H), 4.61 (m, 3H), 4.32 (s, 2H), 3.95 (s, 3H), 3.61 (m, 1H), 2.82 (m, 4H), 1.08 (d, J=6.1 Hz, 6H).

¹H NMR (400 MHz, DMSO-d₆) of Example 107 δ ppm: 7.70 (m, 2H), 7.55 (m, 1H), 6.97 (m, 3H), 4.46 (m, 3H), 4.16 (s, 2H), 3.76 (s, 3H), 3.38 (t, J=6.0 Hz, 2H), 2.91 (m, 4H), 1.45 (m, 2H), 0.79 (t, J=9.0 Hz, 3H).

¹H NMR (400 MHz, DMSO-d₆) of Example 108 δ ppm: 8.94 (s, 1H), 7.93 (s, 1H), 7.55 (s, 1H), 6.95 (m, 3H), 4.57 (m, 3H), 4.24 (s, 2H), 3.94 (m, 4H), 2.96 (m, 4H), 2.06 (m, 2H), 1.63 (m, 4H).

Example 109

6-[(1S)-2-amino-1-(3-fluorobenzyl)ethyl]-2-(4-chloro-1-methyl-1H-pyrazol-5-yl)-6,7-dihydro-5H-pyrrolo[3,4-b]pyridin-5-one

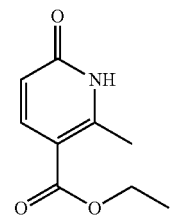

Step A: 5-ethyl 1-methyl (2E,4Z)-4-(1-aminoeth-ylidene)pent-2-enedioate

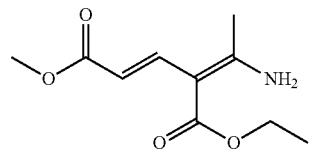

Ethyl (2Z)-3-aminobut-2-enoate (6.46 g, 50.0 mmol) and methyl propiolate (4.20 g, 50.0 mmol) were mixed in one 100 mL flask, and the mixture was stirred at 110° C. for 10 hrs. The reaction mixture was cooled to room temperature and recrystallized with methanol to give 10 g (93% yield) of the pure product. LC-MS found: 214.2.1 (M+H)⁺.

Step B: ethyl 2-methyl-6-oxo-1,6-dihydropyridine-3-carboxylate

5-Ethyl 1-methyl (2E,4Z)-4-(1-aminoethylidene)pent-2-enedioate (10 g, 50 mmol) and DMF (30 mL) were mixed in one 100 mL flask, and the mixture was stirred at 165° C. for 14 hrs. The reaction mixture was cooled to room temperature, then filtered to give the crude product, which was washed with DMF and small amount of methanol to give 5 g (60% yield) of the pure product. LC-MS found: 182.1 (M+H)⁺.

Step C: ethyl 6-bromo-2-methylnicotinate

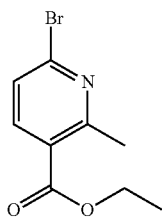

Ethyl 2-methyl-6-oxo-1,6-dihydropyridine-3-carboxylate (2.0 g, 11 mmol) and POBr₃ (8.9 g, 31 mmol) were mixed in one 100 mL flask, and the mixture was stirred at 130° C. for 4 hrs. The reaction mixture was cooled to room temperature and 50 g of ice water was added. The mixture was neutralized to pH=9 with aqueous NaHCO₃ solution, extracted twice with EtOAc, dried over sodium sulfate, filtered and concentrated under reduced pressure to give 2.5 g (93% yield) of the desired product. LC-MS found: 244.1 (M+H)⁺.

Step D: ethyl 6-bromo-2-(bromomethyl)nicotinate

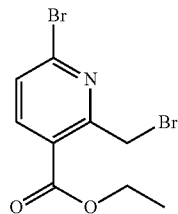

N-Bromosuccinimide (1.3 g, 7.3 mmol), carbon tetrachloride (30 mL) and 2,2'-azo-bis-isobutyronitrile (0.30 g, 1.8 mmol) were mixed in one 100 mL flask. The mixture was stirred at 90° C. overnight, cooled to room temperature, concentrated under reduced pressure, purified with combi-flash chromatography using hexane/EtOAc system to give 0.8 g (40% yield) of the solid product. LC-MS found: 323.7 (M+H)₊.

Step E: 2-bromo-6-[(1S)-1-(3-fluorobenzyl)-2-hydroxyethyl]-6,7-dihydro-5H-pyrrolo[3,4-b]pyridin-5-one

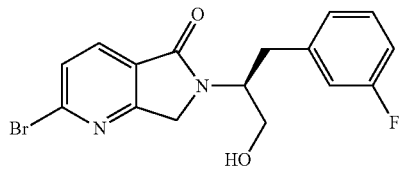

Ethyl 6-bromo-2-(bromomethyl)nicotinate (0.17 g, 0.53 mmol), (2S)-2-amino-3-(3-fluorophenyl)propan-1-ol (0.11 g, 0.64 mmol), N,N-diisopropylethylamine (0.2 g, 2 mmol) and 1,4-dioxane (5 mL) were mixed in one 20 mL microwave tube, and the mixture was stirred at 67° C. for overnight. LC-MS showed most starting material was converted to Br-replacement product. Then the temperature was raised to 125° C. for 45 mins, cooled to room temperature, then worked up with EtOAc and aqueous NaHCO₃ solution, extracted twice with EtOAc and dried over sodium sulfate, and concentrated under reduced pressure. Purification by combi-flash chromatography gave the desired product. LC-MS found: 365.1 (M+H)⁺.

Step F: 2-(4-chloro-1-methyl-1H-pyrazol-5-yl)-6-[(1S)-1-(3-fluorobenzyl)-2-hydroxyethyl]-6,7-dihydro-5H-pyrrolo[3,4-b]pyridin-5-one

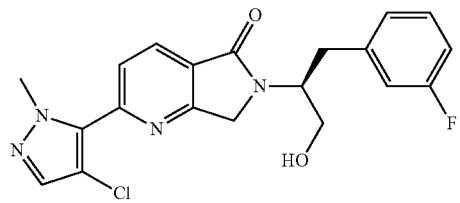 [SMILES: Cn1ncc(Cl)c1-c1ccc2c(n1)CN([C@H](CO)Cc1cccc(F)c1)C2=O]

In one 20 mL vial, a mixture of 2-bromo-6-[(1S)-1-(3-fluorobenzyl)-2-hydroxyethyl]-6,7-dihydro-5H-pyrrolo[3,4-b]pyridin-5-one (0.041 g, 0.11 mmol), 4-chloro-1-methyl-5-(4,4,5,5-tetramethyl-1,3,2-dioxaborolan-2-yl)-1H-pyrazole (0.0327 g, 0.135 mmol), bis(tri-t-butylphosphine) palladium (0.00574 g, 0.0112 mmol), and N,N-diisopropylethylamine (0.0587 mL, 0.337 mmol) in 1,4-dioxane (5 mL) was microwaved at 120° C. for 20 minutes. The resulting mixture was filtered through a pad of celite and concentrated, and the residue was purified by combi-flash chromatography using hexane/EtOAc/methanol to give 31 mg (68% yield) of the final product. LC/MS found: 401.1 (M+H)⁺.

Step G: 2-[(2S)-2-[2-(4-chloro-1-methyl-1H-pyrazol-5-yl)-5-oxo-5,7-dihydro-6H-pyrrolo[3,4-b]pyridin-6-yl]-3-(3-fluorophenyl)propyl]-1H-isoindole-1,3(2H)-dione

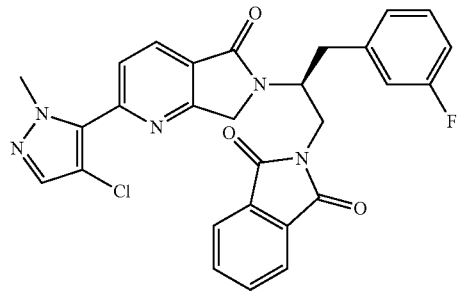 [SMILES: Cn1ncc(Cl)c1-c1ccc2c(n1)CN([C@@H](Cc1cccc(F)c1)CN1C(=O)c3ccccc3C1=O)C2=O]

To a solution of 2-(4-chloro-1-methyl-1H-pyrazol-5-yl)-6-[(1S)-1-(3-fluorobenzyl)-2-hydroxyethyl]-6,7-dihydro-5H-pyrrolo[3,4-b]pyridin-5-one (0.065 g, 0.16 mmol) and phthalimide (0.029 g, 0.19 mmol) in tetrahydrofuran (5 mL) at 25° C. was added diethyl azodicarboxylate (0.096 mL, 0.24 mmol) and triphenylphosphine (0.055 g, 0.21 mmol). The reaction mixture was stirred at room temperature for 2 hr. After concentration, the residue was purified by pH=2

Prep.—HPLC to give 0.020 g (23% yield) of the desired product as white powder. LC/MS found: 530.1 (M+H)+.

Step H: 6-[(1S)-2-amino-1-(3-fluorobenzyl)ethyl]-2-(4-chloro-1-methyl-1H-pyrazol-5-yl)-6,7-dihydro-5H-pyrrolo[3,4-b]pyridin-5-one 2-[(2S)-2-[2-(4-Chloro-1-methyl-1H-pyrazol-5-yl)-5-oxo-5,7-dihydro-6H-pyrrolo[3,4-b]pyridin-6-yl]-3-(3-fluorophenyl)propyl]-1H-isoindole-1,3(2H)-dione (0.050 g, 0.094 mmol) was dissolved in methanol (2 mL), and hydrazine (0.06 g, 2 mmol) was added. The reaction was stirred at 60° C. for 2 hr. After concentration, the residue was purified by pH=10 Prep.—HPLC to give the desired product as white powder. LC-MS found: 400.1 (M+H)+.

Example 110

6-[(1S)-2-amino-1-(3-fluorobenzyl)ethyl]-2-(1-methyl-1H-pyrazol-5-yl)-6,7-dihydro-5H-pyrrolo[3,4-b]pyridin-5-one

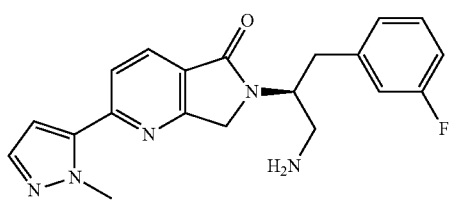 [SMILES: Cn1nccc1-c1ccc2c(n1)CN([C@H](CN)Cc1cccc(F)c1)C2=O]

The title compound was prepared as a white solid according to a method analogous to that for Example 109, except starting with 1-methyl-5-(4,4,5,5-tetramethyl-1,3,2-dioxaborolan-2-yl)-1H-pyrazole instead of 4-chloro-1-methyl-5-(4,4,5,5-tetramethyl-1,3,2-dioxaborolan-2-yl)-1H-pyrazole [prepared in Intermediate 1].

Example 111

6-[(1S)-2-amino-1-benzylethyl]-2-(1-methyl-1H-pyrazol-5-yl)-6,7-dihydro-5H-pyrrolo[3,4-b]pyridin-5-one

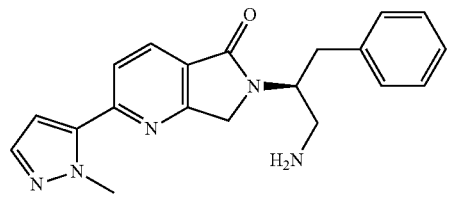 [SMILES: Cn1nccc1-c1ccc2c(n1)CN([C@H](CN)Cc1ccccc1)C2=O]

tert-Butyl-[(2S)-2-amino-3-phenylpropyl]carbamate (0.16 g, 0.64 mmol), ethyl 6-bromo-2-(bromomethyl)nicotinate (0.17 g, 0.53 mmol), dioxane (4 mL) and diisopropylethylamine (0.2 g, 2 mmol) were mixed in one 20 mL microwave tube, and the mixture was stirred at 67° C. overnight. LC/MS showed most of the starting material was converted to Br-replacement product. Then the temperature was raised to 125° C. for 45 mins, then cooled down to room temperature. The mixture was worked up with EtOAc and aqueous NaHCO3 solution, extracted twice with EtOAc, dried over sodium sulfate, and concentrated to give the crude residue. LC-MS found: 345.95 (M−100)+.

In one 20 mL vial, the mixture of the above residue, 1-methyl-5-(4,4,5,5-tetramethyl-1,3, 2-dioxaborolan-2-yl)-1H-pyrazole (0.0280 g, 0.135 mmol), bis(tri-t-butylphosphine) palladium (0.00574 g, 0.0112 mmol), and N,N-diisopropylethylamine (0.0587 mL, 0.337 mmol) in 1,4-dioxane (5 mL) was microwaved at 120° C. for 20 minutes. The mixture was filtered through a pad of celite and concentrated, the residue was purified by pH=2 prep.—HPLC to give the desired Suzuki coupling product. LC-MS found: 448.1 (M+H)+.

The Suzuki coupling product was dissolved in 50% TFA in DCM (2 mL) and then stirred at room temperature for 1 h. Direct purification on prep.—HPLC (pH=10) afforded the desired product as white solid. LC/MS found: 348.1 (M+H)+.

Example 112

6-[(1S)-2-amino-1-benzylethyl]-2-(4-chloro-1-methyl-1H-pyrazol-5-yl)-6,7-dihydro-5H-pyrrolo[3,4-b]pyridin-5-one

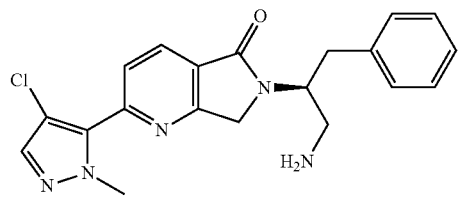 [SMILES: Cn1ncc(Cl)c1-c1ccc2c(n1)CN([C@H](CN)Cc1ccccc1)C2=O]

The title compound was prepared as a white solid according to a method analogous to that for Example 111, except starting with 1-methyl-5-(4,4,5,5-tetramethyl-1,3,2-dioxaborolan-2-yl)-1H-pyrazole instead of 4-chloro-1-methyl-5-(4,4,5,5-tetramethyl-1,3,2-dioxaborolan-2-yl)-1H-pyrazole [prepared in Intermediate 1].

Example 113

6-[(1S)-2-amino-1-benzyl-ethyl]-2-(4-chloro-1-methyl-1H-pyrazol-5-yl)-6,7-dihydro-5H-pyrrolo[3,4-d]pyrimidin-5-one

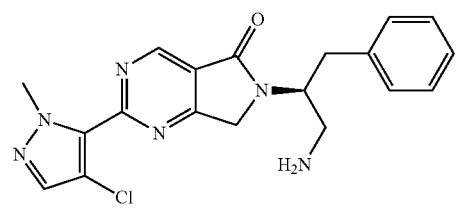 [SMILES: Cn1ncc(Cl)c1-c1ncc2c(n1)CN([C@H](CN)Cc1ccccc1)C2=O]

Step A: ethyl 2-(4-chloro-1-methyl-1H-pyrazol-5-yl)-4-methylpyrimidine-5-carboxylate

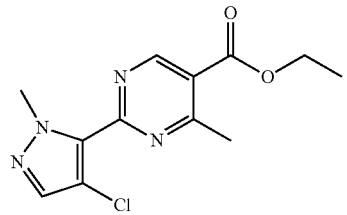 [SMILES: CCOC(=O)c1cnc(-c2c(Cl)cnn2C)nc1C]

A mixture of 4-chloro-1-methyl-5-(4,4,5,5-tetramethyl-1,3,2-dioxaborolan-2-yl)-1H-pyrazole (1.45 g, 5.98 mmol), ethyl 2-chloro-4-methylpyrimidine-5-carboxylate (0.999 g, 4.98 mmol), bis(tri-t-butylphosphine)palladium (509 mg, 0.996 mmol), and N,N-diisopropylethylamine (1.74 mL, 9.98 mmol) in 1,4-dioxane (10 mL) and water (0.5 mL) was stirred at 110° C. for 40 mins under microwave. Direct purification by combi-flash chromatography afforded 0.83 g (59% yield) of the desired product. LC-MS found: 281.1 (M+H)$^+$.

Step B: ethyl 4-(bromomethyl)-2-(4-chloro-1-methyl-1H-pyrazol-5-yl)pyrimidine-5-carboxylate

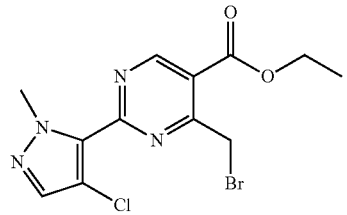 [SMILES: CCOC(=O)c1cnc(-c2c(Cl)cnn2C)nc1CBr]

To a solution of ethyl 2-(4-chloro-1-methyl-1H-pyrazol-5-yl)-4-methylpyrimidine-5-carboxylate (1 g, 3.56 mmol) in carbon tetrachloride (20.0 mL) was added N-bromosuccinimide (697 mg, 3.92 mmol) and 2,2'-azo-bis-isobutyronitrile (30 mg, 0.2 mmol), and the reaction mixture was stirred at 80° C. overnight. The reaction mixture was filtered, the filtrate was concentrated under reduced pressure, and the residue was purified by combi-flash chromatography to afford 0.78 g (61% yield) of the desired product. LC-MS found: 361.1 (M+H)$^+$.

Step C: 6-[(1S)-2-amino-1-benzyl-ethyl]-2-(4-chloro-1-methyl-1H-pyrazol-5-yl)-6,7-dihydro-5H-pyrrolo[3,4-d]pyrimidin-5-one A mixture of ethyl 4-(bromomethyl)-2-(4-chloro-1-methyl-1H-pyrazol-5-yl)pyrimidine-5-carboxylate (284.0 mg, 0.7898 mmol), tert-butyl[(2S)-2-amino-3-phenylpropyl]carbamate (198 mg, 0.791 mmol), and N,N-diisopropylethylamine (0.275 mL, 1.58 mmol) in 1-butanol (5.0 mL) was stirred at 140° C. for 2 h. The reaction mixture was evaporated under reduced pressure to give an oil residue, which was dissolved in 4 M HCl aqueous solution (2 mL, 8 mmol) and THF (2 mL). The resulting solution was stirred at room temperature for 1 hour. Direct purification on prep.HPLC afforded 81 mg (25.6% yield) of the desired product. LC-MS found: 383.1 (M+H)$^+$.

Example 114

2-[(1R)-2-amino-1-phenylethyl]-5-(4-chloro-1-methyl-1H-pyrazol-5-yl)isoindolin-1-one

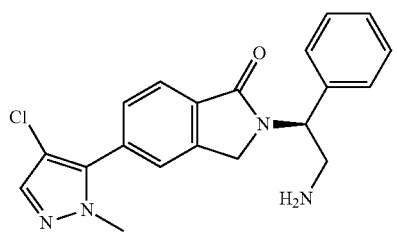 [SMILES: Cn1ncc(Cl)c1-c1ccc2c(c1)CN([C@H](CN)c1ccccc1)C2=O]

Step A: tert-butyl[(2R)-2-(5-bromo-1-oxo-1,3-dihydro-2H-isoindol-2-yl)-2phenylethyl]carbamate

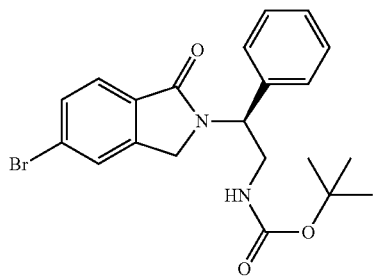 [SMILES: CC(C)(C)OC(=O)NC[C@H](c1ccccc1)N1Cc2cc(Br)ccc2C1=O]

A solution of methyl 4-bromo-2-(bromomethyl)benzoate (260.7 mg, 0.8466 mmol), tert-butyl [(2S)-2-amino-2-phenylethyl] carbamate (200.0 mg, 0.8463 mmol) and N,N-diisopropylethylamine (0.442 mL, 2.54 mmol) in 1-butanol (2 mL, 20 mmol) was stirred at 140° C. in a sealed tube for 1 h under microwave irradiation. After concentration, the residue was purified by combi-flash chromatography eluted with EtOAc/hexane (20-60%). The purification afforded 258 mg (70% yield) of the desired product as yellowish oil. LC-MS found: 432.1 (M+H)$^+$.

Step B: 2-[(1R)-2-amino-1-phenylethyl]-5-(4-chloro-1-methyl-1H-pyrazol-5-yl)isoindolin-1-one A mixture of 1-methyl-4-chloro-5-(4,4,5,5-tetramethyl-1,3,2-dioxaborolan-2-yl)-1H-pyrazole (69.5 mg, 0.334 mmol), bis(tri-t-butylphosphine)palladium (14 mg, 0.028 mmol), tert-butyl [(2S)-2-(5-bromo-1-oxo-1,3-dihydro-2H-isoindol-2-yl)-2-phenylethyl]carbamate (120.0 mg, 0.2782 mmol) and N,N-diisopropylethylamine (145 µL, 0.835 mmol) in 1,4-dioxane (1000 µL) and water (50 µL) was microwaved at 110° C. for 15 minutes. After filtering and concentration, the residue was purified by prep.—HPLC (pH=10). To the purified intermediate was added methylene chloride (0.5 mL) and trifluoroacetic acid (0.5 mL). The solution was stirred at room temperature for 1 h. After concentration, the residue was neutralized with TEA (0.5 mL) then concentrated. Purification by prep.—HPLC (pH=10) afforded 25.6 mg (25% yield) of the desired product as white solid. LC-MS found: 367.1 (M+H)+.

The following compounds listed in Table 7 were prepared by a method analogous to that for Example 114.

TABLE 7

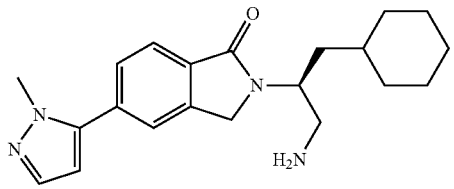

| Ex. # | $R^1$ | Q | $R^2/R^3$ | Compound | LC-MS (M + H)+ |
|---|---|---|---|---|---|
| 115 | H | H | $CH_3$ | 2-[(2-(dimethylamino)-1-phenylethyl]-5-(1-methyl-1H-pyrazol-5-yl)isoindolin-1-one | 361.2 |
| 116 | H | H | H | 2-[(1R)-2-amino-1-phenylethyl]-5-(1-methyl-1H-pyrazol-5-yl)isoindolin-1-one | 333.1 |
| 117 | H | 3-F | H | 2-[2-amino-1-(3-fluorophenyl)ethyl]-5-(1-methyl-1H-pyrazol-5-yl)isoindolin-1-one | 351.2 |
| 118 | H | 4-F | H | 2-[2-amino-1-(4-fluorophenyl)ethyl]-5-(1-methyl-1H-pyrazol-5-yl)isoindolin-1-one | 350.3 |
| 119 | H | 3-$OCH_3$ | H | 2-[2-amino-1-(3-methoxyphenyl)ethyl]-5-(1-methyl-1H-pyrazol-5-yl)isoindolin-1-one | 363.1 |
| 120 | H | 4-$OCH_3$ | H | 2-[2-amino-1-(4-methoxyphenyl)ethyl]-5-(1-methyl-1H-pyrazol-5-yl)isoindolin-1-one | 363.1 |
| 121 | Cl | H | $CH_3$ | 5-(4-chloro-1-methyl-1H-pyrazol-5-yl)-2-[2-(dimethylamino)-1-phenylethyl]isoindolin-1-one | 394.9 |
| 122 | $CH_2OPr^i$ | H | H | 2-[(1R)-2-amino-1-phenylethyl]-5-[4-(2-propoxymethyl)-1-methyl-1H-pyrazol-5-yl]isoindolin-1-one | 405.1 |
| 123 | Cl | 3-F | H | 2-[2-amino-1-(3-fluorophenyl)ethyl]-5-(4-chloro-1-methyl-1H-pyrazol-5-yl)isoindolin-1-one | 384.9 |
| 124 | Cl | 4-F | H | 2-[2-amino-1-(4-fluorophenyl)ethyl]-5-(4-chloro-1-methyl-1H-pyrazol-5-yl)isoindolin-1-one | 384.9 |
| 125 | Cl | 3-$OCH_3$ | H | 2-[2-amino-1-(3-methoxyphenyl)ethyl]-5-(4-chloro-1-methyl-1H-pyrazol-5-yl)isoindolin-1-one | 396.9 |
| 126 | Cl | 4-$OCH_3$ | H | 2-[2-amino-1-(4-methoxyphenyl)ethyl]-5-(4-chloro-1-methyl-1H-pyrazol-5-yl)isoindolin-1-one | 397.0 |

The following compounds in Table 8 were prepared by a method analogous to that for Example 1 or Example 40.

TABLE 8

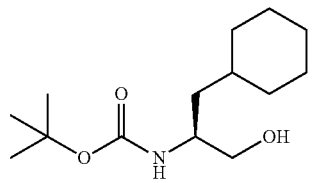 [SMILES: CC(C)(C)OC(=O)N[C@H](CO)CC1CCCCC1]

| Ex. No. | $R^7$ | $R^*$ | Compound | LC-MS (M + H)+ |
|---|---|---|---|---|
| 127 | $CH_3CH_2$ | H | 2-[(1S)-2-amino-1-(3-fluorobenzyl)ethyl]-5-(1-ethyl-1H-pyrazol-5-yl)isoindolin-1-one | 379.2 |
| 128 | $CH_3CH_2$ | F | 2-[(1S)-2-amino-1-(3,5-difluorobenzyl)ethyl]-5-(1-ethyl-1H-pyrazol-5-yl)isoindolin-1-one | 397.1 |
| 129 | $(CH_3)_2CHCH_2$ | H | 2-[(1S)-2-amino-1-(3-fluorobenzyl)ethyl]-5-(1-isobutyl-1H-pyrazol-5-yl)isoindolin-1-one | 407.1 |
| 130 | $(CH_3)_2CHCH_2$ | F | 2-[(1S)-2-amino-1-(3,5-difluorobenzyl)ethyl]-5-(1-isobutyl-1H-pyrazol-5-yl)isoindolin-1-one | 425.1 |

Example 131

Preparation of 2-[(1S)-2-amino-1-(cyclohexylmethyl)ethyl]-5-(1-methyl-1H-pyrazol-5-yl)isoindolin-1-one Step A: tert-butyl-[(1S)-2-cyclohexyl-1-(hydroxymethyl)ethyl]carbamate To a solution of (2S)-2-[(tert-butoxycarbonyl)amino]-3-cyclohexylpropanoic acid (5.0 g, 18 mmol) in tetrahydrofuran (50 mL) at 0° C. was added 1.0 M borane-THF complex in THF (55.3 mL, 55.3 mmol). After addition, the reaction mixture was stirred at room temperature for 3 hours, then cooled down with an ice-bath, and quenched by the slow addition of AcOH:MeOH (1:5, 40 mL). Then the mixture was warmed to room temperature for 2 hours. The THF volume was reduced by ½ and the product was partitioned between saturated aqueous $NaHCO_3$ and DCM. The combined organic fractions were dried over $Na_2SO_4$ and concentrated under reduced pressure to give an oil residue which was used directly in the next reaction without further purification. LC-MS found: 168.1 (M−Boc)+.

Step B: tert-butyl {(1S)-2-cyclohexyl-1-[(1,3-dioxo-1,3-dihydro-2H-isoindol-2-yl)methyl]ethyl}carbamate

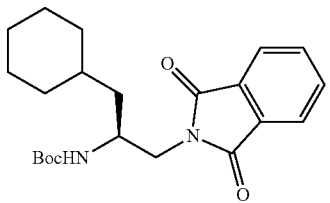 [SMILES: CC(C)(C)OC(=O)N[C@@H](CC1CCCCC1)CN1C(=O)c2ccccc2C1=O]

A mixture of tert-butyl[(1S)-2-cyclohexyl-1-(hydroxymethyl)ethyl]carbamate (3.3 g, 13 mmol), phthalimide (2.10 g, 14.3 mmol), triphenylphosphine (3.75 g, 14.3 mmol), diisopropyl azodicarboxylate (3.58 mL, 18.2 mmol) in tetrahydrofuran (30 mL, 400 mmol) was stirred at room temperature overnight. Direct purification by combi-flash chromatography afforded 2.8 g (56% yield) of the desired product. LC-MS found: 287.1 (M−Boc)+.

Step C: 2-[(2S)-2-amino-3-cyclohexylpropyl]-1H-isoindole-1,3(2H)-dione

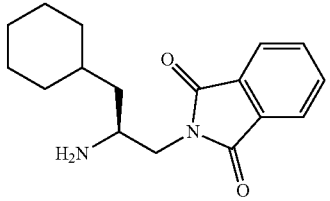 [SMILES: N[C@@H](CC1CCCCC1)CN1C(=O)c2ccccc2C1=O]

A solution of tert-butyl {(1S)-2-cyclohexyl-1-[(1,3-dioxo-1,3-dihydro-2H-isoindol-2-yl)methyl]ethyl}carbamate (2.8 g, 7.25 mmol) in 4 M HCl dioxane (10 mL, 40 mmol) and THF (10 mL) was stirred at room temperature for 2 hours. The reaction mixture was evaporated under reduced pressure to afford 2.3 g (99% yield) of the desired product. LC-MS found: 287.1 (M+H)+.

Step D: 2-[(2S)-2-(5-bromo-1-oxo-1,3-dihydro-2H-isoindol-2-yl)-3-cyclohexylpropyl]-1H-isoindole-1,3(2H)-dione

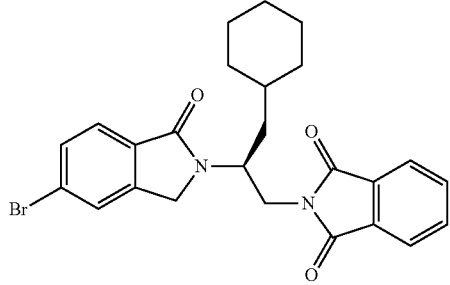 [SMILES: O=C1c2ccccc2C(=O)N1C[C@H](CC1CCCCC1)N1Cc2cc(Br)ccc2C1=O]

A mixture of 2-[(2S)-2-amino-3-cyclohexylpropyl]-1H-isoindole-1,3(2H)-dione (914.3 mg, 3.193 mmol), methyl 4-bromo-2-(bromomethyl)benzoate (960.0 mg, 3.117 mmol) and N,N-diisopropylethylamine (0.6 mL, 3 mmol) in 1-butanol (4 mL, 40 mmol) was stirred at 140° C. for 2 h under microwave irradiation. Direct purification by combi-flash chromatography afforded 810 mg (54% yield) of the desired product. LC-MS found: 481.1 (M+H)+.

Step E: 2-{(2S)-3-cyclohexyl-2-[5-(1-methyl-1H-pyrazol-5-yl)-1-oxo-1,3-dihydro-2H-isoindol-2-yl]propyl}-1H-isoindole-1,3(2H)-dione

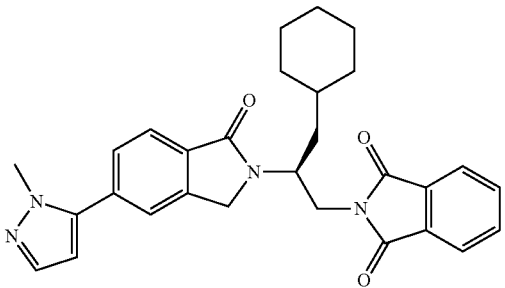 [SMILES: Cn1nccc1-c1ccc2c(c1)CN([C@@H](CC1CCCCC1)CN1C(=O)c3ccccc3C1=O)C2=O]

A mixture of 2-[(2S)-2-(5-bromo-1-oxo-1,3-dihydro-2H-isoindol-2-yl)-3-cyclohexylpropyl]-1H-isoindole-1,3(2H)-dione (103.5 mg, 0.2151 mmol), 1-methyl-5-(4,4,5,5-tetramethyl-1,3,2-dioxaborolan-2-yl)-1H-pyrazole (47 mg, 0.23 mmol), N,N-diisopropylethylamine (0.11 mL, 0.63 mmol), and bis(tri-t-butylphosphine)palladium (0.011 g, 0.021 mmol) in 1,4-dioxane (4 mL, 50 mmol) and water (0.2 mL, 10 mmol) was stirred at 110° C. for 40 min under microwave irradiation. Direct purification on prep.—HPLC afforded 30 mg (29% yield) of the desired intermediate. LC-MS found: 483.1 (M+H)+.

Step F: 2-[(1S)-2-amino-1-(cyclohexylmethyl)ethyl]-5-(1-methyl-1H-pyrazol-5-yl)isoindolin-1-one A mixture of 2-{(2S)-3-cyclohexyl-2-[5-(1-methyl-1H-pyrazol-5-yl)-1-oxo-1,3-dihydro-2H-isoindol-2-yl]propyl}-1H-isoindole-1,3(2H)-dione (30 mg, 0.062 mmol) was dissolved in methanol (3 mL, 70 mmol) and hydrazine (0.3 mL, 10 mmol). The resulting mixture was stirred at 50° C. for 2 h. Direct purification on prep.—HPLC afforded 11 mg (50% yield) of the desired final product. LC-MS found: 353.1 (M+H)+.

Example 132

Preparation of 2-[(1S)-2-amino-1-(cyclohexylmethyl)ethyl]-5-(4-chloro-1-methyl-1H-pyrazol-5-yl)isoindolin-1-one

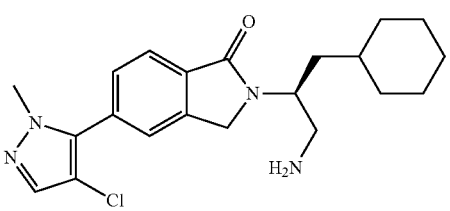 [SMILES: Cn1ncc(Cl)c1-c1ccc2c(c1)CN([C@H](CN)CC1CCCCC1)C2=O]

The title compound was prepared as a white solid according to Example 131, except substituting 4-chloro-1-methyl-5-(4,4,5,5-tetramethyl-1,3,2-dioxaborolan-2-yl)-1H-pyrazole for 1-methyl-5-(4,4,5,5-tetramethyl-1,3,2-dioxaborolan-2-yl)-1H-pyrazole. LC-MS found: 387.1 (M+H)$^+$.

Example 133

Preparation of 2-[(1S)-2-amino-1-(cyclohexylmethyl)ethyl]-5-[4-(methoxymethyl)-1-methyl-1H-pyrazol-5-yl]isoindolin-1-one

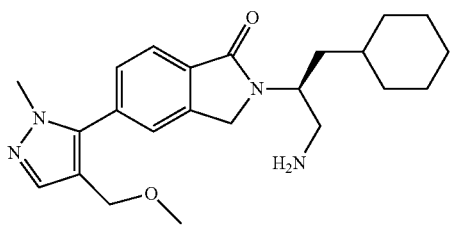 [SMILES: COCc1cnn(C)c1-c1ccc2c(c1)CN([C@H](CN)CC1CCCCC1)C2=O]

The title compound was prepared as a white solid according to Example 131, except substituting 4-methoxymethyl-1-methyl-5-(4,4,5,5-tetramethyl-1,3,2-dioxaborolan-2-yl)-1H-pyrazole for 1-methyl-5-(4,4,5,5-tetramethyl-1,3,2-dioxaborolan-2-yl)-1H-pyrazole. LC-MS found: 397.1 (M+H)$^+$.

Example 134

Preparation of 2-[(1S)-2-amino-1-(cyclohexylmethyl)ethyl]-6-(1-methyl-1H-pyrazol-5-yl)-1, 2-dihydro-3H-pyrrolo[3,4-c]pyridin-3-one

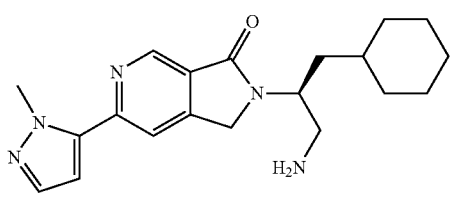 [SMILES: Cn1nccc1-c1cc2c(cn1)C(=O)N([C@H](CN)CC1CCCCC1)C2]

Step A: 2-[(2S)-2-(6-chloro-3-oxo-1,3-dihydro-2H-pyrrolo[3,4-c]pyridin-2-yl)-3-cyclohexylpropyl]-1H-isoindole-1,3(2H)-dione

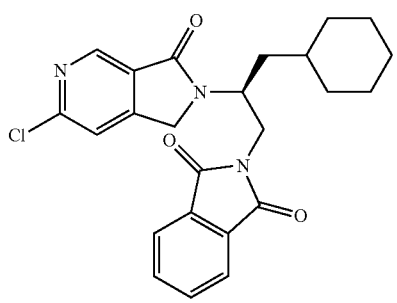 [SMILES: O=C1c2ccccc2C(=O)N1C[C@H](CC1CCCCC1)N1Cc2cc(Cl)ncc2C1=O]

A mixture of methyl 4-(bromomethyl)-6-chloronicotinate (200.0 mg, 0.7561 mmol) (prepared according to Example 119, Steps A, B and C), 2-[(2S)-2-amino-3-cyclohexylpropyl]-1H-isoindole-1,3(2H)-dione hydrochloride (244 mg, 0.754 mmol) (prepared from Example 79, Step A) and N,N-diisopropylethylamine (0.526 mL, 3.02 mmol) in 1-butanol (5.0 mL, 55 mmol) was stirred at 140° C. for 2 h under microwave irradiation. Direct purification on prep.HPLC afforded 182 mg (55.1% yield) of the desired product. LC-MS found: 438.1 (M+H)$^+$.

Step B: 2-[(1S)-2-amino-1-(cyclohexylmethyl)ethyl]-6-(1-methyl-1H-pyrazol-5-yl)-1,2-dihydro-3H-pyrrolo[3,4-c]pyridin-3-one

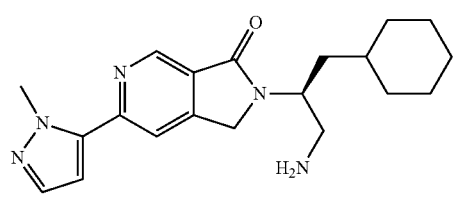 [SMILES: Cn1nccc1-c1cc2c(cn1)C(=O)N([C@H](CN)CC1CCCCC1)C2]

A mixture of 2-[(2S)-2-(6-chloro-3-oxo-1,3-dihydro-2H-pyrrolo[3,4-c]pyridin-2-yl)-3-cyclohexylpropyl]-1H-isoindole-1,3(2H)-dione (100.0 mg, 0.2284 mmol), 1-methyl-5-(4,4,5,5-tetramethyl-1,3,2-dioxaborolan-2-yl)-1H-pyrazole (95.0 mg, 0.456 mmol), bis(tri-t-butylphosphine)palladium (23 mg, 0.045 mmol), and N,N-diisopropylethylamine (0.119 mL, 0.683 mmol) in 1,4-dioxane (5.0 mL, 64 mmol) and water (0.5 mL, 30 mmol) was stirred at 110° C. for 40 min under microwave irradiation. Direct purification on prep.HPLC afforded 33 mg (30% yield) of the desired intermediate as white powder. LC-MS found: 484.1 (M+H)$^+$. The above white powder (33 mg, 0.068 mmol) was dissolved in hydrazine (1 mL, 30 mmol) and methanol (5 mL, 100 mmol). The resulting solution was stirred at 50° C. for 2 h. Direct purification on prep.HPLC afforded 12 mg (46% yield) of the final desired product. LC-MS found: 354.1 (M+H)$^+$.

Example 135

Preparation of 2-[(1S)-2-amino-1-(cyclohexylmethyl)ethyl]-6-(4-chloro-1-methyl-1H-pyrazol-5-yl)-1,2-dihydro-3H-pyrrolo[3,4-c]pyridin-3-one

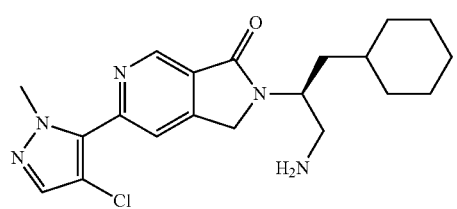 [SMILES: Cn1ncc(Cl)c1-c1cc2c(cn1)C(=O)N([C@H](CN)CC1CCCCC1)C2]

The title compound was prepared as a white solid according to Example 133, except substituting 4-chloro-1-methyl-5-(4,4,5,5-tetramethyl-1,3,2-dioxaborolan-2-yl)-1H-pyrazole for 1-methyl-5-(4,4,5,5-tetramethyl-1,3,2-dioxaborolan-2-yl)-1H-pyrazole. LC-MS found: 388.1 (M+H)⁺.

Example 136

Preparation of 2-[(1S)-2-amino-1-(cyclopropylmethyl)ethyl]-5-(1-methyl-1H-pyrazol-5

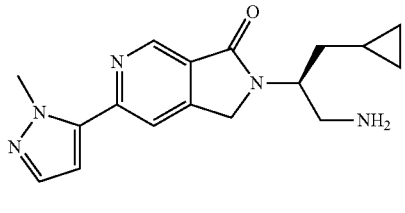 [SMILES: Cn1nccc1-c1cc2c(cn1)C(=O)N([C@H](CN)CC1CC1)C2]

Step A: tert-butyl[(1S)-2-cyclopropyl-1-(hydroxymethyl)ethyl]carbamate

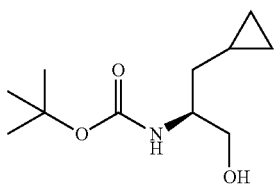

To a solution of (2S)-2-[(tert-butoxycarbonyl)amino]-3-cyclopropylpropanoic acid (2.5 g, 11 mmol) in tetrahydrofuran (30 mL) at 0° C. was added 1.0 M borane-THF complex in THF (32.4 mL). After addition, the reaction mixture was stirred at room temperature for 3 hours, then cooled down with an ice-bath, quenched by the slow addition of AcOH:MeOH (1:5, 20 mL) and the mixture was then warmed to room temperature for 2 hours. The THF volume was reduced by ½ and the product was partitioned between saturated aqueous NaHCO₃ and DCM. The combined organic fractions were dried over Na₂SO₄ and concentrated under reduced pressure to give an oil residue, which was used directly in the next reaction without further purification. LC-MS found: 216.1 (M+H)⁺.

Step B: 2-[(2S)-2-amino-3-cyclopropylpropyl]-1H-isoindole-1,3(2H)-dione hydrochloride

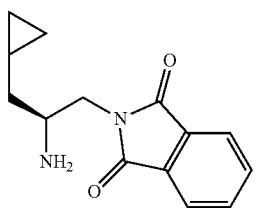 [SMILES: N[C@@H](CC1CC1)CN1C(=O)c2ccccc2C1=O]

A mixture of tert-butyl[(1S)-2-cyclopropyl-1-(hydroxymethyl)ethyl]-carbamate (250.5 mg, 1.1 mmol), phthalimide (171 mg, 1.16 mmol), triphenylphosphine (305 mg, 1.16 mmol), and diisopropyl azodicarboxylate (0.229 mL, 1.16 mmol) in tetrahydrofuran (50.1 mL, 618 mmol) was stirred at room temperature overnight. Direct purification by combiflash chromatography afforded 310 mg (77% yield) of the desired intermediate. LC-MS found: 245.1 (M–Boc)⁺.

The above intermediate (310 mg, 0.90 mmol) was dissolved in 4 M HCl dioxane (5 mL, 20 mmol) and THF (5 mL). The resulting solution was stirred at room temperature for 2 h, then evaporated under reduced pressure to give the desired final product. LC-MS found: 245.1 (M+H)⁺.

Step C: 2-{(2S)-3-cyclopropyl-2-[5-(1-methyl-1H-pyrazol-5-yl)-1-oxo-1,3-dihydro-2H-isoindol-2-yl]propyl}-1H-isoindole-1,3(2H)-dione

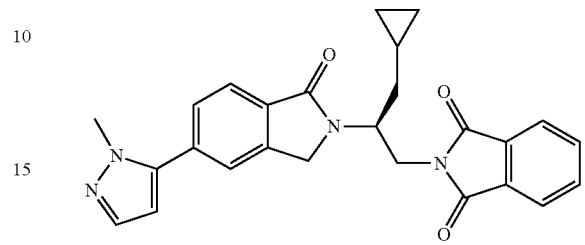

A mixture of 2-[(2S)-2-amino-3-cyclopropylpropyl]-1H-isoindole-1,3(2H)-dione hydrochloride (257.75 mg, 0.91806 mmol), methyl 4-bromo-2-(bromomethyl)-benzoate (275.80 mg, 0.89555 mmol), N,N-diisopropylethylamine (0.50 mL, 2.9 mmol) and 1,4-dioxane (5.0 mL, 64 mmol) was stirred at 130° C. for 2 hours under microwave irradiation. After the reaction was completed, 1-methyl-5-(4,4,5,5-tetramethyl-1,3,2-dioxaborolan-2-yl)-1H-pyrazole (250.1 mg, 1.202 mmol), bis(tri-t-butylphosphine)palladium (51.1 mg, 0.100 mmol) and water were added. The reaction mixture was stirred at 110° C. for 40 mins under microwave irradiation. Direct purification on prep.HPLC afforded 56 mg (14.2% yield) of the desired final compound. LC-MS found: 441.1 (M+H)⁺.

Step D: 2-[(1S)-2-amino-1-(cyclopropylmethyl)ethyl]-5-(1-methyl-1H-pyrazol-5-yl)isoindolin-1-one 2-{(2S)-3-Cyclopropyl-2-[5-(1-methyl-1H-pyrazol-5-yl)-1-oxo-1,3-dihydro-2H-isoindol-2-yl]propyl}-1H-isoindole-1,3(2H)-dione (56 mg, 0.13 mmol) was dissolved in hydrazine (1 mL, 30 mmol) and methanol (5 mL). The resulting solution was stirred at room temperature for 2 h. Direct purification on prep.HPLC afforded 15 mg (37% yield) of the final desired product. LC-MS found: 311 (M+H)⁺.

Example 137

Preparation of 2-[(1S)-2-amino-1-(cyclopropylmethyl)ethyl]-5-(4-chloro-1-methyl-1H-pyrazol-5-yl)isoindolin-1-one

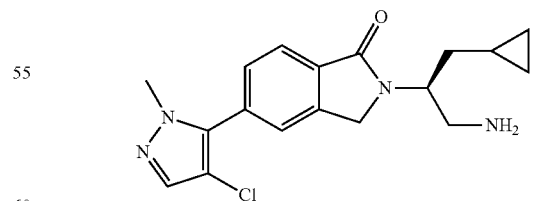

The title compound was prepared as a white solid according to Example 135, except substituting 4-chloro-1-methyl-5-(4,4,5,5-tetramethyl-1,3,2-dioxaborolan-2-yl)-1H-pyrazole for 1-methyl-5-(4,4,5,5-tetramethyl-1,3,2-dioxaborolan-2-yl)-1H-pyrazole. LC-MS found: 345.1 (M+H)⁺.

Example A

In Vitro Akt Kinase Enzymatic Assay

Compounds herein were tested for inhibitory activity of Akt targets according to the following in vitro assay. Full length Akt1 (cat #P2999), Akt2 (cat #PV3184), Akt3 (cat #PV3185), peptide substrate, Ulight-Crosstide (cat #TRF0106-M), Ultra-Europium anti-phospho-Crosstide (cat #TRF-0202-M), and 10×LANCE detection buffer (cat #CR97-100) were purchased from PerkinElmer. In general, assay buffer conditions were chosen based on obtaining optimal enzymatic and linear activities. The assay buffer contains 50 mM HEPES, 10 mM $MgCl_2$, 5 mM DTT, 0.005% Tween20 at pH 7.8. Compound stock (0.001 mM) was prepared in DMSO. The compound plate was prepared by 3-fold and 11-point serial dilutions. 0.5 μL of the compound in DMSO was transferred from the compound plate to the assay plate. Enzyme solution (0.4 nM of Akt1, 0.6 nM of Akt2 or 0.6 nM of Akt3) was prepared in the assay buffer. Note that the enzyme concentration given is based on the given stock concentration reported by the vendor. 0.1 μM substrate solution was prepared in the assay buffer with addition of 5 mM ATP. 10 μL of the enzyme solution was added to the assay plate and then 10 μL of substrate solution was added to the assay plate. The plate was protected from light and the reaction was incubated at 25° C. for 1 hr. The reaction was stopped by adding 10 μL of a solution containing 30 mM EDTA, and 3 nM Ultra Europium anti-phospho Crosstide in 1× detection buffer. The plate was incubated for 15-30 min at room temperature and HTRF (homogenous time resolved fluorescence) was measured on a plate reader. Percentage of inhibition was calculated for each concentration and $IC_{50}$ value was generated from curve fitting. See Table 8 for data related to compounds of the examples.

Example B

PKA In Vitro Enzymatic Assay

Full length PKA (cat #P2912), peptide substrate, fluorescein CREBtide peptide (cat #PV3508), Tb-Crebtide p-S133 Ab (cat #PV3566), and Lanthascreen TR-FRET Dilution Buffer stored (part # PV3574) were purchased from Invitrogen. In general, assay buffer conditions were chosen based on obtaining optimal and linear enzymatic activities. The assay buffer contains 50 mM HEPES, 10 mM $MgCl_2$, 5 mM DTT, 0.005% Tween20 at pH 7.8. Compound stock (0.001 mM) was prepared in DMSO. The compound plate was prepared by 3-fold and 11-point serial dilutions. 0.5 μL of the compound in DMSO was transferred from the compound plate to the assay plate. 0.035 nM enzyme solution was prepared in the assay buffer. Note that the enzyme concentration given is based on the given stock concentration reported by the vendor. 0.1 μM substrate solution was prepared in the assay buffer with addition of 5 mM ATP. 10 μL of the enzyme solution was added to the assay plate and then 10 μL of substrate solution was added to the assay plate. The plate was protected from light and the reaction was incubated at 25° C. for 1 hr. The reaction was stopped by adding 10 μL of a solution containing 30 mM EDTA, and 1.5 nM Tb-Crebtide p-S133 Ab in 1× detection buffer. The plate was incubated for 15-30 min at room temperature and HTRF (homogenous time resolved fluorescence) was measured on a plate reader. Percentage of inhibition was calculated for each concentration and $IC_{50}$ value was generated from curve fitting. See Table 8 for data related to compounds of the examples.

Example C

Akt LNCaP Proliferation Assay

LNCaP cells (human prostate tumor cell line) were plated in 96 well plates (COSTAR, Corning, N.Y.) in 50 μL at 10,000 cells/well in RPMI (Media Tech, Manassas, Va.), 2% fetal bovine serum (Hyclone/Thermo, Logan, Utah) and incubated overnight at 37° C., 5% $CO_2$. 50 mL of compound solution were added at final concentrations of 1000 nM to 0.5 nM in 3 fold dilutions for $IC_{50}$ determination and plates further incubated for 48 hours. 100 μL of Cell Titer 96® Aqueous reagent, from an MTS colorimetric method for determining the number of viable cells in proliferation (Cell titer 96, Promega, Madison, Wis.) was added for 2 hours at 37° C., 5% $CO_2$. Each plate was mixed well and read on a SpectroMax M5 automated plate reader (Molecular Devices, Sunnyvale Calif.). The ability of the compound to inhibit proliferation was reported as the inhibitor concentration required for 50% inhibition ($IC_{50}$ values) of total cell proliferation. See Table 8 for data related to compounds of the examples.

Example D

$IC_{50}$ Data $IC_{50}$ data collected for the Example compounds with respect to the assays described above in Examples A, B, and C is provided below in Table 9 where "+" indicates less than 500 nM; "++" indicates 500 to 5000 nM; "+++" indicates greater than 5000 nM; and "ND" indicates that the measurement was not determined.

TABLE 9

| | $IC_{50}$ data | | | | |
|---|---|---|---|---|---|
| Example | Akt1 | Akt2 | Akt3 | PKA | LNCaP |
| 1 | + | + | + | ++ | + |
| 2 | + | + | + | ++ | + |
| 3 | + | + | + | ++ | + |
| 4 | + | + | + | +++ | + |
| 5 | + | + | + | +++ | + |
| 6 | + | + | + | +++ | + |
| 7 | + | + | + | +++ | + |
| 8 | + | + | + | ++ | + |
| 9 | + | + | + | +++ | + |
| 10 | + | ++ | ++ | +++ | ++ |
| 11 | + | + | + | ++ | + |
| 12 | + | + | + | ++ | + |
| 13 | + | + | + | +++ | + |
| 14 | ++ | ++ | + | +++ | ND |
| 15 | ++ | +++ | + | +++ | ND |
| 16 | ++ | ++ | + | +++ | ND |
| 17 | +++ | +++ | +++ | +++ | ND |
| 18 | +++ | +++ | ++ | +++ | ND |
| 19 | + | ++ | ++ | +++ | ++ |
| 20 | + | ++ | ++ | +++ | ND |
| 21 | ++ | +++ | + | +++ | ND |
| 22 | +++ | +++ | +++ | +++ | ND |
| 23 | +++ | +++ | +++ | +++ | ND |
| 24 | +++ | +++ | +++ | +++ | ND |
| 25 | +++ | +++ | +++ | +++ | ND |
| 26 | +++ | +++ | +++ | +++ | ND |
| 27 | +++ | +++ | +++ | +++ | ND |
| 28 | ++ | +++ | +++ | +++ | ND |
| 29 | ++ | +++ | +++ | +++ | ND |
| 30 | + | ++ | ++ | +++ | ND |
| 31 | + | ++ | ++ | +++ | ND |

TABLE 9-continued

IC$_{50}$ data

| Example | Akt1 | Akt2 | Akt3 | PKA | LNCaP |
|---|---|---|---|---|---|
| 32 | ++ | ++ | ++ | +++ | ND |
| 33 | + | ++ | ++ | +++ | ND |
| 34 | + | ++ | ++ | +++ | ND |
| 35 | + | ++ | ++ | +++ | ND |
| 36 | ++ | ++ | +++ | +++ | ND |
| 37 | + | ++ | ++ | +++ | ND |
| 38 | ++ | +++ | +++ | +++ | ND |
| 39 | + | +++ | ++ | +++ | ND |
| 40 | + | + | + | ++ | + |
| 41 | + | + | + | ++ | + |
| 42 | + | + | + | ++ | + |
| 43 | + | + | + | +++ | + |
| 44 | + | + | + | ++ | + |
| 45 | + | + | + | ++ | + |
| 46 | + | + | + | ++ | + |
| 47 | + | + | + | ++ | + |
| 48 | + | + | + | ++ | + |
| 49 | + | ++ | + | +++ | ++ |
| 50 | + | + | + | +++ | + |
| 51 | + | + | + | + | + |
| 52 | + | + | + | ++ | + |
| 53 | + | + | + | ++ | + |
| 54 | + | + | + | +++ | + |
| 55 | + | + | + | +++ | + |
| 56 | + | + | + | ++ | + |
| 57 | + | + | + | +++ | + |
| 58 | + | + | + | +++ | + |
| 59 | + | ++ | ++ | +++ | -- |
| 60 | + | + | + | +++ | + |
| 61 | + | + | + | ++ | ++ |
| 62 | + | + | + | +++ | + |
| 63 | + | ++ | ++ | +++ | ND |
| 64 | ++ | +++ | +++ | +++ | ND |
| 65 | + | + | + | +++ | + |
| 66 | + | + | + | ++ | + |
| 67 | + | + | + | ++ | + |
| 68 | + | + | + | ++ | + |
| 69 | + | ++ | ++ | ++ | +++ |
| 70 | + | +++ | ++ | +++ | ND |
| 71 | + | ++ | ++ | +++ | ND |
| 72 | +++ | +++ | +++ | +++ | >1000 |
| 73 | ++ | +++ | ++ | +++ | >1000 |
| 74 | ++ | +++ | +++ | +++ | >1000 |
| 75 | ++ | + | ++ | +++ | + |
| 76 | + | + | + | +++ | + |
| 77 | ++ | +++ | +++ | +++ | ND |
| 78 | + | + | ++ | +++ | + |
| 79 | + | + | ++ | +++ | ++ |
| 80 | + | + | + | ++ | + |
| 81 | + | + | + | ++ | + |
| 82 | + | ++ | ++ | +++ | ND |
| 83 | ++ | ++ | +++ | +++ | ND |
| 84 | + | ++ | ++ | +++ | ND |
| 85 | +++ | +++ | +++ | +++ | >1000 |
| 86 | ++ | +++ | +++ | +++ | >1000 |
| 87 | ++ | +++ | +++ | +++ | >1000 |
| 88 | + | + | + | ++ | + |
| 89 | + | + | + | ++ | + |
| 90 | + | + | + | +++ | + |
| 91 | + | + | + | +++ | + |
| 92 | + | + | + | ++ | + |
| 93 | + | + | + | ++ | + |
| 94 | + | + | + | ++ | + |
| 95 | + | + | + | +++ | + |
| 96 | + | + | + | +++ | -- |
| 97 | + | + | + | +++ | + |
| 98 | ++ | +++ | ++ | +++ | ND |
| 99 | + | ++ | ++ | +++ | ND |
| 100 | + | + | + | ++ | + |
| 101 | + | + | + | ++ | + |
| 102 | + | + | + | ++ | + |
| 103 | + | + | + | ++ | + |
| 104 | + | + | + | ++ | + |
| 105 | + | ++ | + | +++ | ++ |
| 106 | + | + | + | +++ | + |
| 107 | + | + | + | +++ | + |
| 108 | + | + | + | ++ | + |
| 109 | + | ++ | ++ | +++ | ND |
| 110 | + | ++ | ++ | +++ | ND |
| 111 | ++ | ++ | +++ | +++ | ND |
| 112 | ++ | ++ | ++ | +++ | ND |
| 113 | + | ++ | ++ | +++ | ND |
| 114 | + | ++ | ++ | +++ | ND |
| 115 | ++ | +++ | +++ | +++ | ND |
| 116 | + | + | ++ | ++ | + |
| 117 | + | + | ++ | ++ | + |
| 118 | + | ++ | +++ | +++ | ND |
| 119 | + | + | ++ | ++ | ND |
| 120 | +++ | +++ | +++ | +++ | ND |
| 121 | +++ | +++ | +++ | +++ | ND |
| 122 | + | ++ | ++ | +++ | ND |
| 123 | + | ++ | ++ | ++ | ND |
| 124 | ++ | ++ | ++ | +++ | ND |
| 125 | + | ++ | ++ | +++ | ND |
| 126 | +++ | +++ | +++ | +++ | ND |
| 127 | + | + | + | +++ | + |
| 128 | + | + | + | +++ | + |
| 129 | ++ | +++ | +++ | +++ | >1000 |
| 130 | ++ | +++ | +++ | +++ | >1000 |
| 131 | + | + | + | ++ | + |
| 132 | + | + | + | ++ | + |
| 133 | + | ++ | ++ | +++ | ++ |
| 134 | + | + | + | + | + |
| 135 | + | + | + | ++ | + |
| 136 | + | ++ | +++ | +++ | ND |
| 137 | ++ | ++ | ++ | +++ | ND |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

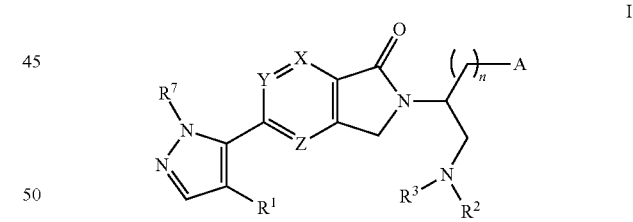

or a pharmaceutically acceptable salt thereof, wherein:
X is N or $CR^4$;
Y is N or $CR^5$;
Z is N or $CR^6$, provided at least one of X, Y, and Z comprises a carbon atom;
A is $C_{6-10}$ aryl, 5-10 membered heteroaryl, or $C_{3-7}$ cycloalkyl, wherein said $C_{6-10}$ aryl, 5-10 membered heteroaryl, and $C_{3-7}$ cycloalkyl are each optionally substituted with 1, 2, 3, 4, or 5 substituents independently selected from Q;
$R^1$ is H, F, Cl, Br, CN, $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 4-6 membered heterocycloalkyl, or 5-10 membered heteroaryl, wherein said $C_{1-6}$ alkyl, $C_{2-6}$ alkenyl, $C_{2-6}$ alkynyl, $C_{3-6}$ cycloalkyl, $C_{6-10}$ aryl, 4-6 membered heterocycloalkyl, and 5-10 membered heteroaryl are each optionally substituted with 1, 2, or 3 substituents independently selected from Cy, halo, $C_{1-6}$ alkyl, $C_{2-6}$ alkenyl, $C_{2-6}$ alkynyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^c(O)R^b$, $NR^cC(O)NR^cR^d$, $NR^cC(O)OR^a$, $C(=NR^g)NR^cR^d$, $NR^cC(=NR^g)NR^cR^d$, $S(O)R^b$, $S(O)NR^cR^d$, $S(O)_2R^b$, $NR^cS(O)_2R^b$, and $S(O)_2NR^cR^d$, wherein no more than one of said 1, 2, or 3 substituents is Cy;

$R^2$ is H, $C_{1-6}$ alkyl, $C_{3-6}$ cycloalkyl, or 4-6 membered heterocycloalkyl, wherein said 4-6 membered heterocycloalkyl is optionally substituted by 1, 2, or 3 substituents independently selected from $R^A$;

$R^3$ is H or $C_{1-3}$ alkyl;

or $R^2$ and $R^3$ together with the nitrogen atom to which they are both attached form a 4-6 membered heterocycloalkyl group optionally substituted by 1 or 2 substituents independently selected from $R^A$;

$R^4$ is H, F, Cl, CN, or $C_{1-3}$ alkyl;

$R^5$ is H, F, Cl, CN, or $C_{1-3}$ alkyl;

$R^6$ is H, F, Cl, CN, or $C_{1-3}$ alkyl;

$R^7$ is $C_{1-3}$ alkyl;

Q is independently selected from $Cy^1$, -L-$Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; wherein no more than two Q are independently selected from $Cy^1$ and -L-$Cy^1$, and wherein said $C_{1-6}$ alkyl, $C_{2-6}$ alkenyl, $C_{2-6}$ alkynyl, and $C_{1-6}$ haloalkyl, are each optionally substituted by 1, 2, 3, 4 or 5 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

L is $C_{1-3}$ alkylene, $(C_{1-3}$ alkylene$)_pO(C_{1-3}$ alkylene$)_q$, $(C_{1-3}$ alkylene$)_pS(C_{1-3}$ alkylene$)_q$, $(C_{1-3}$ alkylene$)_pC(O)(C_{1-3}$ alkylene$)_q$, $(C_{1-3}$ alkylene$)_pC(O)NR^e(C_{1-3}$ alkylene$)_q$, $(C_{1-3}$ alkylene$)_pC(O)O(C_{1-3}$ alkylene$)_q$, $(C_{1-3}$ alkylene$)_pOC(O)(C_{1-3}$ alkylene$)_q$, $(C_{1-3}$ alkylene$)_pOC(O)NR^e(C_{1-3}$ alkylene$)_q$, $(C_{1-3}$ alkylene$)_pNR^e(C_{1-3}$ alkylene$)_q$, $(C_{1-3}$ alkylene$)_pNR^eC(O)NR^f(C_{1-3}$ alkylene$)_q$, $(C_{1-3}$ alkylene$)_pS(O)(C_{1-3}$ alkylene$)_q$, $(C_{1-3}$ alkylene$)_pS(O)NR^e(C_{1-3}$ alkylene$)_q$, $(C_{1-3}$ alkylene$)_pS(O)_2(C_{1-3}$ alkylene$)_q$, or $(C_{1-3}$ alkylene$)_pS(O)_2NR^e(C_{1-3}$ alkylene$)_q$, wherein said $C_{1-3}$ alkylene occurring in any of the options for L is optionally substituted with 1, 2, or 3 substituents independently selected from F, Cl, CN, $NH_2$, $NH(C_{1-3}$ alkyl) and $N(C_{1-3}$ alkyl$)_2$;

Cy is $C_{3-6}$ cycloalkyl, $C_{6-10}$ aryl, 4-6 membered heterocycloalkyl, or 5-10 membered heteroaryl, wherein said $C_{3-6}$ cycloalkyl, $C_{6-10}$ aryl, 4-6 membered heterocycloalkyl, and 5-10 membered heteroaryl are each optionally substituted by 1, 2, or 3 substituents independently selected from $Cy^2$ and $R^B$, wherein no more than one of said 1, 2, or 3 substituents is $Cy^2$;

$Cy^1$ is $C_{3-6}$ cycloalkyl, $C_{6-10}$ aryl, 4-6 membered heterocycloalkyl, or 5-6 membered heteroaryl, wherein said $C_{3-6}$ cycloalkyl, $C_{6-10}$ aryl, 4-6 membered heterocycloalkyl, and 5-6 membered heteroaryl are each optionally substituted with 1, 2, or 3 substituents independently selected from $R^C$;

$Cy^2$ is $C_{3-6}$ cycloalkyl, $C_{6-10}$ aryl, 4-6 membered heterocycloalkyl, or 5-6 membered heteroaryl, wherein said $C_{3-6}$ cycloalkyl, $C_{6-10}$ aryl, 4-6 membered heterocycloalkyl, and 5-6 membered heteroaryl are each optionally substituted with 1, 2, or 3 substituents independently selected from $R^D$;

$R^A$, $R^B$, $R^C$, and $R^D$ are each independently selected from halo, CN, $C_{1-3}$ alkyl, $C_{1-3}$ haloalkyl, $NO_2$, $OR^{a2}$, $C(O)R^{b2}$, $C(O)NR^{c2}R^{d2}$, $C(O)OR^{a2}$, $OC(O)R^{b2}$, $NR^{c1}R^{d1}$, $NR^{c2}C(O)R^{b2}$, $NR^{c2}C(O)NR^{c2}R^{d2}$, $NR^{c2}C(O)OR^{a2}$, $S(O)_2R^{b2}$, $NR^{c2}S(O)_2R^{b2}$, and $S(O)_2NR^{c2}R^{d2}$;

$R^a$, $R^b$, $R^c$, $R^d$, $R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl, wherein said $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl are each optionally substituted with 1, 2, 3, 4, or 5 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

or $R^c$ and $R^d$ together with the N atom to which they are attached form a 4-, 5-, 6- or 7-membered heterocycloalkyl group or 5-membered heteroaryl group, each optionally substituted with 1, 2, or 3 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

or $R^{c1}$ and $R^{d1}$ together with the N atom to which they are attached form a 4-, 5-, 6- or 7-membered heterocycloalkyl group or 5-membered heteroaryl group, each optionally substituted with 1, 2, or 3 substituents independently selected from $C_{1-6}$ alkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

$R^{a2}$, $R^{b2}$, $R^{c2}$, and $R^{d2}$ are each independently selected from H, $C_{1-3}$ alkyl, and $C_{3-6}$ cycloalkyl;

or $R^{c2}$ and $R^{d2}$ together with the N atom to which they are attached form a 4-, 5-, or 6-membered heterocycloalkyl group or 5-membered heteroaryl group;

$R^{a3}$, $R^{b3}$, $R^{c3}$, and $R^{d3}$ are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl, and 4-10 membered heterocycloalkyl-$C_{1-3}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c3}$ and $R^{d3}$ together with the N atom to which they are attached form a 4-, 5-, 6- or 7-membered heterocycloalkyl group or 5-membered heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$ and $R^f$ are each independently selected from H and $C_{1-4}$ alkyl;

$R^g$ is H, CN, or $NO_2$;

n is 0 or 1;

p is 0 or 1; and q is 0 or 1.

2. The compound according to claim 1, or a pharmaceutically acceptable salt thereof, wherein X is $CR^4$; Y is $CR^5$; and Z is $CR^6$.

3. The compound according to claim 1, or a pharmaceutically acceptable salt thereof, wherein X is N; Y is $CR^5$; and Z is $CR^6$.

4. The compound according to claim 1, or a pharmaceutically acceptable salt thereof, wherein X is $CR^4$; Y is N; and Z is $CR^6$.

5. The compound according to claim 1, or a pharmaceutically acceptable salt thereof, wherein X is $CR^4$; Y is $CR^5$; and Z is N.

6. The compound according claim 1, or a pharmaceutically acceptable salt thereof, wherein $R^2$ is H, $C_{1-6}$ alkyl, $C_{3-6}$ cycloalkyl, or 4-6 membered heterocycloalkyl, wherein said 4-6 membered heterocycloalkyl is optionally substituted by $C_{1-3}$ alkyl.

7. The compound according to claim 1, or a pharmaceutically acceptable salt thereof, wherein $R^2$ is H or $C_{1-6}$ alkyl.

8. The compound according to claim 1, or a pharmaceutically acceptable salt thereof, wherein $R^3$ is H.

9. The compound according to claim 1, or a pharmaceutically acceptable salt thereof, wherein $R^2$ and $R^3$ are both H.

10. The compound according to claim 1, or a pharmaceutically acceptable salt thereof, wherein $R^1$ is H, F, Cl, Br, CN, $C_{1-6}$ alkyl, $C_{2-6}$ alkynyl, $C_{6-10}$ aryl, or 5-10 membered heteroaryl, wherein said $C_{1-6}$ alkyl, $C_{2-6}$ alkynyl, $C_{6-10}$ aryl, 4-6 membered heterocycloalkyl, and 5-10 membered heteroaryl are each optionally substituted with one substituent selected from halo, $C_{1-6}$ alkyl, $OR^a$, $SR^a$, and $C(O)NR^cR^d$.

11. The compound according to claim 1, or a pharmaceutically acceptable salt thereof, wherein $R^1$ is selected from H, F, Cl, Br, CN, methyl, methoxymethyl, ethoxymethyl, n-propyloxymethyl, isopropyloxymethyl, cyclobutyloxymethyl, cyclopropylmethyloxymethyl, methylthiomethyl, ethylthiomethyl, phenyl, thienyl, pyridinyl, methylpyrazolyl, thiazolyl, naphthyl, pyrimidinyl, fluoropyridinyl, methoxypyridinyl, methylaminocarbonylpyridinyl, and hydroxymethylbutynyl.

12. The compound according to claim 1, or a pharmaceutically acceptable salt thereof, wherein $R^1$ is selected from H, F, Cl, Br, CN, and methyl.

13. The compound according to claim 1, or a pharmaceutically acceptable salt thereof, wherein $R^1$ is H.

14. The compound according to claim 1, or a pharmaceutically acceptable salt thereof, wherein A is phenyl optionally substituted with 1, 2, 3, 4, or 5 substituents independently selected from Q.

15. The compound according to claim 1, or a pharmaceutically acceptable salt thereof, wherein A is 5-10 membered heteroaryl optionally substituted with 1, 2, 3, 4, or 5 substituents independently selected from Q.

16. The compound according to claim 1, or a pharmaceutically acceptable salt thereof, wherein A is selected from pyridinyl, thienyl, thiazolyl, and pyrazolyl, each optionally substituted with 1, 2, 3, 4, or 5 substituents independently selected from Q.

17. The compound according to claim 1, or a pharmaceutically acceptable salt thereof, wherein A is $C_{3-7}$ cycloalkyl optionally substituted with 1, 2, 3, 4, or 5 substituents independently selected from Q.

18. The compound according to claim 1, or a pharmaceutically acceptable salt thereof, wherein A is cyclohexyl or cyclopropyl.

19. The compound according to claim 1, or a pharmaceutically acceptable salt thereof, wherein Q is independently selected from $Cy^1$, halo, $C_{2-6}$ alkynyl, $C_{1-6}$ haloalkyl, CN, and $OR^{a1}$.

20. The compound according to claim 1, or a pharmaceutically acceptable salt thereof, wherein Q is independently selected from F, trifluoromethyl, methoxy, CN, acetylene, methylpyrazolyl, thienyl, pyridinyl, and pyrimidinyl.

21. The compound according to any claim 1, or a pharmaceutically acceptable salt thereof, wherein $R^4$, $R^5$, and $R^6$ are each H.

22. The compound according to claim 1, or a pharmaceutically acceptable salt thereof, wherein $R^7$ is methyl, or ethyl,.

23. The compound according to claim 1, or a pharmaceutically acceptable salt thereof, wherein $R^7$ is methyl.

24. The compound according to claim 1, or a pharmaceutically acceptable salt thereof, wherein n is 1.

25. The compound according to claim 1, or a pharmaceutically acceptable salt thereof, wherein n is 0.

26. The compound according to claim 1, or a pharmaceutically acceptable salt thereof, wherein:

X is N or CH;

Y is N or CH;

Z is N or CH, provided at least two of X, Y, and Z are CH;

$R^1$ is H, F, Cl, Br, CN, methyl, methoxymethyl, ethoxymethyl, n-propyloxymethyl, isopropyloxymethyl, cyclobutyloxymethyl, cyclopropylmethyloxymethyl, methylthiomethyl, ethylthiomethyl, phenyl, thienyl, pyridinyl, methylpyrazolyl, thiazolyl, naphthyl, pyrimidinyl, fluoropyridinyl, methoxypyridinyl, methylaminocarbonylpyridinyl, or hydroxymethylbutynyl;

$R^2$ is H or methyl;

$R^3$ is H or methyl;

$R^7$ is methyl;

A is phenyl, pyridinyl, thienyl, thiazolyl, pyrazolyl, cyclohexyl, or cyclopropyl, each optionally substituted with 1, 2, or 3 substituents independently selected from F, trifluoromethyl, methoxy, CN, acetylene, methylpyrazolyl, thienyl, pyridinyl, and pyrimidinyl; and n is 0 or 1.

27. The compound according to claim 1, having Formula IIa or IIb:

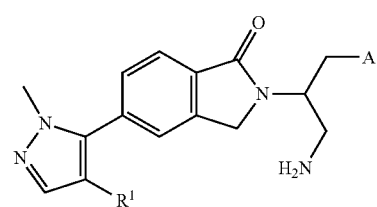

IIa

-continued

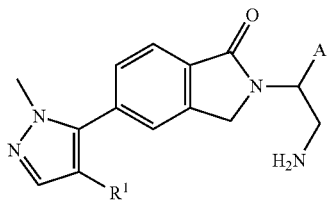

or a pharmaceutically acceptable salt thereof.

28. The compound according to claim 1, having Formula III:

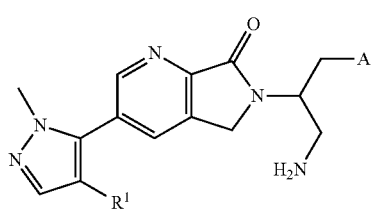

or a pharmaceutically acceptable salt thereof.

29. The compound according to claim 1, having Formula IV:

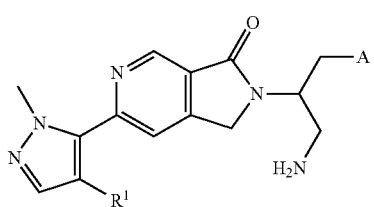

or a pharmaceutically acceptable salt thereof.

30. The compound according to claim 1, having Formula V:

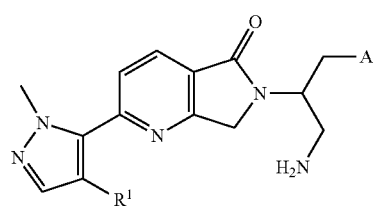

or a pharmaceutically acceptable salt thereof.

31. The compound according to claim 1, selected from:
2-[(1S)-2-Amino-1-(3-fluorobenzyl)ethyl]-5-(1-methyl-1H-pyrazol-5-yl)isoindolin-1-one;
2-[(1S)-2-amino-1-(3-fluorobenzyl)ethyl]-5-(4-chloro-1-methyl-1H-pyrazol-5-yl)isoindolin-1-one;
2-[(1S)-2-amino-1-(3-fluorobenzyl)ethyl]-5-(4-methyl-1-methyl-1H-pyrazol-5-yl)isoindolin-1-one;
2-[(1S)-2-amino-1-(3-fluorobenzyl)ethyl]-5-(4-methoxymethyl-1-methyl-1H-pyrazol-5-yl)isoindolin-1-one;
2-[(1S)-2-amino-1-(3-fluorobenzyl)ethyl]-5-(4-ethoxymethyl-1-methyl-1H-pyrazol-5-yl)isoindolin-1-one;
2-[(1S)-2-amino-1-(3-fluorobenzyl)ethyl]-5-[4-(2-propoxymethyl)-1-methyl-1H-pyrazol-5-yl]isoindolin-1-one;
2-[(1S)-2-amino-1-(3-fluorobenzyl)ethyl]-5-[4-(1-propoxymethyl)-1-methyl-1H-pyrazol-5-yl]isoindolin-1-one;
2-[(1S)-2-amino-1-(3-fluorobenzyl)ethyl]-5-(4-cyclobutoxymethyl-1-methyl-1H-pyrazol-5-yl)isoindolin-1-one;
2-[(1S)-2-amino-1-(3-fluorobenzyl)ethyl]-5-(4-cyclopropylmethoxymethyl-1-methyl-1H-pyrazol-5-yl)isoindolin-1-one;
2-[(1S)-2-amino-1-(3-fluorobenzyl)ethyl]-5-[(methylthio)methyl-1-methyl-1H-pyrazol-5-yl]isoindolin-1-one;
2-[(1S)-2-amino-1-(3-fluorobenzyl)ethyl]-5-(4-fluoro-1-methyl-1H-pyrazol-5-yl)isoindolin-1-one;
2-[(1S)-2-amino-1-(3-fluorobenzyl)ethyl]-5-(4-bromo-1-methyl-1H-pyrazol-5-yl)isoindolin-1-one;
2-[(1S)-2-amino-1-(3-fluorobenzyl)ethyl]-5-(4-cyano-1-methyl-1H-pyrazol-5-yl)isoindolin-1-one;
2-[(1S)-2-amino-1-(3-fluorobenzyl)ethyl]-5-(4-phenyl-1-methyl-1H-pyrazol-5-yl)isoindolin-1-one;
2-[(1S)-2-amino-1-(3-fluorobenzyl)ethyl]-5-[1-methyl-4-(2-thienyl)-1H-pyrazol-5-yl]isoindolin-1-one;
2-[(1S)-2-amino-1-(3-fluorobenzyl)ethyl]-5-[1-methyl-4-(3-thienyl)-1H-pyrazol-5-yl]isoindolin-1-one;
2-[(1S)-2-amino-1-(3-fluorobenzyl)ethyl]-5-(1',2-dimethyl-1'H,2H-3,4'-bipyrazol-5'-yl)isoindolin-1-one;
2-[(1S)-2-amino-1-(3-fluorobenzyl)ethyl]-5-(1-methyl-4-pyridin-4-yl-1H-pyrazol-5-yl)isoindolin-1-one;
2-[(1S)-2-amino-1-(3-fluorobenzyl)ethyl]-5-(1-methyl-4-pyridin-4-yl-1H-pyrazol-5-yl)isoindolin-1-one;
2-[(1S)-2-amino-1-(3-fluorobenzyl)ethyl]-5-[1-methyl-4-(1,3-thiazol-2-yl)-1H-pyrazol-5-yl]isoindolin-1-one;
2-[(1S)-2-amino-1-(3-fluorobenzyl)ethyl]-5-[1-methyl-4-(2-naphthyl)-1H-pyrazol-5-yl]isoindolin-1-one;
2-[(1S)-2-amino-1-(3-fluorobenzyl)ethyl]-5-[1-methyl-4-(1-naphthyl)-1H-pyrazol-5-yl]isoindolin-1-one;
2-[(1S)-2-amino-1-(3-fluorobenzyl)ethyl]-5-(1-methyl-4-pyrimidin-5-yl-1H-pyrazol-5-yl)isoindolin-1-one;
2-[(1S)-2-amino-1-(3-fluorobenzyl)ethyl]-5-[4-(2-fluoropyridin-3-yl)-1-methyl-1H-pyrazol-5-yl]isoindolin-1-one;
2-[(1S)-2-amino-1-(3-fluorobenzyl)ethyl]-5-[4-(6-fluoropyridin-3-yl)-1-methyl-1H-pyrazol-5-yl]isoindolin-1-one;
2-[(1S)-2-amino-1-(3-fluorobenzyl)ethyl]-5-[4-(5-fluoropyridin-3-yl)-1-methyl-1H-pyrazol-5-yl]isoindolin-1-one;
2-[(1S)-2-amino-1-(3-fluorobenzyl)ethyl]-5-[4-(2-methoxypyridin-3-yl)-1-methyl-1H-pyrazol-5-yl]isoindolin-1-one;
2-[(1S)-2-amino-1-(3-fluorobenzyl)ethyl]-5-[4-(6-methoxypyridin-3-yl)-1-methyl-1H-pyrazol-5-yl]isoindolin-1-one;
5-(5-{2-[(1S)-2-amino-1-(3-fluorobenzyl)ethyl]-1-oxo-2,3-dihydro-1H-isoindol-5-yl}-1-methyl-1H-pyrazol-4-yl)-N-methylpyridine-2-carboxamide;
5-(4-chloro-1-methyl-1H-pyrazol-5-yl)-2-[(1S)-1-(3-fluorobenzyl)-2-(methylamino)-ethyl]isoindolin-1-one;
5-(4-chloro-1-methyl-1H-pyrazol-5-yl)-2-[(1S)-2-(ethylamino)-1-(3-fluorobenzyl)-ethyl]isoindolin-1-one;
5-(4-chloro-1-methyl-1H-pyrazol-5-yl)-2-[(1S)-1-(3-fluorobenzyl)-2-(isopropylamino)ethyl]isoindolin-1-one;

5-(4-chloro-1-methyl-1H-pyrazol-5-yl)-2-[(1S)-2-(cyclopropylamino)-1-(3-fluorobenzyl)ethyl]isoindolin-1-one;

5-(4-chloro-1-methyl-1H-pyrazol-5-yl)-2-[(1S)-2-(cyclobutylamino)-1-(3-fluorobenzyl)ethyl]isoindolin-1-one;

5-(4-chloro-1-methyl-1H-pyrazol-5-yl)-2-[(1S)-2-(cyclopentylamino)-1-(3-fluorobenzyl)ethyl]isoindolin-1-one;

5-(4-chloro-1-methyl-1H-pyrazol-5-yl)-2-[(1S)-1-(3-fluorobenzyl)-2-(tetrahydro-2H-pyran-4-ylamino)ethyl]isoindolin-1-one;

5-(4-chloro-1-methyl-1H-pyrazol-5-yl)-2-{(1S)-1-(3-fluorobenzyl)-2-[(1-methylpiperidin-4-yl)amino]ethyl}isoindolin-1-one;

5-(4-chloro-1-methyl-1H-pyrazol-5-yl)-2-[(1S)-2-(dimethylamino)-1-(3-fluorobenzyl)ethyl]isoindolin-1-one;

5-(4-chloro-1-methyl-1H-pyrazol-5-yl)-2-[(1S)-2-(diethylamino)-1-(3-fluorobenzyl)ethyl]isoindolin-1-one;

2-[(1S)-2-amino-1-(3,5-difluorobenzyl)ethyl]-5-(1-methyl-1H-pyrazol-5-yl)isoindolin-1-one;

2-[(1S)-2-amino-1-(3,5-difluorobenzyl)ethyl]-5-(4-chloro-1-methyl-1H-pyrazol-5-yl)isoindolin-1-one;

2-[(1S)-2-amino-1-(3,5-difluorobenzyl)ethyl]-5-(4-methyl-1-methyl-1H-pyrazol-5-yl)isoindolin-1-one;

2-[(1S)-2-amino-1-(3,5-difluorobenzyl)ethyl]-5-(4-methoxymethyl-1-methyl-1H-pyrazol-5-yl)isoindolin-1-one;

2-[(1S)-2-amino-1-(3,5-difluorobenzyl)ethyl]-5-(4-ethoxymethyl-1-methyl-1H-pyrazol-5-yl)isoindolin-1-one;

2-[(1S)-2-amino-1-(3,5-difluorobenzyl)ethyl]-5-[4-(2-propoxymethyl)-1-methyl-1H-pyrazol-5-yl]isoindolin-1-one;

2-[(1S)-2-amino-1-(3,5-difluorobenzyl)ethyl]-5-[4-(1-propoxymethyl)-1-methyl-1H-pyrazol-5-yl]isoindolin-1-one;

2-[(1S)-2-amino-1-(3,5-difluorobenzyl)ethyl]-5-[4-(cyclobutoxymethyl)-1-methyl-1H-pyrazol-5-yl]isoindolin-1-one;

2-[(1S)-2-amino-1-(3,5-difluorobenzyl)ethyl]-5-[4-(cyclopropylmethoxymethyl)-1-methyl-1H-pyrazol-5-yl]isoindolin-1-one;

2-[(1S)-2-amino-1-(3,5-difluorobenzyl)ethyl]-5-[4-(methylthio)methyl-1-methyl-1H-pyrazol-5-yl]isoindolin-1-one;

2-[(1S)-2-amino-1-(3,5-difluorobenzyl)ethyl]-5-[4-(ethylthio)methyl-1-methyl-1H-pyrazol-5-yl]isoindolin-1-one;

2-[(1S)-2-amino-1-(3,5-difluorobenzyl)ethyl]-5-(4-fluoro-1-methyl-1H-pyrazol-5-yl)isoindolin-1-one;

2-[(1S)-2-amino-1-(3,5-difluorobenzyl)ethyl]-5-(4-bromo-1-methyl-1H-pyrazol-5-yl)isoindolin-1-one;

2-[(1S)-2-amino-1-(3,5-difluorobenzyl)ethyl]-5-(4-cyano-1-methyl-1H-pyrazol-5-yl)isoindolin-1-one;

2-[(1S)-2-amino-1-(3,5-difluorobenzyl)ethyl]-5-[4-(3-hydroxy-3-methylbut-1-yn-1-yl)-1-methyl-1H-pyrazol-5-yl]isoindolin-1-one;

2-[(1S)-2-amino-1-benzyl-ethyl]-5-(1-methyl-1H-pyrazol-5-yl)isoindolin-1-one;

2-[(1S)-2-amino-1-benzyl-ethyl]-5-(4-chloro-1-methyl-1H-pyrazol-5-yl)isoindolin-1-one;

2-[(1S)-2-amino-1-benzyl-ethyl]-5-(4-bromo-1-methyl-1H-pyrazol-5-yl)isoindolin-1-one;

2-[(1S)-2-amino-1-benzyl-ethyl]-5-[4-(2-propoxymethyl)-1-methyl-1H-pyrazol-5-yl]isoindolin-1-one;

2-[(1S)-2-amino-1-benzyl-ethyl]-5-[4-(methylthiomethyl)-1-methyl-1H-pyrazol-5-yl]isoindolin-1-one;

2-[2-amino-1-(2-fluorobenzyl)ethyl]-5-(4-chloro-1-methyl-1H-pyrazol-5-yl)isoindolin-1-one;

2-{2-amino-1-[3-(trifluoromethyl)benzyl]ethyl}-5-(4-chloro-1-methyl-1H-pyrazol-5-yl)isoindolin-1-one;

3-{(2S)-3-amino-2-[5-(4-chloro-1-methyl-1H-pyrazol-5-yl)-1-oxo-1,3-dihydro-2H-isoindol-2-yl]propyl}benzonitrile;

4-{(2S)-3-amino-2-[5-(4-chloro-1-methyl-1H-pyrazol-5-yl)-1-oxo-1,3-dihydro-2H-isoindol-2-yl]propyl}benzonitrile;

2-{(1S)-2-amino-1-[(2-methoxypyridin-4-yl)methyl]ethyl}-5-(4-chloro-1-methyl-1H-pyrazol-5-yl)isoindolin-1-one;

2-[(1S)-2-amino-1-(pyridin-3-ylmethyl)ethyl]-5-(4-chloro-1-methyl-1H-pyrazol-5-yl)isoindolin-1-one;

2-[(1S)-2-amino-1-(pyridin-2-ylmethyl)ethyl]-5-(4-chloro-1-methyl-1H-pyrazol-5-yl)isoindolin-1-one;

2-[(1S)-2-amino-1-(2-thienylmethyl)ethyl]-5-(4-chloro-1-methyl-1H-pyrazol-5-yl)isoindolin-1-one;

2-[(1S)-2-amino-1-(3-thienylmethyl)ethyl]-5-(4-chloro-1-methyl-1H-pyrazol-5-yl)isoindolin-1-one;

2-[(1S)-2-amino-1-(1,3-thiazol-4-ylmethyl)ethyl]-5-(4-chloro-1-methyl-1H-pyrazol-5-yl)isoindolin-1-one;

2-{(1S)-2-amino-1-[3-(1-methyl-1H-pyrazol-4-yl)benzyl]ethyl}-5-(4-chloro-1-methyl-1H-pyrazol-5-yl)isoindolin-1-one;

2-{(1S)-2-amino-1-[3-(3-thienyl)benzyl]ethyl}-5-(4-chloro-1-methyl-1H-pyrazol-5-yl)isoindolin-1-one;

2-[(1S)-2-amino-1-(3-pyridin-4-ylbenzyl)ethyl]-5-(4-chloro-1-methyl-1H-pyrazol-5-yl)isoindolin-1-one;

2-[(1S)-2-amino-1-(3-pyridin-3-ylbenzyl)ethyl]-5-(4-chloro-1-methyl-1H-pyrazol-5-yl)isoindolin-1-one;

2-[(1S)-2-amino-1-(3-pyrimidin-5-ylbenzyl)ethyl]-5-(4-chloro-1-methyl-1H-pyrazol-5-yl)isoindolin-1-one;

3-{(2S)-3-amino-2-[5-(1-methyl-1H-pyrazol-5-yl)-1-oxo-1,3-dihydro-2H-isoindol-2-yl]propyl}benzonitrile;

2-[(1S)-2-amino-1-(1-benzothien-3-ylmethyl)ethyl]-5-(1-methyl-1H-pyrazol-5-yl)isoindolin-1-one;

2-{(1S)-2-amino-1-[(2-methoxypyridin-4-yl)methyl]ethyl}-5-(1-methyl-1H-pyrazol-5-yl)isoindolin-1-one;

2-[(1S)-2-amino-1-(pyridin-3-ylmethyl)ethyl]-5-(1-methyl-1H-pyrazol-5-yl)isoindolin-1-one;

2-[(1S)-2-amino-1-(pyridin-2-ylmethyl)ethyl]-5-(1-methyl-1H-pyrazol-5-yl)isoindolin-1-one;

2-[(1S)-2-amino-1-(2-thienylmethyl)ethyl]-5-(1-methyl-1H-pyrazol-5-yl)isoindolin-1-one;

2-[(1S)-2-amino-1-(3-thienylmethyl)ethyl]-5-(1-methyl-1H-pyrazol-5-yl)isoindolin-1-one;

2-[(1S)-2-amino-1-(1,3-thiazol-4-ylmethyl)ethyl]-5-(1-methyl-1H-pyrazol-5-yl)isoindolin-1-one;

2-{(1S)-2-amino-1-[3-(1-methyl-1H-pyrazol-4-yl)benzyl]ethyl}-5-(1-methyl-1H-pyrazol-5-yl)isoindolin-1-one;

2-{(1S)-2-amino-1-[3-(3-thienyl)benzyl]ethyl}-5-(1-methyl-1H-pyrazol-5-yl)isoindolin-1-one;

2-[(1S)-2-amino-1-(3-pyridin-4-ylbenzyl)ethyl]-5-(1-methyl-1H-pyrazol-5-yl)isoindolin-1-one;

2-[(1S)-2-amino-1-(3-pyridin-3-ylbenzyl)ethyl]-5-(1-methyl-1H-pyrazol-5-yl)isoindolin-1-one;

2-[(1S)-2-amino-1-(3-pyrimidin-5-ylbenzyl)ethyl]-5-(1-methyl-1H-pyrazol-5-yl)isoindolin-1-one;

2-[(1S)-2-amino-1-(3-ethynylbenzyl)ethyl]-5-(1-methyl-1H-pyrazol-5-yl)isoindolin-1-one;

2-[(1S)-2-amino-1-(3-ethynylbenzyl)ethyl]-5-(4-chloro-1-methyl-1H-pyrazol-5-yl)isoindolin-1-one;

6-[(1S)-2-amino-1-(3-fluorobenzyl)ethyl]-3-(4-chloro-1-methyl-1H-pyrazol-5-yl)-5,6-dihydro-7H-pyrrolo[3,4-b]pyridin-7-one;

6-[(1S)-2-amino-1-(3-fluorobenzyl)ethyl]-3-(4-bromo-1-methyl-1H-pyrazol-5-yl)-5,6-dihydro-7H-pyrrolo[3,4-b]pyridin-7-one;

2-[(1S)-2-amino-1-(3-fluorobenzyl)ethyl]-6-(4-chloro-1-methyl-1H-pyrazol-5-yl)-1,2-dihydro-3H-pyrrolo[3,4-c]pyridin-3-one;

2-[(1S)-2-amino-1-(3-fluorobenzyl)ethyl]-6-(1-methyl-1H-pyrazol-5-yl)-1,2-dihydro-3H-pyrrolo[3,4-c]pyridin-3-one;

2-[(1S)-2-amino-1-(3-fluorobenzyl)ethyl]-6-(4-methyl-1-methyl-1H-pyrazol-5-yl)-1,2-dihydro-3H-pyrrolo[3,4-c]pyridin-3-one;

2-[(1S)-2-amino-1-(3-fluorobenzyl)ethyl]-6-[4-(2-propoxymethyl)-1-methyl-1H-pyrazol-5-yl]-1,2-dihydro-3H-pyrrolo[3,4-c]pyridin-3-one;

2-[(1S)-2-amino-1-(3-fluorobenzyl)ethyl]-6-[4-(1-propoxymethyl)-1-methyl-1H-pyrazol-5-yl]-1,2-dihydro-3H-pyrrolo[3,4-c]pyridin-3-one;

2-[(1S)-2-amino-1-(3-fluorobenzyl)ethyl]-6-[4-(cyclobutoxymethyl)-1-methyl-1H-pyrazol-5-yl]-1,2-dihydro-3H-pyrrolo[3,4-c]pyridin-3-one;

2-[(1S)-2-amino-1-(3-fluorobenzyl)ethyl]-6-[4-(ethylthiomethyl)-1-methyl-1H-pyrazol-5-yl]-1,2-dihydro-3H-pyrrolo[3,4-c]pyridin-3-one;

2-[(1S)-2-amino-1-(3-fluorobenzyl)ethyl]-6-[4-(methylthiomethyl)-1-methyl-1H-pyrazol-5-yl]-1,2-dihydro-3H-pyrrolo[3,4-c]pyridin-3-one;

2-((1S)-2-amino-1-benzylethyl)-6-(4-chloro-1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-(4-chloro-1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-(1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-(4-methyl-1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-(4-broro-1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-(4-methoxymethyl-1-methyl-1H-pyrazol-5-yl)-1,2-dihydro-3H-pyrrolo[3,4-c]pyridin-3-one;

2-[(1S)-2-amino-1-(3,5-difluorobenzyl)ethyl]-6-[4-(2-propoxymethyl)-1-methyl-1H-pyrazol-5-yl]-1,2-dihydro-3H-pyrrolo[3,4-c]pyridin-3-one;

2-[(1S)-2-amino-1-(3,5-difluorobenzyl)ethyl]-6-[4-(1-propoxymethyl)-1-methyl-1H-pyrazol-5-yl]-1,2-dihydro-3H-pyrrolo[3,4-c]pyridin-3-one;

2-[(1S)-2-amino-1-(3,5-difluorobenzyl)ethyl]-6-[4-(cyclobutoxymethyl)-1-methyl-1H-pyrazol-5-yl]-1,2-dihydro-3H-pyrrolo[3,4-c]pyridin-3-one;

6-[(1S)-2-amino-1-(3-fluorobenzyl)ethyl]-2-(4-chloro-1-methyl-1H-pyrazol-5-yl)-6,7-dihydro-5H-pyrrolo[3,4-b]pyridin-5-one;

6-[(1S)-2-amino-1-(3-fluorobenzyl)ethyl]-2-(1-methyl-1H-pyrazol-5-yl)-6,7-dihydro-5H-pyrrolo[3,4-b]pyridin-5-one;

6-[(1S)-2-amino-1-benzylethyl]-2-(1-methyl-1H-pyrazol-5-yl)-6,7-dihydro-5H-pyrrolo[3,4-b]pyridin-5-one;

6-[(1S)-2-amino-1-benzylethyl]-2-(4-chloro-1-methyl-1H-pyrazol-5-yl)-6,7-dihydro-5H-pyrrolo[3,4-b]pyridin-5-one;

6-[(1S)-2-amino-1-benzyl-ethyl]-2-(4-chloro-1-methyl-1H-pyrazol-5-yl)-6,7-dihydro-5H-pyrrolo[3,4-d]pyrimidin-5-one;

2-[(1R)-2-amino-1-phenylethyl]-5-(4-chloro-1-methyl-1H-pyrazol-5-yl)isoindolin-1-one;

2-[(2-(dimethylamino)-1-phenylethyl]-5-(1-methyl-1H-pyrazol-5-yl)isoindolin-1-one;

2-[(1R)-2-amino-1-phenylethyl]-5-(1-methyl-1H-pyrazol-5-yl)isoindolin-1-one;

2-[2-amino-1-(3-fluorophenyl)ethyl]-5-(1-methyl-1H-pyrazol-5-yl)isoindolin-1-one;

2-[2-amino-1-(4-fluorophenyl)ethyl]-5-(1-methyl-1H-pyrazol-5-yl)isoindolin-1-one;

2-[2-amino-1-(3-methoxyphenyl)ethyl]-5-(1-methyl-1H-pyrazol-5-yl)isoindolin-1-one;

2-[2-amino-1-(4-methoxyphenyl)ethyl]-5-(1-methyl-1H-pyrazol-5-yl)isoindolin-1-one;

5-(4-chloro-1-methyl-1H-pyrazol-5-yl)-2-[2-(dimethylamino)-1-phenylethyl]isoindolin-1-one;

2-[(1R)-2-amino-1-phenylethyl]-5-[4-(2-propoxymethyl)-1-methyl-1H-pyrazol-5-yl]isoindolin-1-one;

2-[2-amino-1-(3-fluorophenyl)ethyl]-5-(4-chloro-1-methyl-1H-pyrazol-5-yl)isoindolin-1-one;

2-[2-amino-1-(4-fluorophenyl)ethyl]-5-(4-chloro-1-methyl-1H-pyrazol-5-yl)isoindolin-1-one;

2-[2-amino-1-(3-methoxyphenyl)ethyl]-5-(4-chloro-1-methyl-1H-pyrazol-5-yl)isoindolin-1-one;

2-[2-amino-1-(4-methoxyphenyl)ethyl]-5-(4-chloro-1-methyl-1H-pyrazol-5-yl)isoindolin-1-one;

2-[(1S)-2-amino-1-(3-fluorobenzyl)ethyl]-5-(1-ethyl-1H-pyrazol-5-yl)isoindolin-1-one;

2-[(1S)-2-amino-1-(3,5-difluorobenzyl)ethyl]-5-(1-ethyl-1H-pyrazol-5-yl)isoindolin-1-one;

2-[(1S)-2-amino-1-(cyclohexylmethyl)ethyl]-5-(1-methyl-1H-pyrazol-5-yl)isoindolin-1-one;

2-[(1S)-2-amino-1-(cyclohexylmethyl)ethyl]-5-(4-chloro-1-methyl-1H-pyrazol-5-yl)isoindolin-1-one;

2-[(1S)-2-amino-1-(cyclohexylmethyl)ethyl]-5-[4-(methoxymethyl)-1-methyl-1H-pyrazol-5-yl]isoindolin-1-one;

2-[(1S)-2-amino-1-(cyclohexylmethyl)ethyl]-6-(1-methyl-1H-pyrazol-5-yl)-1,2-dihydro-3H-pyrrolo[3,4-c]pyridin-3-one;

2-[(1S)-2-amino-1-(cyclohexylmethyl)ethyl]-6-(4-chloro-1-methyl-1H-pyrazol-5-yl)-1,2-dihydro-3H-pyrrolo[3,4-c]pyridin-3-one;

2-[(1S)-2-amino-1-(cyclopropylmethyl)ethyl]-5-(1-methyl-1H-pyrazol-5-yl)isoindolin-1-one;

2-[(1S)-2-amino-1-(cyclopropylmethyl)ethyl]-5-(4-chloro-1-methyl-1H-pyrazol-5-yl)isoindolin-1-one;

or a pharmaceutically acceptable salt thereof.

32. A composition comprising a compound according to claim 1, or a pharmaceutically acceptable salt thereof, and at least one pharmaceutically acceptable carrier.

33. A method of therapeutically treating cancer comprising administering to a patient a therapeutically effective amount of a compound of claim 1, or a pharmaceutically acceptable salt thereof.

34. The method of claim 33 wherein said cancer is selected from ovarian cancer, pancreatic cancer, breast cancer, prostate cancer, colon cancer, brain cancer, lung cancer, head and neck cancer, melanoma, gastric cancer, and hepatocellular carcinoma (HCC).

35. A method of therapeutically treating Cowden syndrome comprising administering to a patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO.         : 8,895,571 B2                                              Page 1 of 1
APPLICATION NO.    : 13/650373
DATED              : November 25, 2014
INVENTOR(S)        : Taisheng Huang et al.

It is certified that error appears in the above-identified patent and that said Letters Patent is hereby corrected as shown below:

In the Specification

Column 99, line 24, delete "2-[(2-" and insert -- 2-[2- --.

In the Claims

Column 120, line 12, claim 31, delete "2-[(2-" and insert -- 2-[2- --.

Signed and Sealed this
Fourteenth Day of April, 2015

Michelle K. Lee
*Director of the United States Patent and Trademark Office*